US007265096B2

(12) United States Patent
Gallop et al.

(10) Patent No.: US 7,265,096 B2
(45) Date of Patent: Sep. 4, 2007

(54) GEMCITABINE PRODRUGS, PHARMACEUTICAL COMPOSITIONS AND USES THEREOF

(75) Inventors: Mark A. Gallop, Los Altos, CA (US); Ge Peng, Mountain View, CA (US); Thomas F. Woiwode, San Carlos, CA (US); Kenneth C. Cundy, Redwood City, CA (US)

(73) Assignee: XenoPort, Inc., Santa Clara, CA (US)

( * ) Notice: Subject to any disclaimer, the term of this patent is extended or adjusted under 35 U.S.C. 154(b) by 500 days.

(21) Appl. No.: 10/701,965

(22) Filed: Nov. 4, 2003

(65) Prior Publication Data

US 2004/0142857 A1 Jul. 22, 2004

Related U.S. Application Data

(60) Provisional application No. 60/426,247, filed on Nov. 13, 2002, provisional application No. 60/423,966, filed on Nov. 4, 2002.

(51) Int. Cl.
*A01N 43/04* (2006.01)
*A61K 31/70* (2006.01)
*C07H 19/06* (2006.01)

(52) U.S. Cl. .................. 514/49; 514/43; 536/28.1; 536/28.4

(58) Field of Classification Search ............... 536/28.1, 536/28.4; 514/43, 49
See application file for complete search history.

(56) References Cited

U.S. PATENT DOCUMENTS

| 3,845,770 | A | 11/1974 | Theeuwes et al. |
| 3,916,899 | A | 11/1975 | Theeuwes et al. |
| 5,401,838 | A | 3/1995 | Boniouklian et al. |
| 5,426,183 | A | 6/1995 | Kjell |
| 5,521,294 | A | 5/1996 | Wildfeuer |
| 5,594,124 | A | 1/1997 | Chou |
| 5,606,048 | A | 2/1997 | Chou et al. |
| 5,698,155 | A | 12/1997 | Grosswald et al. |
| 6,303,569 | B1 | 10/2001 | Greenwald et al. |
| 2003/0158089 | A1 | 8/2003 | Gallop et al. |

FOREIGN PATENT DOCUMENTS

| EP | 0272891 A2 | 6/1988 |
| EP | 0272891 A3 | 6/1988 |
| EP | 329348 A2 | 8/1989 |
| EP | 329348 A3 | 8/1989 |
| EP | 0376518 A1 | 7/1990 |
| EP | 576230 A1 | 12/1993 |
| EP | 577303 A1 | 1/1994 |
| EP | 712860 A2 | 5/1996 |
| EP | 712860 A3 | 5/1996 |
| WO | WO91/15498 A2 | 10/1991 |
| WO | WO91/15498 A3 | 10/1991 |
| WO | WO98/00173 A2 | 1/1998 |
| WO | WO98/00173 A3 | 1/1998 |
| WO | WO98/32762 A1 | 7/1998 |
| WO | WO99/33483 A1 | 7/1999 |
| WO | WO 01/20331 A1 | 3/2001 |
| WO | WO 01/21135 A2 | 3/2001 |
| WO | WO 01/21135 A3 | 3/2001 |
| WO | WO 03/043631 A2 | 5/2003 |

OTHER PUBLICATIONS

Guo et al., "Targeted delivery of a peripheral benzodiazepine receptor lignad-gemcitabine conjugate to brain tumors in a xenograft model," *Cancer Chemother. Pharmacol.* 2001, 48, 169-176.
Guo et al., "Selective Protection of 2',2'-Diflurodeoxycytidine (Gemcitabine)," *J. Org. Chem.* 1999, 64, 8319-8322.
Howard et al., "Intracerebral drug delivery in rats with lesion-induced memory deficits," *J. Neurosurg.* 1989 71(1):105-112.
Langer et al., "Chemical and Physical Structure of Polymers as Carriers for Controlled Relaease of Bioactive Agents: A Review," *J Macromol. Sci. Rev. Macromol Chem.* 1983, 23:61.
Langer, "New Method of Drug Delivery," 1990, *Science* 249:1527-1533.
Leibach et al., "Peptide transporters in the intestine and the kidney," *Ann. Rev. Nutr.* 1996, 16, 99-119.
Levy et al., "Inhibition of Calcification of Bioprosthetic Heart Valves by Local Controlled-Release Diphosphonate," *Science* 1985 228: 190.
Mackey et al., "Functional nucleoside transporters are required for gemcitabine influx and manifestation of toxicity in cancer cell lines," *Anti-Cancer Drugs*, 1998, 58, 4349-4357.
Mackey et al. "Gemcitabine Transport in *Xenopus* Oocytes Expressing Recombinant Plasma Membrane Mammalian Nucleoside Transporters," *J. Natl. Cancer Inst.* 1999, 91, 1876-1881.
Maurel et al., Phase I trial of weekly gemcitabine at 3-h infusion in refractory, heavily pretreated advanced solid tumors. *Anti-Cancer Drugs*, 2001, 12, 713-717.
Miller et al., "Smoking cessation in hospitalized patients. Results of a randomized trial," *J. Med. Chem.* 1997, 20, 409-413.
Nakashima et al. "Tetrazolium-based plaque assay for HIV-1 and HIV-2, and its use in the evaluation of antiviral compounds," *J. Virol Methods* 1989, 26, 319-329.
Patel et al., "Phase II Clinical Investigation of Gemcitabine in Advanced Soft Tissue Sarcomas and Window Evaluation of Dose Rate on Gemcitabine Triphosphate Accumulation," *J. Clin. Oncol.* 2001, 19, 3483-3489.
Prasad et al., "Cloning and Functional Expression of a cDNA Encoding a Mammalian Sodium-dependent Vitamin Transporter Mediating the Uptake of Pantothenate, Biotin, and Lipoate," *J. Biol. Chem.* 1998, 273, 7501-7506.

(Continued)

*Primary Examiner*—Patrick Lewis
(74) *Attorney, Agent, or Firm*—Dorsey & Whitney LLP.

(57) ABSTRACT

The present invention provides gemcitabine prodrugs, methods of making gemcitabine prodrugs, pharmaceutical compositions of gemcitabine prodrugs and methods of using gemcitabine prodrugs and pharmaceutical compositions thereof to treat or prevent diseases or disorders such as cancer or viral infections.

83 Claims, 8 Drawing Sheets

OTHER PUBLICATIONS

Prasad et al., "Molecular and functional characterization of the intestinal Na+-dependent multivitamin transporter," *Arch. Biochem. Biophys.* 1999, 366, 95-106.

Richardson et al., "Synthesis and restriction enzyme analysis of oligodeoxyribonucleotides containing the anti-cancer drug 2',2'-difluoro-2'-deoxycytidine," *Nucleic Acid Res.* 1992, 20, 1763-1769.

Ritzel et al., "Molecular identification and characterization of novel human and mouse concentrative Na+-nucleoside cotransporter proteins (hCNT3 and mCNT3) broadly selective for purine and pyrimidine nucleosides (system cib)," *J. Biol. Chem.* 2001, 276, 2914-2927.

Ritzel et al., "Molecular cloning, functional expression and chromosomal localization of a cDNA encoding a human Na+/nucleoside cotransporter (hCNT2) selective for purine nucleosides and uridine,"*Mol. Membr. Biol.* 1998, 15, 203-211.

Ritzel et al., "Molecular cloning and functional expression of cDNAs encoding a human Na+-nucleoside cotransporter (hCNT1)," *Am. J. Physiol.* 1997, 272, 707-714.

Rizzieri et al., "Phase I Evaluation of Prolonged-Infusion Gemcitabine With Mitoxantrone for Relapsed or Refractory Acute Leukemia," *J. Clin. Oncol.* 2002, 20, 674-679.

Saudek et al., "A Preliminary Trial of the Programmable Implantable Medication System for Insulin Delivery," *N. Engl. J. Med.*, 1989, 321: 574.

Sefton, "Implantable Pumps," *CRC Crit Ref Biomed. Eng.* 1987, 14:201.

Sudo et al. "A sensitive assay system screening antiviral compounds against herpes simplex virus type 1 and type 2," *J. Virol. Methods* 1994, 49, 169-178.

Sweeney et al., "Antitumor activity of deacetyl vinblastine amide sulfate (vindesine) in rodents and mitotic accumulation studies in culture," *Cancer Research*, 1978, 38, 2886-2891.

Tempero et al., "Randomized Phase II Comparison of Dose-Intense Gemcitabine: Thirty-Minute Infusion and Fixed Dose Rate Infusion in Patients With Pancreatic Adenocarcinom," *J. Clin. Oncol.* 2003, 21, 3402-3408.

Veerman et al., "Antitumor activity of prolonged as compared with bolus administration of 2',2'-difluorodeoxycytidine in vivo against murine colon tumors," *Cancer Chemother. Pharmacol.* 1996, 38, 335-342.

Verma et al., "Osmotically Controlled Oral Drug Delivery," *Drug Dev. Ind. Pharm.*, 2000, 26:695-708.

Wang etal., "Na+-dependent purine nucleoside transporter from human kidney: cloning and functional characterization," *Am. J. Physiol.* 1997, 273, 1058-1065.

Wang et al., "Human Placental Na+-dependent Multivitamin Transporter: Cloning, Functional Expression, Gene Structure, And Chromosomal Localization," *J. Biol. Chem.* 1999, 274, 14875-14883.

Weiss et al., "Human Tumor Cloning Assay: Clinical Applications for Overaian, Gastric, Pancreatic, and Colorectal Cancers," *Semin. Oncol.* 1985, 12, 3, (Suppl 4), 69-74.

Collins et al., "Scanning Mutagenesis of the Putative Transmembrane Segments of $K_{ir}2.1$, an Inward Rectifier Potassium Channel," *Proceedings National Academy of Science*, 1997; 94: 5456-5460.

Adibi, "The oligopeptide transporter (Pept-1) in Human Intestine: Biology and Function," *Gastroenterology* 1997, 113, 332-340.

Akrivakis et al., "Prolonged infusion of Gemcitabine in stage IV breast cancer: a phase I study," *Anti-Cancer Drugs* 1999, 10, 525-531.

Alderman, "A Review of cellulose Ethers in Hydrophilic Matrices dor Oral controlled-Release Dosage Forms," *Int. J. Pharm. Tech. & Prod. Mfr.* 1984, 5(3) 1-9.

Alexander et al., "Synthesis and cytotoxic activity of two novel 1-dodecylthio-2-decyloxypropyl-3-phosphatidic acid conjugates with gemcitabine and cytosine arabinoside," *J. Med. Chem.* 2003, 46, 4205-4208.

Baker et al., "2'-Deoxy-2'-methylenecytidine and 2'-deoxy-2',2'-difluorocytidine 5'-diphosphates: potent mechanism-based inhibitors of ribonucleotide reductase," *J. Med. Chem.* 1991, 34, 1879-1884.

Balimane et al., "Involvement of multiple transporters in the oral absorption of nucleoside analogues," *Adv Drug Deliv Rev.* Oct. 18, 1999;39(1-3):183-209.

Bamba et al., "Release Mechanisms in Gelforming Sustained Release Preparations," *Int. J. Pharm.* 1979, 2, 307.

Chatterjee et al., "Molecular mechanism of the intestinal biotin transport process," *Am. J. Physiol.* 1999, 277.605-613.

Chou et al., "Stereospecific Synthetic of 2-Doexy-2,2-difluororibonolactone and Its Use in Preparation of 2'Deoxy-2',2'-dufluoro-β-D-Ribofuranosyl Pyrimidine Necleosides: The Key Role of Selective Crystalization," *Synthesis*, 1992, 565-570.

Crawford et al., "Cloning of the Human Equilibrative, Nitrobenzylmercaptopurine Riboside (NBMPR)-insensitive Nucleoside Transporter *ei* by Functional Expression in a Transport-deficient Cell Line," *J. Biol. Chem.* 1998, 273, 5288-5293.

Di Stefano et al., "Inhibition of [3H]thymidine incorporation into DNA of rat regenerating liver by 2',2'-difluorodeoxycytidine coupled to lactosaminated poly-L-lysine," *Biochem. Pharmacol.* 1999, 57(7), 793-799.

During et al., "Controlled release of dopamine from a polymeric brain implant: in vivo characterization," 1989, *Ann. Neurol.* 25:351.

Fang et al., "Functional characterization of a recombinant sodium-dependent nucleoside transporter with selectivity for pyrimidine nucleosides (cNT1rat) by transient expression in cultured mammalian cells," *Biochem. J.* 1996, 317, 457-465.

Gandhi et al., "Prolonged Infusion of Gemcitabine: Clinical and Pharmacodynamic Studies During a Phase I Trial in Relapsed Acute Myelogenous Leukemia," *J. Clin. Oncol.* 2002, 20, 665-673.

Goodson, in "Medical Applications of Controlled Release," *supra*, vol. 2, pp. 115-138 (1984).

Green, "Gemcitabine safety overview," *Semin Oncol.* 1996, 23 (5 Suppl 10), 32-35.

Griffiths et al., "Cloning of a human nucleoside transporter implicated in the cellular uptake of adenosine and chemotherapeutic drugs," *Nat. Med.* 1997, 3, 89-93.

GEMCITABINE PRODRUGS, PHARMACEUTICAL COMPOSITIONS AND USES THEREOF

The present application claims priority under 35 U.S.C. § 119 (e) from U.S. Provisional Application Ser. Nos. 60/423,966 and 60/426,247, filed on Nov. 4, 2002 and Nov. 13, 2002, respectively.

1. TECHNICAL FIELD

The present invention relates generally to gemcitabine prodrugs, methods of making gemcitabine prodrugs, pharmaceutical compositions of gemcitabine prodrugs and methods of using gemcitabine prodrugs and pharmaceutical compositions thereof to treat or prevent diseases or disorders such as cancer.

2. BACKGROUND

A number of nucleoside analogs such as cytarabine, fludarabine, cladribine, capecitabine, gemcitabine and pentostatin are used clinically as highly effective anti-neoplastic agents. Among these, gemcitabine (2',2'-difluoro-2'-deoxycytidine, Gemzar™) is of particular interest due to its unique activity against solid tumors and is presently used therapeutically to treat bladder, breast, lung, ovarian and pancreatic cancer.

Several self-potentiating mechanisms unique to this nucleoside analog are believed responsible for the activity of gemcitabine against solid tumors. The diphosphate metabolite of gemcitabine inhibits ribonucleotide reductase, which results in lower concentrations of intracellular deoxycytidine triphosphate (dCTP) and thus, increased incorporation of the triphosphate gemcitabine metabolite into DNA, which results in inhibition of DNA synthesis and blocks completion of the cell division cycle. Additionally, reduction in dCTP concentration upregulates the enzyme cytidine kinase, which is responsible for initial phosphorylation of gemcitabine, a necessary step in the inhibition of DNA synthesis by the drug. Finally, the triphosphate metabolite of gemcitabine is an inhibitor of cytidine deaminase, which is responsible for gemcitabine inactivation by conversion to the uridine metabolite. Accordingly, the additive nature of the above factors may explain the efficacy of gemcitabine in treating solid tumors.

Synthetic derivatives of gemcitabine, including several prodrug compounds, have been previously described (see, for example, Ishitsuka et al., International Publication No. WO03/043631; Alexander et al., *J. Med. Chem.* 2003, 46, 4205-4208; Greenwald et al., U.S. Pat. No. 6,303,569; Guo et al., *Cancer Chemother. Pharmacol.* 2001, 48, 169-176; Greenwald et al., International Publication No. WO01/21135; Di Stefano et al., *Biochem. Pharmacol.* 1999, 57, 793-799; Guo et al., *J. Org. Chem.* 1999, 64, 8319-8322; Greenwald et al., International Publication No. WO99/33483; Myhren et al., International Publication No. WO98/32762; Zhao et al., International Publication No. WO98/00173; Chou et al., U.S. Pat. No. 5,606,048; Chou, U.S. Pat. No. 5,594,124; Chou et al., European Patent Application No. EP712860; Wildfeuer, U.S. Pat. No. 5,521,294; Kjell, U.S. Pat. No. 5,426,183; Chou, U.S. Pat. No. 5,401,838; Bonjouklian et al., European Patent No. EP0376518; Chou et al., European Patent Application No. EP577303; Hertel et al., European Patent Application No. EP576230; Chou et al., *Synthesis* 1992, 565-570; Richardson et al., *Nucleic Acid Res.* 1992, 20, 1763-1769; Baker et al., *J. Med. Chem.* 1991, 34, 1879-1884; Klaveness et al., International Publication No. WO91/15498; Hertel et al., European Patent Application No. EP329348; and Koppel et al., European Patent Application No. EP272891).

Previous studies have characterized multiple cellular transport mechanisms for nucleoside analog drugs and their derivatives (for a review, see Balimane et al., *Adv. Drug Delivery Rev.* 1999, 39, 183-209). A relatively hydrophilic compound, gemcitabine has limited ability to permeate plasma membranes via passive diffusion and several studies have demonstrated that gemcitabine is a substrate for equilibrative and concentrative nucleoside transporters (ENT's and CNT's respectively). Specifically, gemcitabine is transported by human ENT1, ENT2, CNT1 and CNT3, but not the purine-selective concentrative transporter CNT2 (see Mackey et al., *Cancer Res.* 1998, 58, 4349-4357; Mackey et al., *J. Natl. Cancer Inst.* 1999, 91, 1876-1881; and Fang et al., *Biochem. J.* 1996, 317, 457465).

The superior efficacy of gemcitabine against solid tumors makes gemcitabine a particularly compelling candidate for conversion to an orally bioavailable prodrug. Oral administration of cancer drugs may provide for a more convenient dosing regimen and greater efficacy than intravenous infusions of cancer drugs, which are typically used in cancer therapy. Intravenous infusions of cancer drugs require long intervals between administration to allow the patient to recover from the treatment as the IV doses given are near their toxicity limit. Oral delivery of cancer drugs may allow for the attainment of a much more attractive plasma concentration profile in which the concentration of the drug is kept just above its therapeutic threshold for an extended period. Consequently, the patient may experience fewer side effects, while still obtaining the anti-neoplastic benefit of the drug.

However, a significant problem with oral administration of gemcitabine is the intestinal toxicity of this nucleoside analog. Accordingly, there is a need for gemcitabine analogs, which lack intestinal toxicity while retaining the efficacious anti-tumor activity of the parent drug.

3. SUMMARY

These and other needs are satisfied by the disclosure herein of gemcitabine prodrugs, methods of making gemcitabine prodrugs, pharmaceutical compositions of gemcitabine prodrugs and methods of using gemcitabine prodrugs and pharmaceutical compositions thereof to treat or prevent diseases or disorders such as cancer.

In a first aspect, a compound of structural Formula (I) is provided:

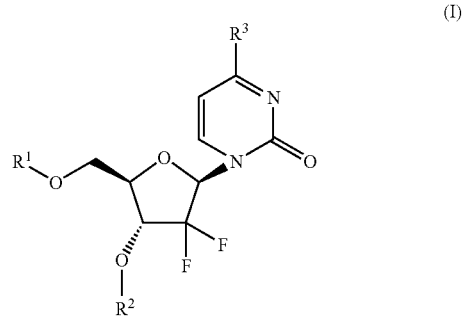

or a pharmaceutically acceptable salt, hydrate, solvate or N-oxide thereof, wherein:

$R^1$ is hydrogen, acyl, substituted acyl, acyloxyalkylcarbonyl, substituted acyloxyalkylcarbonyl, oxycarbonyl, substituted oxycarbonyl or

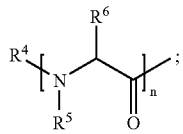

R² is hydrogen, acyl, substituted acyl, acyloxyalkylcarbonyl, substituted acyloxyalkylcarbonyl, oxycarbonyl, substituted oxycarbonyl or

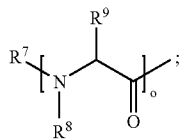

R³ is —N=C(R¹⁰)(R¹¹) or —NHR¹²;

n and o are independently integers from 1 to 3;

R⁴ and R⁷ are independently selected from the group consisting of hydrogen, alkyl, substituted alkyl, acyl, substituted acyl, acyloxyalkylcarbonyl, substituted acyloxyalkylcarbonyl, arylalkyl, substituted arylalkyl, oxycarbonyl and substituted oxycarbonyl;

R⁵ and R⁸ are independently selected from the group consisting of hydrogen, alkyl, substituted alkyl, acyl, substituted acyl, acyloxyalkylcarbonyl, substituted acyloxyalkylcarbonyl, arylalkyl, substituted arylalkyl, cycloheteroalkyl, substituted cycloheteroalkyl, heteroalkyl, substituted heteroalkyl, oxycarbonyl and substituted oxycarbonyl;

R⁶ and R⁹ are independently selected from the group consisting of hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl;

or optionally, R⁵ and R⁶ together with the nitrogen atom to which they are bonded form a cycloheteroalkyl or substituted cycloheteroalkyl ring;

or optionally, R⁸ and R⁹ together with the nitrogen atom to which they are bonded form a cycloheteroalkyl or substituted cycloheteroalkyl ring;

R¹⁰ and R¹¹ are independently selected from the group consisting of hydrogen, acyl, substituted acyl, alkyl, substituted alkyl, alkoxy, substituted alkoxy, alkylamino, substituted alkylamino, amido, substituted amido, aryl, substituted aryl, arylalkyl, substituted arylalkyl, cycloalkyl, substituted cycloalkyl, cycloheteroalkyl, substituted cycloheteroalkyl, dialkylamino, substituted dialkylamino, heteroalkyl, substituted heteroalkyl, heteroaryl, substituted heteroaryl, heteroarylalkyl and substituted heteroarylalkyl with the proviso that either R¹⁰ or R¹¹ is hydrogen;

R¹² is hydrogen, acyl, substituted acyl, acyloxyalkylcarbonyl, substituted acyloxyalkylcarbonyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, oxycarbonyl, substituted oxycarbonyl or

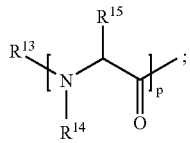

p is an integer from 1 to 3;

R¹³ is hydrogen, alkyl, substituted alkyl, acyl, substituted acyl, acyloxyalkylcarbonyl, substituted acyloxyalkylcarbonyl, arylalkyl, substituted arylalkyl, oxycarbonyl or substituted oxycarbonyl;

R¹⁴ is hydrogen, alkyl, substituted alkyl, acyl, substituted acyl, acyloxyalkylcarbonyl, substituted acyloxyalkylcarbonyl, arylalkyl, substituted arylalkyl, cycloheteroalkyl, substituted cycloheteroalkyl, heteroalkyl, substituted heteroalkyl, oxycarbonyl or substituted oxycarbonyl;

R¹⁵ is hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl; and or optionally, R¹⁴ and R¹⁵ together with the nitrogen atom to which they are bonded form a cycloheteroalkyl or substituted cycloheteroalkyl ring;

with the provisos that:

R¹ and R² are not benzoyl, $C_{18}$-$C_{20}$ acyl, tert-butoxycarbonyl or phenylaminocarbonyl;

R¹ is not 3-carboxy-propionyl, 3-alkoxycarbonyl-propionyl or 3-aminocarbonyl-propionyl when R² is hydrogen, R³ is —NHR¹² and R¹² is hydrogen;

at least one of R¹ and R² is not hydrogen when either R³ is —NHR¹² and R¹² is hydrogen, or when R³ is —N=C(R¹⁰)(R¹¹) and R¹⁰ and R¹¹ are hydrogen;

R³ is not methylcarbonylamino, tert-butylcarbonylamino, $C_{16}$-$C_{20}$ alkylcarbonylamino, benzylcarbonylamino, ethoxycarbonylamino, tert-butoxycarbonylamino, benzyloxycarbonylamino, phenylcarbonylamino or 4-methoxyphenylcarbonylamino; and when R³ is —NHR¹² and R¹ and R² are hydrogen, then R¹² is not methyl, hydroxymethyl, 2-carboxymethylamino, 2-alkoxylcarbonylmethylamino, 1-methyl-2-alkoxycarbonylmethylamino or triarylmethyl.

In a second aspect, a compound of structural Formula (II) is provided:

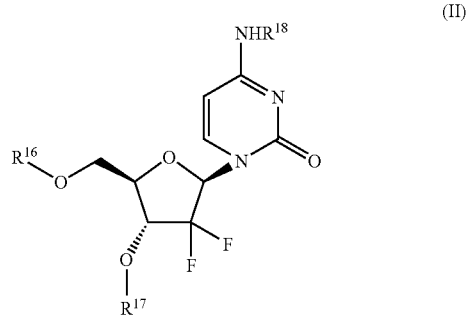

(II)

or a pharmaceutically available salt, hydrate, solvate or N-oxide thereof wherein $R^{16}$, $R^{17}$ and $R^{18}$ are independently hydrogen or

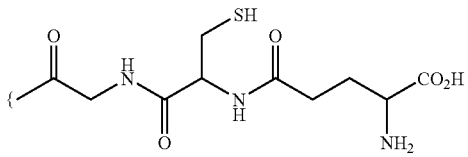

with the proviso that at least one of $R^{16}$, $R^{17}$ and $R^{18}$ is not hydrogen.

In a third aspect, pharmaceutical compositions are provided which generally comprise one or more compounds of Formulae (I) or (II), pharmaceutically acceptable salts, hydrates, solvates or N-oxides thereof and a pharmaceutically acceptable vehicle such as a diluent, carrier, excipient or adjuvant. The choice of diluent, carrier, excipient and adjuvant will depend upon, among other factors, the desired mode of administration.

In a fourth aspect, methods for treating or preventing various diseases or disorders are provided, including cancer and viral diseases. The methods generally involve administering to a patient in need of such treatment or prevention a therapeutically effective amount of a compound Formulae (I) or (II) and/or a pharmaceutical composition thereof.

4. BRIEF DESCRIPTION OF THE DRAWINGS

5. DETAILED DESCRIPTION

5.1 Definitions

Figure 1:
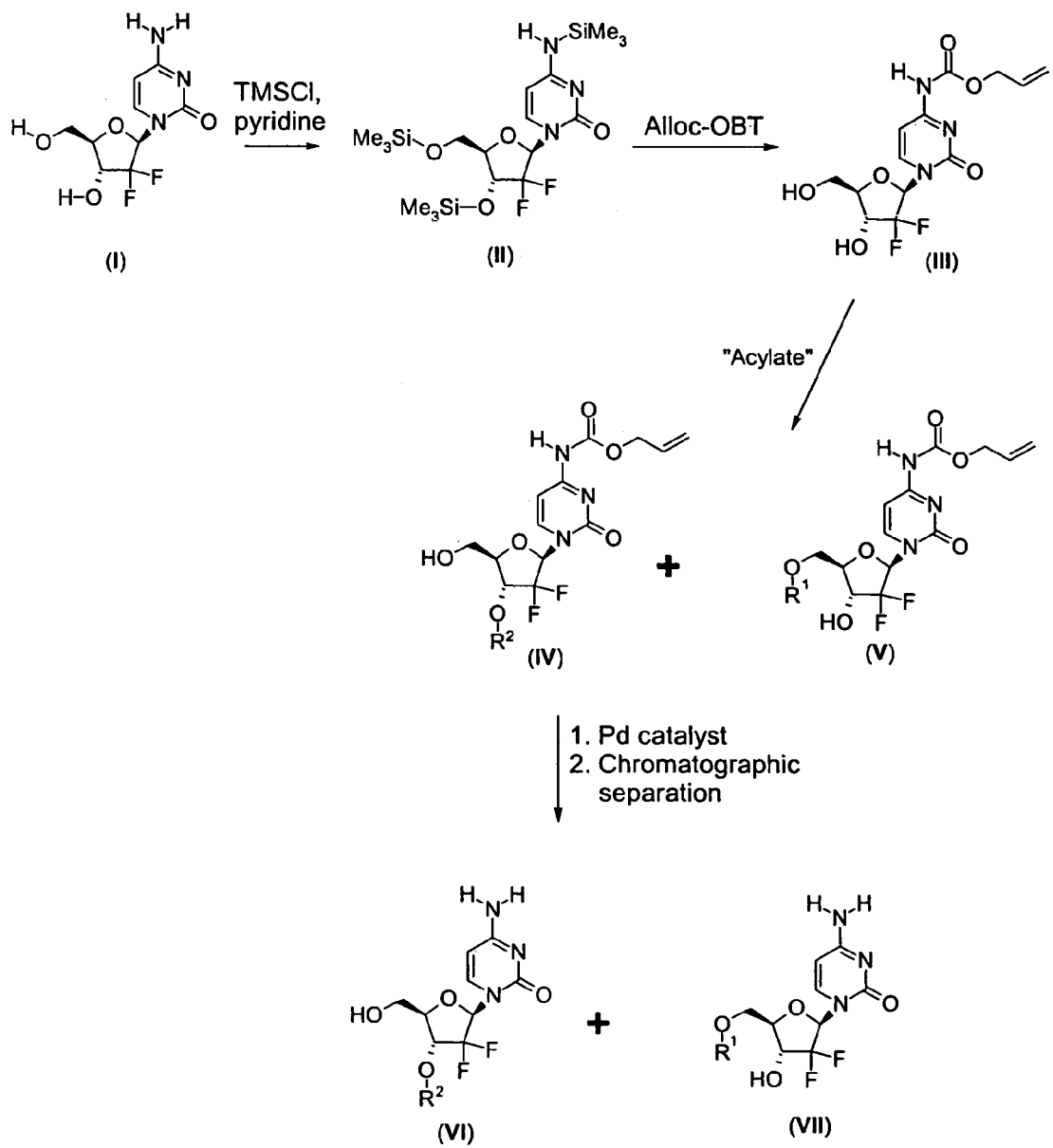
FIG. 1 illustrates a general synthetic route to monosubstituted (3'- or 5'-substituted) gemcitabine analogs.

"Alkyl" by itself or as part of another substituent refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "Alkanyl," "alkenyl," and "alkynyl" are used. Preferably, an alkyl group comprises from 1 to 20 carbon atoms, more preferably, from 1 to 10 carbon atoms. "$C_{1-6}$ alkyl" refers to an alkyl group containing from 1 to 6 carbon atoms.

"Alkanyl" by itself or as part of another substituent refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (tert-butyl), cyclobutan-1-yl, etc.; and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —C(O)$R^{30}$, where $R^{30}$ is hydrogen, alkyl, cycloalkyl, cycloheteroalkyl, aryl, arylalkyl, heteroalkyl, heteroaryl, heteroarylalkyl as defined herein. Representative examples include, but are not limited to formyl, acetyl, cyclohexylcarbonyl, cyclohexylmethylcarbonyl, benzoyl, benzylcarbonyl and the like.

"Acyloxyalkylcarbonyl" by itself or as part of another substituent refers to a radical —C(O)OC($R^{31}$)($R^{32}$)OC(O)$R^{33}$ where $R^{31}$ and $R^{32}$ are independently selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl, substituted heteroaryl, heteroarylalkyl and substituted heteroarylalkyl or optionally, $R^{31}$ and $R^{32}$ together with the carbon atom to which they are attached form a cycloalkyl, substituted cycloalkyl, cycloheteroalkyl or substituted cycloheteroalkyl ring and $R^{33}$ is selected from the group consisting of acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl.

"Alkylamino" by itself or as part of another substituent refers to a radical —NHR$^{35}$ where R$^{35}$ represents an alkyl or cycloalkyl group as defined herein. Representative examples include, but are not limited to, methylamino, ethylamino, 1-methylethylamino, cyclohexyl amino and the like.

"Alkoxy" by itself or as part of another substituent refers to a radical —OR$^{36}$ where R$^{36}$ represents an alkyl or cycloalkyl group as defined herein. Representative examples include, but are not limited to, methoxy, ethoxy, propoxy, butoxy, cyclohexyloxy and the like.

"Amido" by itself or as part of another substituent refers to a radical —NR$^{37}$C(O)R$^{38}$, where R$^{37}$ and R$^{38}$ are independently hydrogen, alkyl, cycloalkyl, cycloheteroalkyl, aryl, arylalkyl, heteroalkyl, heteroaryl or heteroarylalkyl, as defined herein. Representative examples include, but are not limited to, formylamino, acetylamino (i.e., acetamido), cyclohexylcarbonylamino, cyclohexylmethylcarbonylamino, benzoylamino (i.e., benzamido), benzylcarbonylamino and the like.

"Aryl" by itself or as part of another substituent refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryl group comprises from 6 to 20 carbon atoms, more preferably from 6 to 12 carbon atoms.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is ($C_6$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$), more preferably, an arylalkyl group is ($C_6$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Carbamoyl" by itself or as part of another substituent refers to the radical —C(O)N(R$^{39}$)R$^{40}$ where R$^{39}$ and R$^{40}$ are independently hydrogen, alkyl, substituted alkyl, aryl, substituted aryl, arylalkyl, substituted arylalkyl, heteroarylalkyl, substituted heteroarylalkyl, heteroaryl or substituted heteroaryl, as defined herein.

"CNT" refers to sodium-dependent concentrative nucleoside transporters identified in specialized mammalian cells (e.g. intestinal and renal epithelia). In humans, three gene products (hCNT1, hCNT2 and hCNT3) have been identified by molecular cloning (see Ritzel et al., *J. Biol. Chem.* 2001, 276, 2914-2927; Ritzel et al., *Mol. Membr. Biol.* 1998, 15, 203-211; Ritzel et al., *Am. J. Physiol.* 1997, 272(2 Pt 1), C707-714; and Wang et al, *Am. J. Physiol.* 1997, 273(6 Pt 2), F1058-1065).

"Compounds" refers to compounds encompassed by the generic formulae disclosed herein and includes any specific compounds within those formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, when stereochemistry at chiral centers is not specified, the chemical structures depicted herein encompass all possible configurations at those chiral centers including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds include, but are not limited to, $^2$H, $^3$H, $^{13}$C, $^{14}$C, $^{15}$N, $^{18}$O, $^{17}$O, $^{31}$P and $^{32}$P. Compounds may exist in unsolvated forms as well as solvated forms, including hydrated forms and as N-oxides. In general, the hydrated, solvated and N-oxide forms are within the scope of the present disclosure. Certain compounds may exist in multiple crystalline or amorphous forms. In general, all physical forms are equivalent for the uses contemplated herein and are intended to be within the scope of the present disclosure. Further, it should be understood, when partial structures of the compounds are illustrated, that brackets indicate the point of attachment of the partial structure to the rest of the molecule.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. Preferably, the cycloalkyl group is ($C_3$-$C_{10}$) cycloalkyl, more preferably ($C_3$-$C_7$) cycloalkyl.

"Cycloheteroalkyl" by itself or as part of another substituent refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Dialkylamino" by itself or as part of another substituent refers a radical —NR$^{41}$R$^{42}$ where R$^{41}$ and R$^{42}$ are independently an alkyl or cycloalkyl group as defined herein. Representative examples include, but are not limited to, dimethylamino, methylethylamino, di-(1-methylethyl)

amino, (cyclohexyl)(methyl)amino, (cyclohexyl)(ethyl) amino, (cyclohexyl)(propyl)amino and the like.

"ENT" refers to sodium-independent, bidirectional equilibrative nucleoside transporters. In humans, two gene products (hENT1 and hENT2) have been characterized, exhibiting broad nucleoside selectivities and wide distribution among cells and tissues (see Griffiths et al., *Nat. Med.* 1997, 3, 89-93; and Crawford et al., *J. Biol. Chem.* 1998, 273, 5288-5293).

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —O—O—, —S—S—, —O—S—, —NR$^{43}$R$^{44}$—, =N—N=, —N=N—, —N=N—NR$^{45}$R$^{46}$, —PR$^{46}$—, —P(O)$_2$—, —POR$^{48}$—, —O—P(O)$_2$—, —SO—, —SO$_2$—, —SnR$^{49}$R$^{50}$— and the like, where R$^{43}$, R$^{44}$, R$^{45}$, R$^{46}$, R$^{47}$, R$^{48}$, R$^{49}$ and R$^{50}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like. Preferably, the heteroaryl group is from 5-20 membered heteroaryl, more preferably from 5-10 membered heteroaryl. Preferred heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. In preferred embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl, more preferably, 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Oxycarbonyl" by itself or as part of another substituent refers to a radical —C(O—OR$^{51}$ where R$^{51}$ represents an alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl substituted heteroaryl, heteroarylalkyl or substituted heteroarylalkyl group as defined herein. Representative examples include, but are not limited to, methoxycarbonyl, piperdineoxycarbonyl, phenyloxycarbonyl, benzyloxycarbonyl and the like.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to a parent aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"PEPT1" refers to an oligopeptide transporter protein that absorbs peptides in certain tissues, such as the intestine. This transporter is described and characterized in the literature. See Adibi, *Gastroenterology* 1997, 113, 332-340 and Leibach et al., *Ann. Rev. Nutr.* 1996, 16, 99-119 for a discussion of this transporter.

"Pharmaceutically acceptable salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which a compound is administered.

"Patient" includes humans. The terms "human" and "patient" are used interchangeably herein.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Prodrug" refers to a derivative of a drug molecule that requires a transformation within the body to release the active drug. Prodrugs are frequently, although not necessarily, pharmacologically inactive until converted to the parent drug. A hydroxyl containing drug may be converted to, for example, a sulfonate, ester or carbonate prodrug, which may be hydrolyzed in vivo to provide the hydroxyl compound. An amino containing drug may be converted, for example, to a carbamate, amide, enamine, imine, N-phosphonyl, N-phosphoryl or N-sulfenyl prodrug, which may be hydrolyzed in vivo to provide the amino compound. A carboxylic acid drug may be converted to an ester (including silyl esters and thioesters), amide or hydrazide prodrug, which may be hydrolyzed in vivo to provide the carboxylic acid compound. Prodrugs for drugs with functional groups different than those listed above are well known to the skilled artisan.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc") trimethylsilyl ("TMS"). 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl and trityl ethers as well as alkyl ethers, tetrahydropyranyl ethers, trialkylsilyl ethers and allyl ethers.

"SMVT" refers to the sodium-dependent multivitamin transporter (SLC5A6). Genes encoding this transporter have been cloned from rat, human and rabbit tissue (see Prasad et al., *J. Biol. Chem.* 1998, 273, 7501-7506; Wang et al., *J. Biol. Chem.* 1999, 274, 14875-14883; Chattetjee et al, *Am. J. Physiol.* 1999, 277, C605-C613; Prasad et al., *Arch. Biochem. Biophys.* 1999, 366, 95-106). SMVT is expressed in intestinal, brain, liver, kidney, skeletal muscle, lung, pancreas and placental tissue. Endogenous substrates for SMVT are the micronutrients pantothenate, biotin and lipoate, each of which has binding affinities for the transporter in the range of 1-20 μM.

"Substituted" refers to a group in which one or more hydrogen atoms are independently replaced with the same or different substituent(s). Typical substituents include, but are not limited to, -M, $-R^{60}$, $-O-$, $=O$, $-OR^{60}$, $-SR^{60}$, $-S^-$, $=S$, $-NR^{60}R^{61}$, $=NR^{60}$, $-CF_3$, $-CN$, $-OCN$, $-SCN$, $-NO$, $-NO_2$, $=N_2$, $-N_3$, $-S(O)_2O^-$, $-S(O)_2OH$, $-S(O)_2R^{60}$, $-OS(O_2)O^-$, $-OS(O)_2R^{60}$, $-P(O)(O^-)_2$, $-P(O)(OR^{60})(O^-)$, $-OP(O)(OR^{60})(OR^{61})$, $-C(O)R^{60}$, $-C(S)R^{60}$, $-C(O)OR^{60}$, $-C(O)NR^{60}R^{61}$, $-C(O)O^-$, $-C(S)OR^{60}$, $-NR^{62}C(O)NR^{60}R^{61}$, $-NR^{62}C(S)NR^{60}R^{61}$, $-NR^{62}C(NR^{63})NR^{60}R^{61}$ and $-C(NR^{62})NR^{60}R^{61}$ where M is independently a halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring. Preferably, substituents include -M, $-R^{60}$, $=O$, $-OR^{60}$, $-SR^{60}$, $-S^-$, $=S$, $-NR^{60}R^{61}$, $=NR^{60}$, $-CF_3$, $-CN$, $-OCN$, $-SCN$, $-NO$, $-NO_2$, $=N_2$, $-N_3$, $-S(O)_2R^{60}$, $-OS(O_2)O^-$, $-OS(O)_2R^{60}$, $-P(O)(O^-)_2$, $-P(O)(OR^{60})(O^-)$, $-OP(O)(OR^{60})(OR^{61})$, $-C(O)R^{60}$, $-C(S)R^{60}$, $-C(O)OR^{60}$, $-C(O)NR^{60}R^{61}$, $-C(O)O^-$, $-NR^{62}C(O)NR^{60}R^{61}$, more preferably, -M, $-R^{60}$, $=O$, $-OR^{60}$, $-SR^{60}$, $-NR^{60}R^{61}$, $-CF_3$, $-CN$, $-NO_2$, $-S(O)_2R^{60}$, $-P(O)(OR^{60})(O^-)$, $-OP(O)(OR^{60})(OR^{61})$, $-C(O)R^{60}$, $-C(O)OR^{60}$, $-C(O)NR^{60}R^{61}$, $-C(O)O^-$, most preferably, -M, $-R^{60}$, $=O$, $-OR^{60}$, $-SR^{60}$, $-NR^{60}R^{61}$, $-CF_3$, $-CN$, $-NO_2$, $-S(O)_2R^{60}$, $-OP(O)(OR^{60})(OR^{61})$, $-C(O)R^{60}$, $-C(O)OR^{60}$, $-C(O)O^-$, where $R^{60}$, $R^{61}$ and $R^{62}$ are as defined above.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to inhibiting the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, etc., of the patient to be treated.

5.2 Compounds

In a first aspect, a compound of structural Formula (I) is provided:

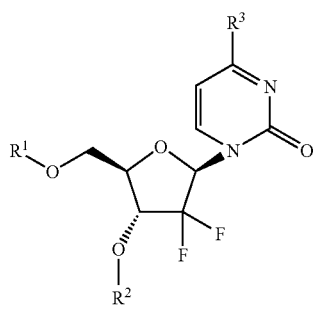

(I)

or a pharmaceutically acceptable salt, hydrate, solvate or N-oxide thereof, wherein:

$R^1$ is hydrogen, acyl, substituted acyl, acyloxyalkylcarbonyl, substituted acyloxyalkylcarbonyl, oxycarbonyl, substituted oxycarbonyl or

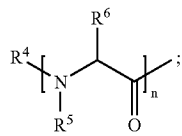

$R^2$ is hydrogen, acyl, substituted acyl, acyloxyalkylcarbonyl, substituted acyloxyalkylcarbonyl, oxycarbonyl, substituted oxycarbonyl or

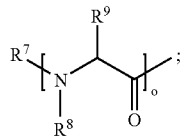

$R^3$ is $-N=C(R^{10})(R^{11})$ or $-NHR^{12}$;

n and o are independently integers from 1 to 3;

$R^4$ and $R^7$ are independently selected from the group consisting of hydrogen, alkyl substituted alkyl, acyl, substituted acyl, acyloxyalkylcarbonyl, substituted acyloxyalkylcarbonyl, arylalkyl, substituted arylalkyl, oxycarbonyl and substituted oxycarbonyl;

$R^5$ and $R^8$ are independently selected from the group consisting of hydrogen, alkyl, substituted alkyl, acyl, substituted acyl, acyloxyalkylcarbonyl, substituted acyloxyalkylcarbonyl, arylalkyl, substituted arylalkyl, cycloheteroalkyl, substituted cycloheteroalkyl, heteroalkyl, substituted heteroalkyl, oxycarbonyl and substituted oxycarbonyl;

$R^6$ and $R^9$ are independently selected from the group consisting of hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl;

or optionally, $R^5$ and $R^6$ together with the nitrogen atom to which they are bonded form a cycloheteroalkyl or substituted cycloheteroalkyl ring;

or optionally, $R^8$ and $R^9$ together with the nitrogen atom to which they are bonded form a cycloheteroalkyl or substituted cycloheteroalkyl ring;

$R^{10}$ and $R^{11}$ are independently selected from the group consisting of hydrogen, acyl, substituted acyl, alkyl, substituted alkyl, alkoxy, substituted alkoxy, alkylamino, substituted alkylamino, amido, substituted amido, aryl, substituted aryl, arylalkyl, substituted arylalkyl, cycloalkyl, substituted cycloalkyl, cycloheteroalkyl, substituted cycloheteroalkyl, dialkylamino, substituted dialkylamino, heteroalkyl, substituted heteroalkyl, heteroaryl, substituted heteroaryl, heteroarylalkyl and substituted heteroarylalkyl with the proviso that either $R^{10}$ or $R^{11}$ is hydrogen;

$R^{12}$ is hydrogen, acyl, substituted acyl, acyloxyalkylcarbonyl, substituted acyloxyalkylcarbonyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, oxycarbonyl, substituted oxycarbonyl or

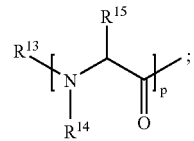

p is an integer from 1 to 3;

$R^{13}$ is hydrogen, alkyl, substituted alkyl, acyl, substituted acyl, acyloxyalkylcarbonyl, substituted acyloxyalkylcarbonyl, arylalkyl, substituted arylalkyl, oxycarbonyl or substituted oxycarbonyl;

$R^{14}$ is hydrogen, alkyl, substituted alkyl, acyl, substituted acyl, acyloxyalkylcarbonyl, substituted acyloxyalkylcarbonyl, arylalkyl, substituted arylalkyl, cycloheteroalkyl, substituted cycloheteroalkyl, heteroalkyl, substituted heteroalkyl, oxycarbonyl or substituted oxycarbonyl;

$R^{15}$ is hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl; and or optionally, $R^{14}$ and $R^{15}$ together with the nitrogen atom to which they are bonded form a cycloheteroalkyl or substituted cycloheteroalkyl ring;

with the provisos that:

$R^1$ and $R^2$ are not benzoyl, $C_{18}$-$C_{20}$ acyl, tert-butoxycarbonyl or phenylaminocarbonyl;

$R^1$ is not 3-carboxy-propionyl, 3-alkoxycarbonyl-propionyl or 3-aminocarbonyl-propionyl when $R^2$ is hydrogen, $R^3$ is $-NHR^{12}$ and $R^{12}$ is hydrogen;

at least one of $R^1$ and $R^2$ is not hydrogen when either $R^3$ is $-NHR^{12}$ and $R^{12}$ is hydrogen, or when $R^3$ is $-N=C(R^{10})(R^{11})$ and $R^{10}$ and $R^{11}$ are hydrogen;

$R^3$ is not methylcarbonylamino, tert-butylcarbonylamino, $C_{16}$-$C_{20}$ alkylcarbonylamino, benzylcarbonylamino, ethoxycarbonylamino, tert-butoxycarbonylamino, benzyloxycarbonylamino, phenylcarbonylamino or 4-methoxyphenylcarbonylamino; and when $R^3$ is $-NHR^{12}$ and $R^1$ and $R^2$ are hydrogen, then $R^{12}$ is not methyl, hydroxymethyl, 2-carboxymethylamino, 2-alkoxylcarbonylmethylamino, 1-methyl-2-alkoxycarbonylmethylamino or triarylmethyl.

In one embodiment of compounds of generic Formula (I), $R^1$ is hydrogen, acyl, substituted acyl, acyloxyalkylcarbonyl, substituted acyloxyalkylcarbonyl, oxycarbonyl or substituted oxycarbonyl. In another embodiment, $R^1$ is hydrogen, acyl or substituted acyl. In still another embodiment, $R^1$ is hydrogen, acyloxyalkylcarbonyl, substituted acyloxyalkylcarbonyl, oxycarbonyl or substituted oxycarbonyl.

In one embodiment of compounds of generic Formula (I), $R^2$ is hydrogen, acyl, substituted acyl, acyloxyalkylcarbonyl, substituted acyloxyalkylcarbonyl, oxycarbonyl or substituted oxycarbonyl. In another embodiment, $R^2$ is hydrogen, acyl or substituted acyl. In still another embodiment, $R^2$ is hydrogen, acyloxyalkylcarbonyl, substituted acyloxyalkylcarbonyl, oxycarbonyl or substituted oxycarbonyl.

In one embodiment of compounds of generic Formula (I), $R^{10}$ and $R^{11}$ are independently selected from the group consisting of hydrogen, alkoxy, substituted alkoxy, alkylamino, substituted alkylamino, amido, substituted amido, arylalkyl, substituted arylalkyl, dialkylamino, substituted dialkylamino, heteroalkyl, substituted heteroalkyl, heteroaryl, substituted heteroaryl, heteroarylalkyl and substituted heteroarylalkyl. In another embodiment, $R^{10}$ and $R^{11}$ are independently selected from the group consisting of hydrogen, alkoxy, substituted alkoxy, alkylamino, substituted alkylamino, amido, substituted amido, dialkylamino and substituted dialkylamino.

In one embodiment of compounds of generic Formula (I), $R^{12}$ is hydrogen, acyl, substituted acyl, acyloxyalkylcarbonyl, substituted acyloxyalkylcarbonyl, oxycarbonyl or substituted oxycarbonyl. In another embodiment, $R^{12}$ is hydrogen, acyl or substituted acyl. In still another embodiment, $R^{12}$ is hydrogen, acyloxyalkylcarbonyl, substituted acyloxyalkylcarbonyl, oxycarbonyl or substituted oxycarbonyl.

In one embodiment of compounds of generic Formula (I), $R^1$, $R^2$ and $R^{12}$ are independently hydrogen, acyl, substituted acyl, acyloxyalkylcarbonyl, substituted acyloxyalkylcarbonyl, oxycarbonyl or substituted oxycarbonyl. In another embodiment, $R^1$, $R^2$ and $R^2$ are independently hydrogen, acyl or substituted acyl. In still another embodiment, $R^1$, $R^2$ and $R^{12}$ are independently hydrogen, acyloxyalkylcarbonyl, substituted acyloxyalkylcarbonyl, oxycarbonyl or substituted oxycarbonyl.

In one embodiment of compounds of generic Formula (I), $R^1$ and $R^2$ are independently hydrogen, acyl, substituted acyl, acyloxyalkylcarbonyl, substituted acyloxyalkylcarbonyl, oxycarbonyl or substituted oxycarbonyl and $R^{10}$ and $R^{11}$ are independently selected from the group consisting of hydrogen, alkoxy, substituted alkoxy, alkylamino, substituted alkylamino, amido, substituted amido, arylalkyl, substituted arylalkyl, dialkylamino, substituted dialkylamino, heteroalkyl, substituted heteroalkyl, heteroaryl, substituted heteroaryl, heteroarylalkyl and substituted heteroarylalkyl. In another embodiment, $R^1$ and $R^2$ are independently hydrogen, acyl or substituted acyl and $R^{10}$ and $R^{11}$ are independently selected from the group consisting of hydrogen, alkoxy, substituted alkoxy, alkylamino, substituted alkylamino, amido, substituted amido, dialkylamino and substituted dialkylamino. In still another embodiment, $R^1$ and $R^2$ are independently hydrogen, acyloxyalkylcarbonyl, substituted acyloxyalkylcarbonyl, oxycarbonyl or substituted oxycarbonyl and $R^{10}$ and $R^{11}$ are independently selected from the group consisting of hydrogen, alkoxy, substituted alkoxy, alkylamino, substituted alkylamino, amido, substituted amido, dialkylamino and substituted dialkylamino.

In one embodiment of the compounds of generic Formula (I), n, o and p are 1.

In one embodiment of the compounds of generic Formula (I), $R^4$ and $R^7$ are independently selected from the group consisting of hydrogen, acyl, substituted acyl, acyloxyalkylcarbonyl, substituted acyloxyalkylcarbonyl, oxycarbonyl and substituted oxycarbonyl. In another embodiment, $R^4$ and $R^7$ are independently selected from the group consisting of hydrogen, acyl and substituted acyl.

In one embodiment of the compounds of generic Formula (I), $R^4$ and $R^{13}$ are independently selected from the group consisting of hydrogen, acyl, substituted acyl, acyloxyalkylcarbonyl, substituted acyloxyalkylcarbonyl, oxycarbonyl and substituted oxycarbonyl. In another embodiment, $R^4$ and $R^{13}$ are independently selected from the group consisting of hydrogen, acyl and substituted acyl.

In one embodiment of the compounds of generic Formula (I), $R^7$ and $R^{13}$ are independently selected from the group consisting of hydrogen, acyl, substituted acyl, acyloxyalkylcarbonyl, substituted acyloxyalkylcarbonyl, oxycarbonyl and substituted oxycarbonyl. In another embodiment, $R^7$ and $R^{13}$ are independently selected from the group consisting of hydrogen, acyl and substituted acyl.

In one embodiment of compounds of generic Formula (I), $R^4$, $R^7$ and $R^{13}$ are independently selected from the group consisting of hydrogen, acyl, substituted acyl, acyloxyalkylcarbonyl, substituted acyloxyalkylcarbonyl, oxycarbonyl and substituted oxycarbonyl. In another embodiment, $R^4$, $R^7$ and $R^{13}$ are independently selected from the group consisting of hydrogen, acyl and substituted acyl.

In one embodiment of compounds of generic Formula (I), $R^6$, $R^9$ and $R^{15}$ are independently selected from the group consisting of hydrogen, alkanyl, substituted alkanyl, aryl, substituted aryl, arylalkanyl, substituted arylalkanyl, cycloalkanyl, heteroarylalkyl and substituted heteroarylalkanyl. In another embodiment, $R^6$, $R^9$ and $R^{15}$ are independently selected from the group consisting of hydrogen, alkanyl and cycloalkanyl. Preferably, $R^6$, $R^9$ and $R^{15}$ are independently selected from the group consisting of hydrogen, methyl, isopropyl, isobutyl, sec-butyl, tert-butyl, cyclopentyl and cyclohexyl. In still another embodiment, $R^6$, $R^9$ and $R^{15}$ are independently substituted alkanyl. Preferably, $R^6$, $R^9$ and $R^{15}$ are independently selected from the group consisting of $-CH_2OH$, $-CH(OH)CH_3$, $-CH_2CO_2H$, $-CH_2CH_2CO_2H$, $-CH_2CONH_2$, $-CH_2CH_2CONH_2$, $-CH_2CH_2SCH_3$, $-CH_2SH$, $-CH_2(CH_2)_3NH_2$ and $-CH_2CH_2CH_2NHC(NH)NH_2$. In still another embodiment, $R^6$, $R^9$ and $R^{15}$ are independently selected from the group consisting of aryl, arylalkanyl, substituted arylalkanyl and heteroarylalkanyl. Preferably, $R^6$, $R^9$ and $R^{15}$ are independently selected from the group consisting of phenyl, benzyl, 4-hydroxybenzyl, 4-imidazolylmethyl and 3-indolylmethyl.

In one embodiment of the compounds of generic Formula (I), $R^5$ and $R^6$ or $R^8$ and $R^9$ or $R^{14}$ and $R^{15}$ together with the nitrogen atom to which they are bonded form a cycloheteroalkyl or substituted cycloheteroalkyl ring. Preferably, $R^5$ and $R^6$ or $R^8$ and $R^9$ or $R^{14}$ and $R^{15}$ together with the nitrogen atom to which they are bonded form an azetidine, pyrrolidine or piperidine ring.

In one embodiment of the compounds of generic Formula (I), $R^1$ is hydrogen or

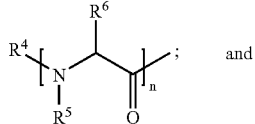; and $R^2$ and $R^{12}$ are independently hydrogen, acyl, substituted acyl, acyloxycarbonyl, substituted acyloxycarbonyl, oxycarbonyl or substituted oxycarbonyl.

In another embodiment of the compounds of generic Formula (I), $R^1$ is hydrogen or

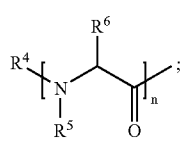;

$R^2$ is hydrogen or

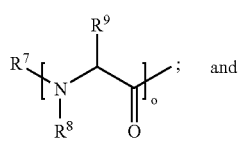; and $R^{12}$ is hydrogen, acyl, substituted acyl, acyloxycarbonyl, substituted acyloxycarbonyl, oxycarbonyl or substituted oxycarbonyl.

In another embodiment of the compounds of generic Formula (I), $R^1$ is hydrogen or

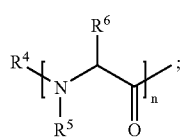;

$R^2$ is hydrogen, acyl, substituted acyl, acyloxycarbonyl, substituted acyloxycarbonyl, oxycarbonyl or substituted oxycarbonyl and $R^{12}$ is hydrogen or

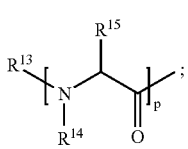.

In another embodiment of the compounds of generic Formula (I), $R^1$ is hydrogen or

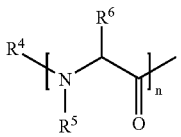

$R^2$ is hydrogen or

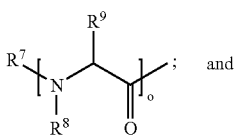; and $R^{12}$ is hydrogen or

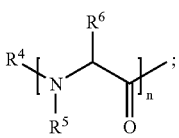.

In one embodiment of the compounds of generic Formula (I), $R^1$ is hydrogen or

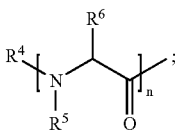

$R^2$ is hydrogen, acyl, substituted acyl, acyloxycarbonyl, substituted acyloxycarbonyl, oxycarbonyl or substituted oxycarbonyl and $R^{10}$ and $R^{11}$ are independently selected from the group consisting of hydrogen, alkoxy, substituted alkoxy, alkylamino, substituted alkylamino, amido, substituted amido, dialkylamino and substituted dialkylamino.

In one embodiment of the compounds of generic Formula (I), $R^1$ is hydrogen or

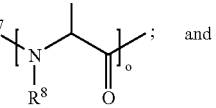

$R^2$ is hydrogen or $R^{10}$ and $R^{11}$ are independently selected from the group consisting of hydrogen, alkoxy, substituted alkoxy, alkylamino, substituted alkylamino, amido, substituted amido, dialkylamino and substituted dialkylamino.

In one embodiment of the compounds of generic Formula (I), $R^1$ is hydrogen or

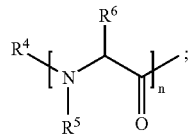

$R^2$ is hydrogen and $R^3$ is —NHR$^{12}$ where $R^{12}$ is hydrogen, acyl, substituted acyl, acyloxyalkylcarbonyl, substituted acyloxyalkylcarbonyl, oxycarbonyl or substituted oxycarbonyl. In one preferred embodiment, n is 1, $R^4$ and $R^5$ are hydrogen, $R^6$ is hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl or 3-indolylmethyl and $R^{12}$ is hydrogen, acyl or substituted acyl, or optionally, $R^5$ and $R^6$ together with the nitrogen atom to which they are bonded form an azetidine, pyrrolidine or piperidine ring. Preferably, $R^6$ is methyl, isopropyl, isobutyl, sec-butyl, tert-butyl or benzyl, $R^{12}$ is hydrogen, —C(O)R$^{21}$ or —C(O)OR$^{21}$, where $R^{21}$ is $C_{1-6}$ alkyl. In a preferred embodiment, n is 1, $R^4$ is oxycarbonyl or substituted oxycarbonyl, $R^5$ is hydrogen, $R^6$ is substituted alkyl and $R^{12}$ is hydrogen, acyl or substituted acyl. Preferably, $R^4$ is tert-butoxycarbonyl or benzyloxycarbonyl, $R^6$ is —CH$_2$CO$_2$H or —CH$_2$CH$_2$CO$_2$H, $R^{12}$ is hydrogen —C(O)R$^{21}$ or —C(O)OR$^{21}$, where $R^{21}$ is $C_{1-6}$ alkyl.

In one embodiment of the compounds of generic Formula (I), $R^1$ is acyl, substituted acyl, oxycarbonyl or substituted oxycarbonyl, $R^2$ is hydrogen, $R^3$ is —NHR$^{12}$ and $R^{12}$ is hydrogen, acyl, substituted acyl, acyloxyalkylcarbonyl, substituted acyloxyalkylcarbonyl, oxycarbonyl or substituted oxycarbonyl. Preferably, $R^1$ is substituted acyl or substituted oxycarbonyl and $R^{12}$ is hydrogen, oxycarbonyl or substituted oxycarbonyl. More preferably, $R^1$ is —C(O)(CH$_2$)$_r$CO$_2$H or —C(O)O(CH$_2$)$_r$CO$_2$H, r is an integer from 1 to 4, $R^{12}$ is —C(O)OR$^{21}$, where $R^{21}$ is $C_{1-6}$ alkyl.

In one embodiment of the compounds of generic Formula (I), $R^1$ is hydrogen or

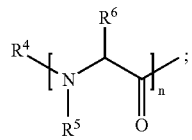

$R^2$ is hydrogen, $R^3$ is —N=C(R$^{10}$)(R$^{11}$) and $R^{10}$ and $R^{11}$ are independently selected from the group consisting of hydrogen, alkoxy, substituted alkoxy, alkylamino, substituted alkylamino, amido, substituted amido, arylalkyl, substituted arylalkyl, dialkylamino, substituted dialkylamino, heteroalkyl, substituted heteroalkyl, heteroaryl, substituted heteroaryl, heteroarylalkyl and substituted heteroarylalkyl. In one preferred embodiment, n is 1, $R^4$ and $R^5$ are hydrogen, $R^6$ is hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl or 3-indolylmethyl and $R^{10}$ and $R^{11}$ are independently selected from the group consisting of hydrogen, alkoxy, substituted alkoxy, alkylamino, substituted alkylamino, dialkylamino and substituted dialkylamino or optionally, $R^5$ and $R^6$ together with the nitrogen atom to which they are bonded form an azetidine, pyrrolidine or piperidine ring. Preferably, $R^6$ is methyl, isopropyl, isobutyl, sec-butyl, tert-butyl or benzyl and $R^{10}$ and $R^{11}$ are independently selected from the group consisting of hydrogen, methoxy and dimethylamino. In another preferred embodiment, n is 1, $R^4$ is oxycarbonyl or substituted oxycarbonyl, $R^5$ is hydrogen, $R^6$ is substituted alkyl and $R^{10}$ and $R^{11}$ are independently selected from the group consisting of hydrogen, alkoxy, substituted alkoxy, alkylamino, substituted alkylamino, dialkylamino and substituted dialkylamino. Preferably, $R^4$ is tert-butoxycarbonyl or benzyloxycarbonyl, $R^6$ is —CH$_2$CO$_2$H or —CH$_2$CH$_2$CO$_2$H and $R^{10}$ and $R^{11}$ are independently selected from the group consisting of hydrogen, methoxy and dimethylamino.

In still another embodiment of the compounds of generic Formula (I), $R^1$ is acyl, substituted acyl, oxycarbonyl or substituted oxycarbonyl, $R^2$ is hydrogen and $R^3$ is —N=C(R$^{10}$)(R$^{11}$) where $R^{10}$ and $R^{11}$ are independently selected from the group consisting of hydrogen, alkoxy, substituted alkoxy, alkylamino, substituted alkylamino, amido, substituted amido, arylalkyl, substituted arylalkyl, dialkylamino, substituted dialkylamino, heteroalkyl, substituted heteroalkyl, heteroaryl, substituted heteroaryl, heteroarylalkyl and substituted heteroarylalkyl. In a preferred embodiment, $R^1$ is substituted acyl or substituted oxycarbonyl and $R^{10}$ and $R^{11}$ are independently selected from the group consisting of hydrogen, alkoxy, substituted alkoxy, alkylamino, substituted alkylamino, dialkylamino and substituted dialkylamino. Preferably, $R^1$ is —C(O)(CH$_2$)$_r$CO$_2$H or —C(O)O(CH$_2$)$_r$CO$_2$H, r is an integer from 1 to 4 and $R^{10}$ and $R^{11}$ are independently selected from the group consisting of hydrogen, methoxy and dimethylamino.

In still another embodiment of the compounds of generic Formula (I), $R^1$ is hydrogen, $R^2$ is

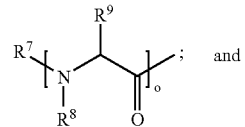

and $R^3$ is —NHR$^{12}$, where $R^{12}$ is hydrogen, acyl, substituted acyl, acyloxyalkylcarbonyl, substituted acyloxyalkylcarbonyl, oxycarbonyl or substituted oxycarbonyl. In a preferred embodiment, o is 1, $R^7$ and $R^8$ are hydrogen, $R^9$ is hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl or 3-indolylmethyl and $R^{12}$ is hydrogen, acyl, substituted acyl, oxycarbonyl or substituted oxycarbonyl, or optionally, $R^8$ and $R^9$ together with the nitrogen atom to which they are bonded form an azetidine, pyrrolidine or piperidine ring. Preferably, $R^9$ is methyl, isopropyl, isobutyl, sec-butyl, tert-butyl or benzyl $R^{12}$ is hydrogen; —C(O)$R^{21}$ or —C(O)O$R^{21}$, where $R^{21}$ is $C_{1-6}$ alkyl. In a preferred embodiment, o is 1, $R^7$ is oxycarbonyl or substituted oxycarbonyl, $R^8$ is hydrogen, $R^9$ is substituted alkyl and $R^{12}$ is hydrogen, acyl or substituted acyl. Preferably, $R^7$ is tert-butoxycarbonyl or benzyloxycarbonyl, $R^9$ is —CH$_2$CO$_2$H or —CH$_2$CH$_2$CO$_2$H and $R^{12}$ is hydrogen, —C(O)$R^{21}$ or —C(O)O$R^{21}$, where $R^{21}$ is $C_{1-6}$ alkyl.

In still another embodiment of the compounds of generic Formula (I), $R^1$ is hydrogen, $R^2$ is acyl, substituted acyl, oxycarbonyl or substituted oxycarbonyl and $R^3$ is —NH$R^{12}$, where $R^{12}$ is hydrogen, acyl, substituted acyl, acyloxyalkylcarbonyl, substituted acyloxyalkylcarbonyl, oxycarbonyl or substituted oxycarbonyl. In a preferred embodiment, $R^2$ is substituted acyl or substituted oxycarbonyl and $R^{12}$ is hydrogen, oxycarbonyl or substituted oxycarbonyl. Preferably, $R^2$ is —C(O)(CH$_2$)$_s$CO$_2$H or —C(O)O(CH$_2$)$_s$CO$_2$H, s is an integer from 1 to 4, $R^{12}$ is —C(O)O$R^{21}$, where $R^{21}$ is $C_{1-6}$ alkyl.

In still another embodiment of the compounds of generic Formula (I), $R^1$ is hydrogen, $R^2$ is

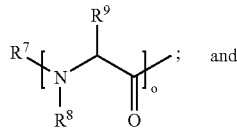

$R^3$ is —N=C($R^{10}$)($R^{11}$), where $R^{10}$ and $R^{11}$ are independently selected from the group consisting of hydrogen, alkoxy, substituted alkoxy, alkylamino, substituted alkylamino, amido, substituted amido, arylalkyl, substituted arylalkyl, dialkylamino, substituted dialkylamino, heteroalkyl, substituted heteroalkyl, heteroaryl, substituted heteroaryl, heteroarylalkyl and substituted heteroarylalkyl. In a preferred embodiment, o is 1, $R^7$ and $R^8$ are hydrogen, $R^9$ is hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl or 3-indolylmethyl and $R^{10}$ and $R^{11}$ are independently selected from the group consisting of hydrogen, alkoxy, substituted alkoxy, alkylamino, substituted alkylamino, dialkylamino and substituted dialkylamino or optionally, $R^8$ and $R^9$ together with the nitrogen atom to which they are bonded form an azetidine, pyrrolidine or piperidine ring. Preferably, $R^9$ is methyl, isopropyl, isobutyl, sec-butyl, tert-butyl or benzyl and $R^{10}$ and $R^{11}$ are independently selected from the group consisting of hydrogen, methoxy and dimethylamino. In a preferred embodiment, o is 1, $R^7$ is oxycarbonyl or substituted oxycarbonyl, $R^8$ is hydrogen, $R^9$ is substituted alkyl and $R^{10}$ and $R^{11}$ are independently selected from the group consisting of hydrogen, alkoxy, substituted alkoxy, alkylamino, substituted alkylamino, dialkylamino and substituted dialkylamino. Preferably, $R^7$ is tert-butoxycarbonyl or benzyloxycarbonyl, $R^9$ is —CH$_2$CO$_2$H or —CH$_2$CH$_2$CO$_2$H and $R^{10}$ and $R^{11}$ are independently selected from the group consisting of hydrogen, methoxy and dimethylamino.

In still another embodiment of the compounds of generic Formula (I), $R^1$ is hydrogen, $R^2$ is acyl, substituted acyl, oxycarbonyl or substituted oxycarbonyl and $R^3$ is —N=C($R^{10}$)($R^{11}$), where $R^{10}$ and $R^{11}$ are independently selected from the group consisting of hydrogen, alkoxy, substituted alkoxy, alkylamino, substituted alkylamino, amido, substituted amido, arylalkyl, substituted arylalkyl, dialkylamino, substituted dialkylamino, heteroalkyl, substituted heteroalkyl, heteroaryl, substituted heteroaryl, heteroarylalkyl and substituted heteroarylalkyl. In a preferred embodiment, $R^2$ is substituted acyl or substituted oxycarbonyl and $R^{10}$ and $R^{11}$ are independently selected from the group consisting of hydrogen, alkoxy, substituted alkoxy, alkylamino, substituted alkylamino, dialkylamino and substituted dialkylamino. Preferably, $R^2$ is —C(O)(CH$_2$)$_s$CO$_2$H or —C(O)O(CH$_2$)$_s$CO$_2$H, s is an integer from 1 to 4 and $R^{10}$ and $R^{11}$ are independently selected from the group consisting of hydrogen, methoxy and dimethylamino.

In still another embodiment of the compounds of generic Formula (I), $R^1$ and $R^2$ are independently selected from the group consisting of hydrogen, acyl, substituted acyl, oxycarbonyl or substituted oxycarbonyl, $R^3$ is NH$R^{12}$ and $R^{12}$ is

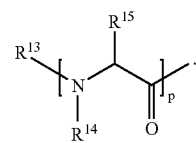

In a preferred embodiment, $R^1$ and $R^2$ are independently selected from the group consisting of hydrogen, acyl and oxycarbonyl, p is 1, $R^{13}$ and $R^{14}$ are hydrogen and $R^{15}$ is hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl or 3-indolylmethyl, or optionally, $R^{14}$ and $R^{15}$ together with the nitrogen atom to which they are bonded form an azetidine, pyrrolidine or piperidine ring. Preferably, $R^1$ is hydrogen, —C(O)$R^{19}$ or —C(O)O$R^{19}$, $R^2$ is hydrogen, —C(O)$R^{20}$ or —C(O)O$R^{20}$, $R^{19}$ and $R^{20}$ are independently $C_{1-6}$ alkyl and $R^{15}$ is methyl, isopropyl, isobutyl, sec-butyl, tert-butyl or benzyl. In another preferred embodiment, p is 1, $R^1$ is hydrogen, —C(O)$R^{19}$ or —C(O)O$R^{19}$, $R^2$ is hydrogen, —C(O)$R^{20}$ or —C(O)O$R^{20}$, $R^{19}$ and $R^{20}$ are independently $C_{1-6}$ alkyl, $R^{13}$ is oxycarbonyl or substituted oxycarbonyl, $R^{14}$ is hydrogen and $R^{15}$ is substituted alkyl. Preferably, $R^{13}$ is tert-butoxycarbonyl or benzyloxycarbonyl and $R^{14}$ is —CH$_2$CO$_2$H or —CH$_2$CH$_2$CO$_2$H.

In still another embodiment of the compounds of generic Formula (I), $R^1$ and $R^2$ are independently selected from the group consisting of hydrogen, acyl, substituted acyl, oxycarbonyl and substituted oxycarbonyl, $R^3$ is —NH$R^{12}$ and $R^{12}$ is acyl, substituted acyl, acyloxyalkylcarbonyl, substituted acyloxyalkylcarbonyl, oxycarbonyl or substituted oxycarbonyl. In one preferred embodiment, $R^{12}$ is oxycarbonyl or substituted oxycarbonyl and $R^1$ and $R^2$ are independently hydrogen, acyl or oxycarbonyl. Preferably $R^{12}$ is —C(O)O$R^{36}$, wherein $R^{36}$ is selected from the group consisting of $C_{3-6}$ alkyl, $C_{3-7}$ cycloalkyl, aryl, substituted aryl, arylalkyl, substituted arylalkyl, heteroaryl, substituted heteroaryl or CH$_2$$R^{57}$, wherein $R^{57}$ is trifluoromethyl, cyano, $C_{1-4}$ alkanesulfonyl, benzenesulfonyl or substituted benzenesulfonyl, provided that $R^{36}$ is not tert-butyl or benzyl. More preferably $R^{36}$ is selected from the group consisting of $C_{3-6}$ alkanyl, $C_{3-6}$ alk-1-en-2-yl, 2-$C_{3-7}$ cycloalkyl-eth-1-en-2-yl, 2-phenyleth-1-en-2-yl, substituted 2-phenyleth-1-en-2-yl, $C_{3-7}$ cycloalkanyl, $C_{5-7}$ cycloalk-1-en-1-yl, phenyl, naphthyl, halophenyl, methoxyphenyl, cyanophenyl, carboxyphenyl, $C_{1-4}$ alkoxycarbonylphenyl, aminophenyl, halobenzyl, methoxybenzyl, cyanobenzyl, carboxybenzyl, $C_{1-4}$ alkoxycarbonylbenzyl, aminobenzyl, furyl, thienyl, pyrrolyl, imidazoyl, oxazolyl, pyridyl, pyrimidyl, pyrazinyl and triazinyl. More preferably $R^{36}$ is selected from the group consisting of butyl, isobutyl, sec-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, propen-2-yl, buten-2-yl, phenethen-2-yl, cyclopentyl, cyclohexyl, cyclopenten-1-yl, cyclohexen-1-yl, phenyl, 4-methoxyphenyl, 4-methoxybenzyl, 1,1,1-trifluoroethyl and cyanomethyl. Preferably, $R^1$ is hydrogen, —C(O)$R^{19}$ or —C(O)O$R^{19}$, $R^2$ is hydrogen, —C(O)$R^{20}$ or —C(O)O$R^{20}$ and each of $R^{19}$ and $R^{20}$ is independently $C_{1-6}$ alkyl. More preferably $R^1$ and $R^2$ are independently hydrogen or acetyl, $R^{12}$ is —C(O)O$R^{36}$ and $R^{36}$ is butyl, isobutyl, sec-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, propen-2-yl, buten-2-yl, phenethen-2-yl, cyclopentyl, cyclohexyl, cyclopenten-1-yl, cyclohexen-1-yl, phenyl, 4-methoxyphenyl, 4-methoxybenzyl, 1,1,1-trifluoroethyl or cyanomethyl. Most preferably, $R^1$ and $R^2$ are both hydrogen.

In another preferred embodiment, $R^3$ is —NH$R^{12}$, where $R^{12}$ is acyloxyalkylcarbonyl or substituted acyloxyalkylcarbonyl and $R^1$ and $R^2$ are independently hydrogen, acyl, or oxycarbonyl. Preferably, $R^{12}$ is

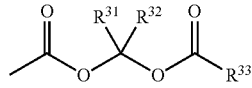

wherein:

$R^{31}$ and $R^{32}$ are independently selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl, substituted heteroaryl, heteroarylalkyl and substituted heteroarylalkyl or optionally, $R^{31}$ and $R^{32}$ together with the carbon atom to which they are attached form a cycloalkyl, substituted cycloalkyl, cycloheteroalkyl or substituted cycloheteroalkyl ring; and $R^{33}$ is selected from the group consisting of acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl.

Preferably, $R^{31}$ and $R^{32}$ are independently selected from the group consisting of hydrogen, $C_{1-4}$ alkyl, substituted $C_{1-4}$ alkyl, $C_{1-4}$ alkoxycarbonyl, $C_{3-6}$ cycloalkyl, $C_{3-6}$ cycloalkoxycarbonyl, phenyl, substituted phenyl, $C_{7-9}$ phenylalkyl and pyridyl, or optionally, $R^2$ and $R^3$ together with the carbon atom to which they are attached form a $C_{3-6}$ cycloalkyl ring; and $R^{33}$ is selected from the group consisting of $C_{1-6}$ alkyl, substituted $C_{1-6}$ alkyl, $C_{3-6}$ cycloalkyl, phenyl, substituted phenyl, $C_{7-9}$ phenylalkyl, pyridyl and substituted pyridyl.

Preferably, $R^{31}$ is hydrogen, methyl, ethyl, propyl, isopropyl, butyl, isobutyl, sec-butyl, tert-butyl, cyclopentyl, cyclohexyl, phenyl, benzyl, phenethyl or 3-pyridyl and $R^{32}$ is hydrogen, or optionally $R^{31}$ and $R^{32}$ together with the atom to which they are attached form a cyclobutyl, cyclopentyl or a cyclohexyl ring. $R^{33}$ is preferably, methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl or 3-pyridyl. Preferably, $R^1$ is hydrogen, —C(O)$R^{19}$ or —C(O)O$R^{19}$, $R^2$ is hydrogen, —C(O)$R^{20}$ or —C(O)O$R^{20}$ and each of $R^{19}$ and $R^{20}$ is independently $C_{1-6}$ alkyl. More preferably, $R^1$ and $R^2$ are both hydrogen, $R^3$ is —NH$R^{12}$ and $R^{12}$ is

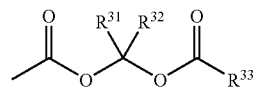

wherein $R^{31}$ is hydrogen, methyl, ethyl, propyl, isopropyl, tert-butyl, cyclopentyl, cyclohexyl or phenyl and $R^{32}$ is hydrogen; and $R^{33}$ is methyl, propyl, isopropyl, tert-butyl, phenyl, 2-methylphenyl, 2,6-dimethylphenyl, 2-methoxyphenyl, 4-methoxyphenyl, 2,6-dimethoxyphenyl, benzyl, cyclopentyl or cyclohexyl.

In another preferred embodiment, $R^3$ is —NH$R^{12}$, where $R^{12}$ is acyl, substituted acyl, alkoxycarbonyl or substituted alkoxycarbonyl and $R^1$ and $R^2$ are independently hydrogen, acyl, or oxycarbonyl. Preferably $R^{12}$ is

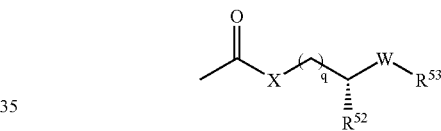

wherein:

X is O or $CH_2$;
q is 1 or 2;
$R^{52}$ is H or $CO_2H$;
W is O or $NR^{54}$;
$R^{54}$ is hydrogen or $C_{1-4}$ alkyl; and
$R^{53}$ is selected from the group consisting of $C_{1-4}$ alkyl, —C(O)$R^{30}$, —C(O)O$R^{36}$,

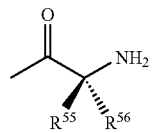 and 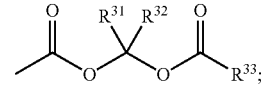;

wherein $R^{30}$ is selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl;

$R^{31}$ and $R^{32}$ are independently selected from the group consisting of hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl, substituted heteroaryl, heteroarylalkyl and substituted heteroarylalkyl or optionally, $R^{31}$ and $R^{32}$ together with the carbon atom to which they are attached form a cycloalkyl, substituted cycloalkyl, cycloheteroalkyl or substituted cycloheteroalkyl ring;

$R^{33}$ is selected from the group consisting of acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl;

$R^{36}$ is selected from the group consisting of $C_{1-6}$ alkyl, $C_{3-7}$ cycloalkyl, aryl, substituted aryl, arylalkyl, substituted arylalkyl, heteroaryl and substituted heteroaryl;

$R^{55}$ is selected from the group consisting of hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl; and $R^{56}$ is hydrogen, $C_{1-4}$ alkyl or optionally, $R^{55}$ and $R^{56}$ together with the carbon to which they are attached form a cycloalkyl or cycloheteroalkyl ring.

Preferably, $R^{30}$ is selected from the group consisting of $C_{1-6}$ alkyl, substituted $C_{1-6}$ alkyl, $C_{3-6}$ cycloalkyl, phenyl, substituted phenyl, $C_{7-9}$ phenylalkyl, pyridyl and substituted pyridyl. In one preferred embodiment, $R^{30}$ is methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl or 3-pyridyl. Preferably, $R^{31}$ is hydrogen, methyl, ethyl, propyl, isopropyl, butyl, isobutyl, sec-butyl, tert-butyl, cyclopentyl, cyclohexyl, phenyl, benzyl, phenethyl or 3-pyridyl and $R^{32}$ is hydrogen, or optionally $R^{31}$ and $R^{32}$ together with the atom to which they are attached form a cyclobutyl, cyclopentyl or a cyclohexyl ring. More preferably, $R^{31}$ is hydrogen, methyl, ethyl, propyl, isopropyl, tert-butyl, cyclopentyl, cyclohexyl or phenyl and $R^{32}$ is hydrogen. In one preferred embodiment, $R^{33}$ is methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl or 3-pyridyl. More preferably, $R^{33}$ is methyl, propyl, isopropyl, tert-butyl, phenyl, 2-methylphenyl, 2,6-dimethylphenyl, 2-methoxyphenyl, 4-methoxyphenyl, 2,6-dimethoxyphenyl, benzyl, cyclopentyl or cyclohexyl. Preferably, $R^{36}$ is selected from the group consisting of $C_{1-6}$ alkanyl, $C_{3-6}$ alk-1-en-2-yl, 2-$C_{3-7}$ cycloalkyl-eth-1-en-2-yl, 2-phenyleth-1-en-2-yl, substituted 2-phenyleth-1-en-2-yl, $C_{3-7}$ cycloalkanyl, $C_{5-7}$ cycloalk-1-en-1-yl, phenyl, naphthyl, halophenyl, methoxyphenyl, cyanophenyl, carboxyphenyl, $C_{1-4}$ alkoxycarbonylphenyl, aminophenyl, halobenzyl, methoxybenzyl, cyanobenzyl, carboxybenzyl, $C_{1-4}$ alkoxycarbonylbenzyl, aminobenzyl, furyl, thienyl, pyrrolyl, imidazoyl, oxazolyl, pyridyl, pyrimidyl, pyrazinyl and triazinyl. More preferably, $R^{36}$ is methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, propen-2-yl, buten-2-yl, phenethen-2-yl, cyclopentyl, cyclohexyl, cyclopenten-1-yl, cyclohexen-1-yl, phenyl, 4-methoxyphenyl, benzyl or 4-methoxybenzyl. Preferably, $R^{55}$ is hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl or 3-indolylmethyl. Preferably, $R^{56}$ is hydrogen or methyl.

In one embodiment, $R^1$ and $R^2$ are both hydrogen, $R^3$ is —NHR$^{12}$ and $R^{12}$ is

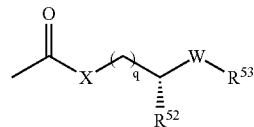

wherein:
X is O;
q is 1;
$R^{52}$ is hydrogen;
W is NR$^{54}$ and $R^{54}$ is hydrogen;
$R^{53}$ is

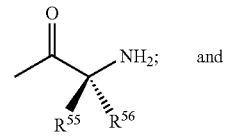   and $R^{55}$ and $R^{56}$ are as defined above. Preferably $R^{55}$ is hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl or 3-indolylmethyl and $R^{56}$ is hydrogen.

In another embodiment, $R^1$ and $R^2$ are both hydrogen, $R^3$ is —NHR$^{12}$ and $R^{12}$ is

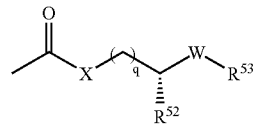

wherein:
X is O;
q is 1;
$R^{52}$ is CO$_2$H;
W is NR$^{54}$ and $R^{54}$ is hydrogen;
$R^{53}$ is

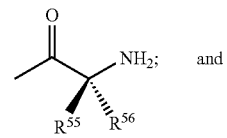   and $R^{55}$ and $R^{56}$ are as defined above. Preferably, $R^{55}$ is not cyclohexylmethyl when $R^{55}$ is hydrogen. Preferably, $R^{55}$ is hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl or 3-indolylmethyl and $R^{56}$ is hydrogen. Preferably, $R^{55}$ is methyl and $R^{56}$ is methyl. Preferably, $R^{55}$ and $R^{56}$ together with the carbon to which they are attached form a cyclohexyl ring.

In another embodiment, $R^1$ and $R^2$ are both hydrogen, $R^3$ is —NHR$^{12}$ and $R^{12}$ is

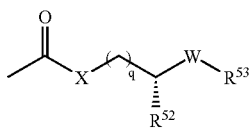

wherein:
X is O;
q is 1;
$R^{52}$ is hydrogen;
W is NR$^{54}$ and $R^{54}$ is methyl; and
$R^{53}$ is methyl.

In another embodiment, $R^1$ and $R^2$ are both hydrogen, $R^3$ is —NHR$^{12}$ and $R^{12}$ is

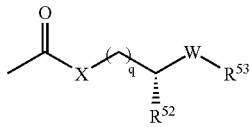

wherein:
X is O;
q is 1;
$R^{52}$ is hydrogen;
W is O; and
$R^{53}$ is —C(O)R$^{30}$.

Preferably, $R^{30}$ is selected from the group consisting of C$_{1-6}$ alkyl, substituted C$_{1-6}$ alkyl, C$_{3-6}$ cycloalkyl, phenyl, substituted phenyl, C$_{7-9}$ phenylalkyl, pyridyl and substituted pyridyl. More preferably, $R^{30}$ is methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl or 3-pyridyl.

In another embodiment, $R^1$ and $R^2$ are both hydrogen, $R^3$ is —NHR$^{12}$ and $R^{12}$ is

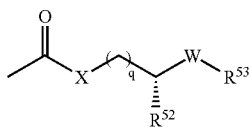

wherein:
X is O;
q is 1;
$R^{52}$ is hydrogen;
W is O; and
R is —C(O)OR$^{36}$.

Preferably, $R^{36}$ is selected from the group consisting of C$_{1-6}$ alkanyl, C$_{3-6}$ alk-1-en-2-yl, 2-C$_{3-7}$ cycloalkyl-eth-1-en-2-yl, 2-phenyleth-1-en-2-yl, substituted 2-phenyleth-1-en-2-yl, C$_{3-7}$ cycloalkanyl, C$_{5-7}$ cycloalk-1-en-1-yl, phenyl, naphthyl, halophenyl, methoxyphenyl, cyanophenyl, carboxyphenyl, C$_{1-4}$ alkoxycarbonylphenyl, aminophenyl, halobenzyl, methoxybenzyl, cyanobenzyl, carboxybenzyl, C$_{1-4}$ alkoxycarbonylbenzyl, aminobenzyl, furyl, thienyl, pyrrolyl, imidazoyl, oxazolyl, pyridyl, pyrimidyl, pyrazinyl and triazinyl. More preferably, $R^{36}$ is selected from the group consisting of methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, propen-2-yl, buten-2-yl, phenethen-2-yl, cyclopentyl, cyclohexyl, cyclopenten-1-yl, cyclohexen-1-yl, phenyl, 4-methoxyphenyl, benzyl or 4-methoxybenzyl.

In another embodiment, $R^1$ and $R^2$ are both hydrogen, $R^3$ is —NHR$^{12}$ and $R^{12}$ is

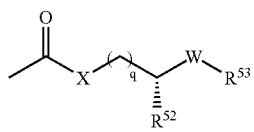

wherein:
X is O;
q is 1;
$R^{52}$ is hydrogen;
W is NR$^{54}$ and $R^{54}$ is hydrogen; and
$R^{53}$ is —C(O)OR$^{36}$.

Preferably, $R^{36}$ is selected from the group consisting of C$_{1-6}$ alkanyl, C$_{3-6}$ alk-1-en-2-yl, 2-C$_{3-7}$ cycloalkyl-eth-1-en-2-yl, 2-phenyleth-1-en-2-yl, substituted 2-phenyleth-1-en-2-yl, C$_{3-7}$ cycloalkanyl, C$_{5-7}$ cycloalk-1-en-1-yl, phenyl, naphthyl, halophenyl, methoxyphenyl, cyanophenyl, carboxyphenyl, C$_{1-4}$ alkoxycarbonylphenyl, aminophenyl, halobenzyl, methoxybenzyl, cyanobenzyl, carboxybenzyl, C$_{1-4}$ alkoxycarbonylbenzyl, aminobenzyl, furyl, thienyl, pyrrolyl, imidazoyl, oxazolyl, pyridyl, pyrimidyl, pyrazinyl and triazinyl. More preferably, $R^{36}$ is selected from the group consisting of methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, propen-2-yl, buten-2-yl, phenethen-2-yl, cyclopentyl, cyclohexyl, cyclopenten-1-yl, cyclohexen-1-yl, phenyl, 4-methoxyphenyl, benzyl or 4-methoxybenzyl.

In another embodiment, $R^1$ and $R^2$ are both hydrogen, $R^3$ is —NHR$^{12}$ and $R^{12}$ is

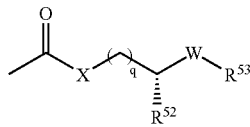

wherein:
X is CH$_2$;
q is 1;

$R^{52}$ is hydrogen;
W is O; and
$R^{53}$ is —C(O)$R^{30}$.

Perferably, $R^{30}$ is selected from the group consisting of $C_{1-6}$ alkyl, substituted $C_{1-6}$ alkyl, $C_{3-6}$ cycloalkyl, phenyl, substituted phenyl, $C_{7-9}$ phenylalkyl, pyridyl and substituted pyridyl. More preferably, $R^{30}$ is methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl or 3-pyridyl.

In another embodiment, $R^1$ and $R^2$ are both hydrogen, $R^3$ is —NH$R^{12}$ and $R^{12}$ is

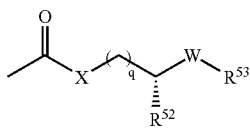

wherein:
X is CH$_2$;
q is 1;
$R^{52}$ is hydrogen;
W is O; and
$R^{53}$ is —C(O)O$R^{36}$.

Preferably, $R^{36}$ is selected from the group consisting of $C_{1-6}$ alkanyl, $C_{3-6}$ alk-1-en-2-yl, 2-$C_{3-7}$ cycloalkyl-eth-1-en-2-yl, 2-phenyleth-1-en-2-yl, substituted 2-phenyleth-1-en-2-yl, $C_{3-7}$ cycloalkanyl, $C_{5-7}$ cycloalk-1-en-1-yl, phenyl, naphthyl, halophenyl, methoxyphenyl, cyanophenyl, carboxyphenyl, $C_{1-4}$ alkoxycarbonylphenyl, aminophenyl, halobenzyl, methoxybenzyl, cyanobenzyl, carboxybenzyl, $C_{1-4}$ alkoxycarbonylbenzyl, aminobenzyl, furyl, thienyl, pyrrolyl, imidazoyl, oxazolyl, pyridyl, pyrimidyl, pyrazinyl and triazinyl. More preferably, $R^{36}$ is selected from the group consisting of methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, propen-2-yl, buten-2-yl, phenethen-2-yl, cyclopentyl, cyclohexyl, cyclopenten-1-yl, cyclohexen-1-yl, phenyl, 4-methoxyphenyl, benzyl or 4-methoxybenzyl.

In another embodiment, $R^1$ and $R^2$ are both hydrogen, $R^3$ is —NH$R^{12}$ and $R^{12}$ is

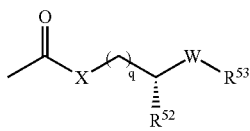

wherein:
X is O;
q is 1;
$R^{52}$ is hydrogen;

W is N$R^{54}$ and $R^{54}$ is hydrogen or methyl; and
$R^{53}$ is

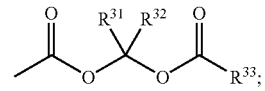

where $R^{31}$ is hydrogen, methyl, ethyl, propyl, isopropyl, tert-butyl, cyclopentyl, cyclohexyl or phenyl and $R^{32}$ is hydrogen; and $R^{33}$ is methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl or 3-pyridyl.

Preferably, $R^{33}$ is methyl, propyl, isopropyl, tert-butyl, phenyl, 2-methylphenyl, 2,6-dimethylphenyl, 2-methoxyphenyl, 4-methoxyphenyl, 2,6-dimethoxyphenyl, benzyl, cyclopentyl or cyclohexyl. More preferably, $R^{31}$ and $R^{33}$ are each tert-butyl and $R^{32}$ and $R^{54}$ are each hydrogen.

In still another embodiment of the compounds of generic Formula (I), $R^1$ and $R^2$ are independently hydrogen, acyl, substituted acyl, oxycarbonyl or substituted oxycarbonyl, $R^3$ is —N=C($R^{10}$)($R^{11}$) and $R^{10}$ and $R^{11}$ are independently selected from the group consisting of hydrogen, alkoxy, substituted alkoxy, alkylamino, substituted alkylamino, dialkylamino and substituted dialkylamino. In a preferred embodiment, $R^1$ and $R^2$ are independently hydrogen, acyl or oxycarbonyl and $R^{10}$ and $R^{11}$ are independently selected from the group consisting of hydrogen, alkoxy, substituted alkoxy, dialkylamino and substituted dialkylamino. Preferably, $R^1$ is hydrogen, —C(O)$R^{19}$ or —C(O)O$R^{19}$, $R^2$ is hydrogen, —C(O)$R^{20}$ or —C(O)O$R^{20}$, where $R^{19}$ and $R^{20}$ are independently $C_{1-6}$ alkyl and $R^{10}$ and $R^{11}$ are independently selected from the group consisting of hydrogen, ethoxy and diethylamino.

In one embodiment, at least one of $R^1$ and $R^2$ is not hydrogen when $R^3$ is —NH$R^{12}$ and $R^{12}$ is hydrogen, or when $R^3$ is —N=C($R^{10}$)($R^{11}$) and $R^{10}$ and $R^{11}$ are hydrogen;

$R^1$ and $R^2$ are not benzoyl, tert-butoxycarbonyl, phenylaminocarbonyl, $C_{18}$-$C_{20}$ acyl or

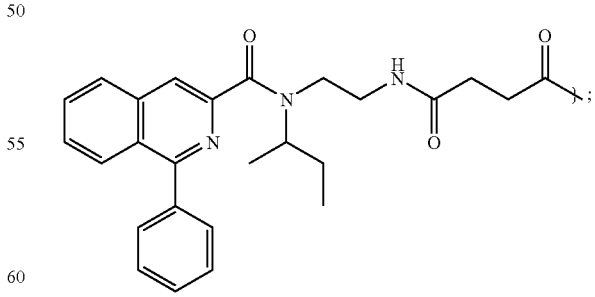

$R^3$ is not methylcarbonylamino, tert-butylcarbonylamino, $C_{16}$-$C_{20}$ alkylcarbonylamino, benzylcarbonylamino, ethoxycarbonylamino, tert-butoxycarbonylamino, benzyloxycarbonylamino, phenylcarbonylamino, 4-methoxyphenylcarbonylamino,

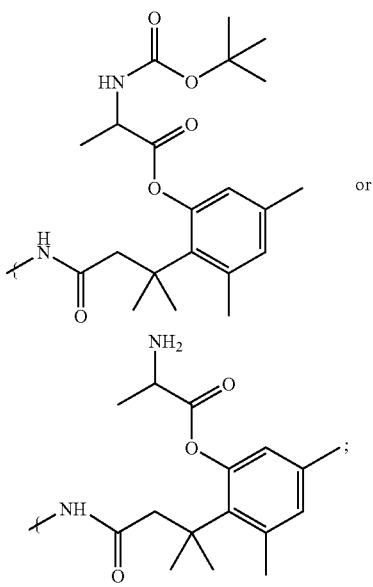

R¹ is not 3-carboxy-propionyl, 3-alkoxycarbonyl-propionyl or 3-aminocarbonyl-propionyl when R² is hydrogen, R³ is —NHR¹² and R¹² is hydrogen; and when R³ is —NHR¹² and R¹ and R² are hydrogen, then R¹² is not methyl, hydroxymethyl, 2-carboxymethylamino, 2-alkoxylcarbonylmethylamino, 1-methyl-2-alkoxycarbonylmethylamino or triarylmethyl.

In another aspect, a compound of structural Formula (II) is provided:

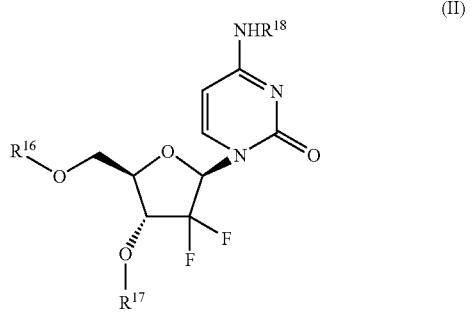

(II)

or a pharmaceutically available salt, hydrate, solvate or N-oxide thereof where $R^{16}$, $R^{17}$ and $R^{18}$ are independently hydrogen or

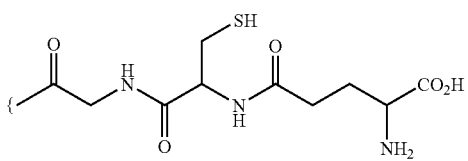

with the proviso that at least one of $R^{16}$, $R^{17}$ and $R^{18}$ is not hydrogen.

Preferred compounds of structural Formulae (I) and (II) may be administered orally and transported across cells (i.e., enterocytes) lining the lumen of the gastrointestinal tract either by active transport, passive diffusion or by a mixture of both active and passive processes. While not wishing to be bound by any particular theory, some of the compounds of structural Formulae (I) and (II) may be substrates for one or more of the nucleoside transporters that transport gemcitabine itself (i.e., ENT1, ENT2, CNT1 and CNT3). Methods for determining whether compounds of Formulae (I) and (II) serve as substrates for ENT and CNT transporters are disclosed in Example 61 herein (see Section 6.61).

Other preferred compounds of structural Formulae (I) and (II) may be substrates for the proton-coupled intestinal peptide transport system ("PEPT1") (Leibach et al., *Annu. Rev. Nutr.* 1996, 16, 99-119) which, typically mediates the cellular uptake of small intact peptides consisting of two or three amino acids that are derived from the digestion of dietary proteins. In the intestine, where small peptides are not effectively absorbed by passive diffusion, PEPT1 may act as a vehicle for their effective uptake across the apical membrane of the gastric mucosa. Methods for determining whether compounds of Formulae (I) and (II) serve as substrates for the PEPT1 transporter are disclosed in Example 59 herein (see Section 6.59). In vitro systems, which use cells engineered to heterologously express the transport system, or cell-lines that endogenously express the transporter (e.g., Caco-2 cells) may be used to assay transport of compounds of Formulae (I) and (II) by PEPT1 transporter.

Other preferred compounds of structural Formulae (I) and (II) may be substrates for the sodium-dependent multivitamin transporter (SMVT). SMVT is expressed in intestinal, brain, liver, kidney, skeletal muscle, lung, pancreas and placental tissue. Endogenous substrates for SMVT are the micronutrients pantothenate, biotin and lipoate, each of which has binding affinities for the transporter in the range of 1-20 µM. The ability of SMVT transport mechanism to mediate intestinal absorption of pharmaceutically useful quantities of low molecular weight substrates (i.e., <1,500 Da) has been described in Gallop et al., U.S. patent application Ser. No. 20030158089. Methods for determining whether compounds of Formulae (I) and (II) serve as substrates for the SMVT transporter are disclosed in Example 60 herein (see Section 6.60).

5.3 Synthesis of Compounds

The compounds disclosed herein may be obtained, for example, via synthetic methods illustrated in FIGS. 1-8. Starting materials useful for preparing compounds and intermediates thereof are commercially available or can be prepared by well-known synthetic methods (Harrison et al., "Compendium of Synthetic Organic Methods", Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-17, Wiley Interscience; Trost et al., "Comprehensive Organic Synthesis," Pergamon Press, 1991; "Theilheimer's Synthetic Methods of Organic Chemistry," Volumes 145, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995). Other methods for synthesis of the compounds described herein and/or starting materials are either described in the art or will be readily apparent to the skilled artisan. Alternatives to the reagents and/or protecting groups illustrated below may be found in the references provides above and in other compendiums well known to the skilled artisan. Accordingly, the synthetic methods and strategy presented herein are illustrative rather than comprehensive.

FIG. 1 illustrates a general synthetic route to monosubstituted (3' or 5' substituted) gemcitabine analogs. Gemcitabine (I) is treated with trimethylsilyl chloride ("TMSCI") in pyridine to provide trisilyl derivative (II), which upon reaction with 1-(allyloxycarbonyl-oxy)-1H-benzotriazole ("Alloc-OBT") yields allyl carbamate (III). It should be noted that other methods of selectively protecting an amine group in the presence of hydroxy groups are known to the skilled artisan and may used in lieu of the illustrated route to generate protected amine derivatives analogous to (III). The 3', 5'-diol (III) may be treated with an acylating, acyloxyalkylcarbonylating, oxycarbonylating or aminoacylating agent (or substituted variations thereof) to provide a mixture of alcohols (IV) and (V). Methods for effecting monofunctionalization of diol (III) with the above agents are well-known to the skilled artisan and numerous examples thereof are may be found in the chemical arts. Removal of the amine protecting group (e.g. with a palladium catalyst such as $Pd(PPh_3)_4$) followed by separation (e.g., via HPLC) provides 3'-monosubstituted gemcitabine analog (VI) and 5'-monosubstituted gemcitabine analog (VII).

Figure 2:
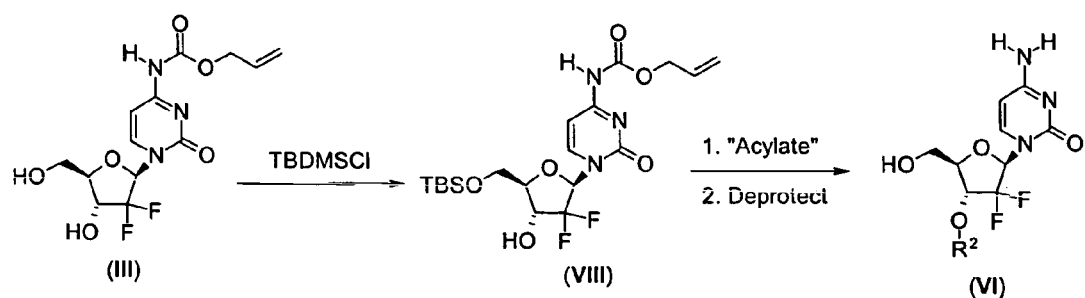
FIG. 2 illustrates a general synthetic route to 3'-substituted gemcitabine analogs.

FIG. 2 illustrates a general synthetic route to 3'-substituted gemcitabine analogs. The primary hydroxyl group in nucleoside (III) is selectively protected (e.g., tert-butyldimethylsilyl chloride, imidazole) to yield the free 3'-hydroxyl compound (VIII), which may be reacted with an appropriate acylating, acyloxyalkylcarbonylating, oxycarbonylating or aminoacylating agent (or substituted variations thereof) and then deprotected (e.g., trifluoroacetic acid or tetra-n-butylammonium fluoride then palladium catalysis) to provide the 3'-substituted gemcitabine analog (VI).

Figure 3:
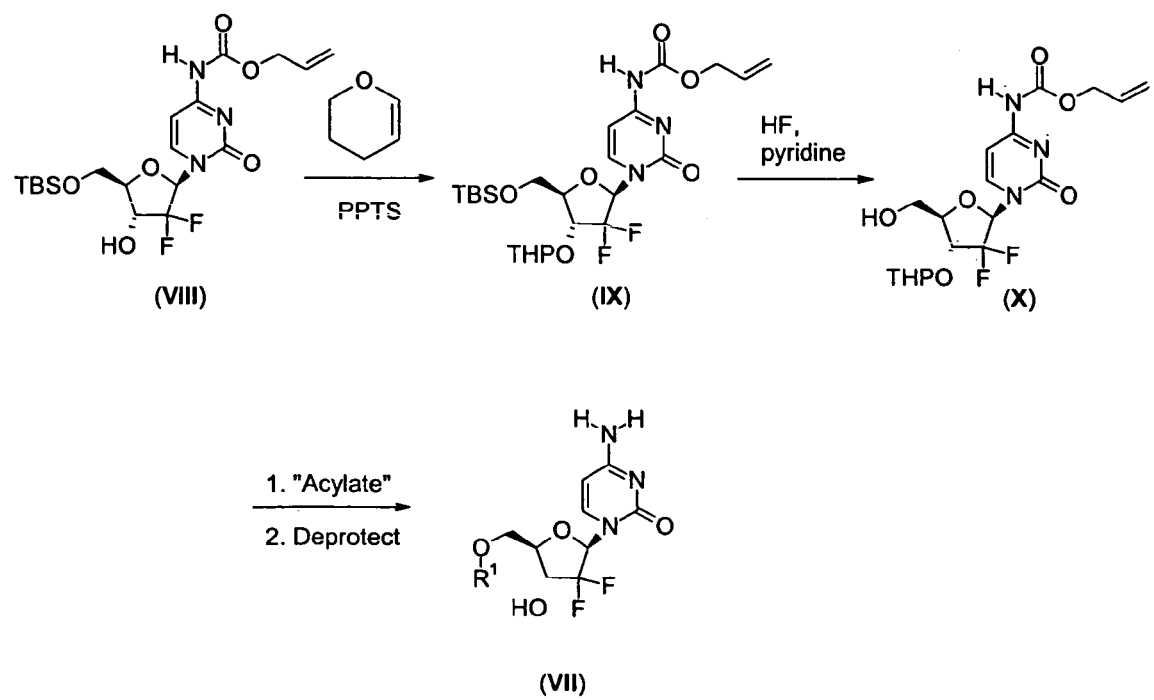
FIG. 3 illustrates a general synthetic route to 5'-substituted gemcitabine analogs.

FIG. 3 illustrates a general synthetic route to 5'-substituted gemcitabine analogs. The orthogonally protected nucleoside (IX) is derived from compound (VIII) by treatment with dihydropyran in the presence of an acid catalyst. Selective removal of the 5'-hydroxyl protecting group (e.g., HF, pyridine) to yield (X), followed by reaction with a suitable acylating, acyloxyalkylcarbonylating, oxycarbonylating or aminoacylating agent (or substituted variations thereof) and removal of the 3'-hydroxyl and nitrogen protecting groups provides the 5'-substituted gemcitabine analog (VII).

Figure 4:
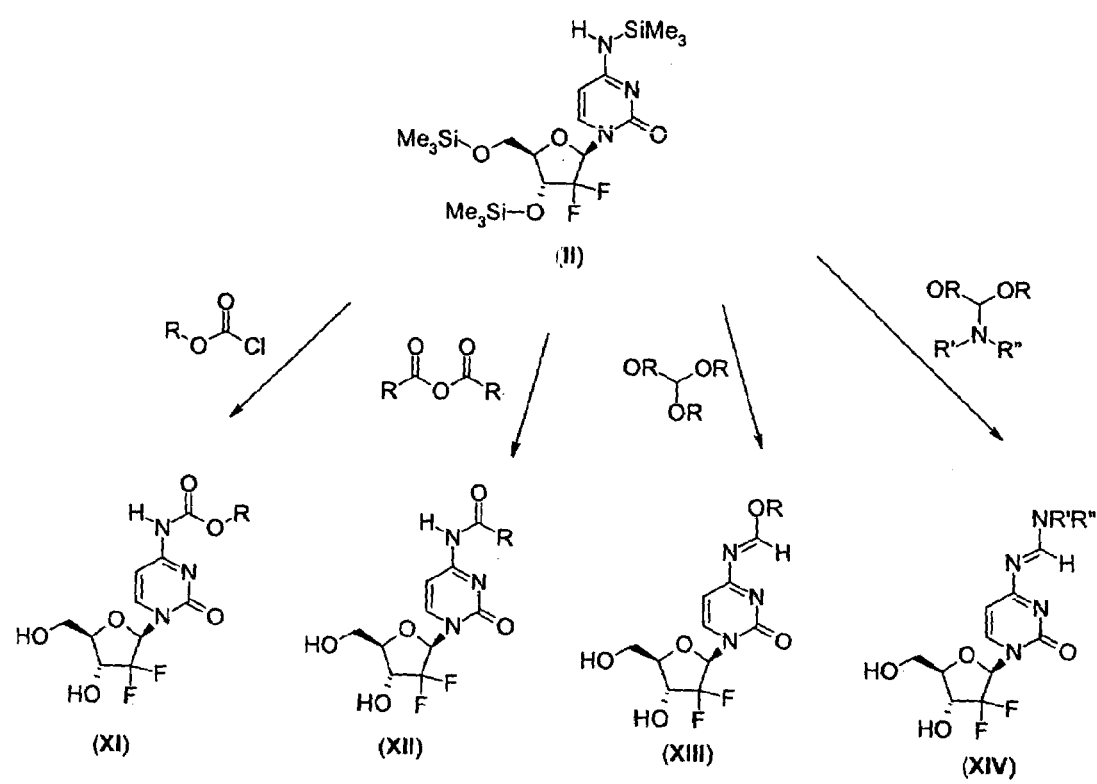
FIG. 4 illustrates some synthetic routes to N-4 substituted gemcitabine analogs.

FIG. 4 illustrates some synthetic routes to N-4 substituted gemcitabine analogs. The per-silylated nucleoside (II) is reacted with an alkoxycarbonyl derivative, an anhydride, an orthoester or a formamide acetal to provide carbamate (XI), amide (XII), imidate (XIII) and amidine (XIV) derivatives respectively. Carbamate derivatives (XI) may also be obtained via treatment of (II) with phosgene (or a phosgene equivalent) followed by reaction with an alcohol compound.

Figure 5:
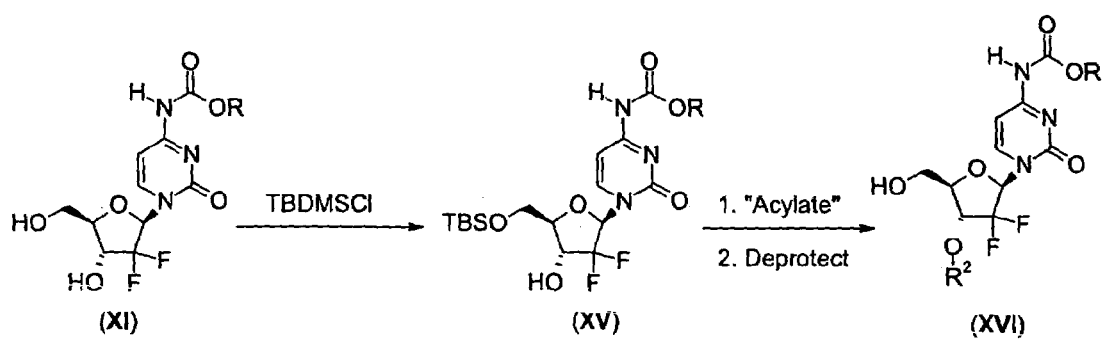
FIG. 5 illustrates a general synthetic route to 3'- and N-4 disubstituted gemcitabine analogs.

FIG. 5 illustrates a general synthetic route to gemcitabine analogs substituted at the 3' and N-4 positions. The carbamate nucleoside derivative (XI) is selectively protected at the 5'-hydroxyl (e.g., with tert-butyldimethylsilyl chloride, imidazole) to afford compound (XV), which may be further reacted with an appropriate acylating, acyloxyalkylcarbonylating, oxycarbonylating or aminoacylating agent (or substituted variations thereof) and then deprotected (e.g., trifluoroacetic acid or tetra-n-butyl ammonium fluoride) to yield the substituted gemcitabine analog (XVI).

Figure 6:
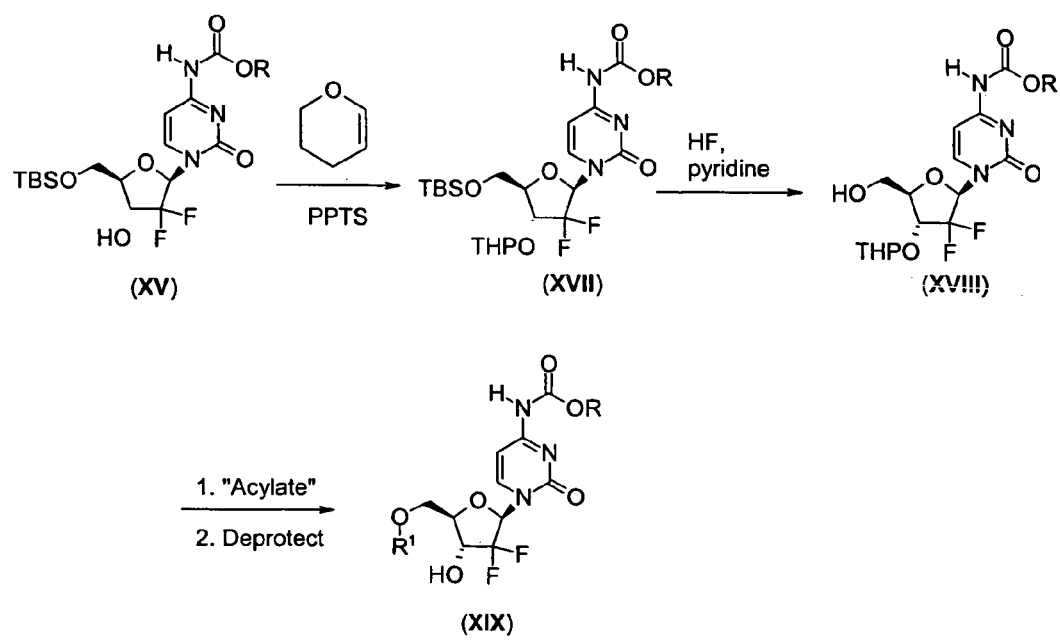
FIG. 6 illustrates a general synthetic route to 5'- and N-4 disubstituted gemcitabine analogs.

FIG. 6 illustrates a general synthetic route to gemcitabine analogs substituted at the 5' and N-4 positions. The orthogonally protected nucleoside derivative (XVII) is prepared from compound (XV) by treatment with dihydropyran in the presence of an acid catalyst. Selective removal of the 5'-hydroxyl protecting group (e.g., HF, pyridine) to yield (XVIII), followed by reaction with a suitable acylating, acyloxyalkylcarbonylating, oxycarbonylating or aminoacylating agent (or substituted variations thereof) and removal of the 3'-hydroxyl protecting group (e.g., gaseous HCl) provides the substituted gemcitabine analog (XIX).

Figure 7:
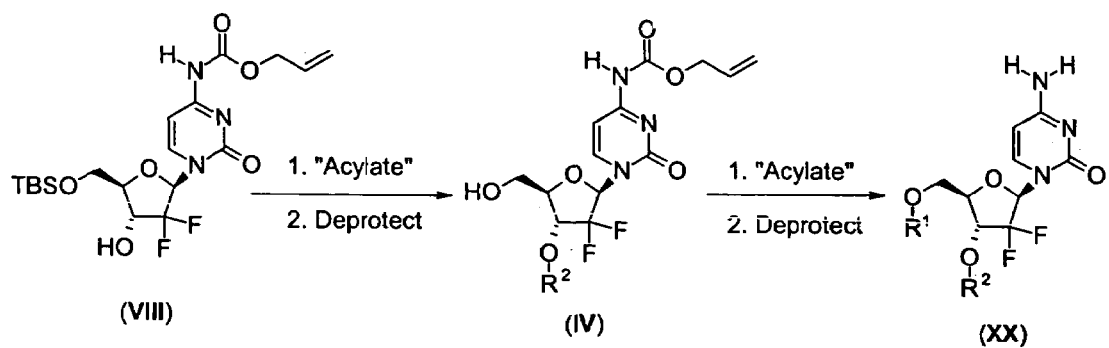
FIG. 7 illustrates a general synthetic route to 3'- and 5'-disubstituted gemcitabine analogs.

FIG. 7 illustrates a general synthetic route to gemcitabine analogs selectively substituted at the 3' and 5' positions. Compound (VIII) is reacted with a suitable acylating, acyloxyalkylcarbonylating, oxycarbonylating or aminoacylating agent (or substituted variations thereof) to provide compound (IV) after removal of the 5'-hydroxyl protecting group. Further treatment with a suitable acylating, acyloxyalkylcarbonylating, oxycarbonylating or aminoacylating agent (or substituted variations thereof) followed by removal of N-4 protecting group provides the substituted gemcitabine analog (XX).

Figure 8:
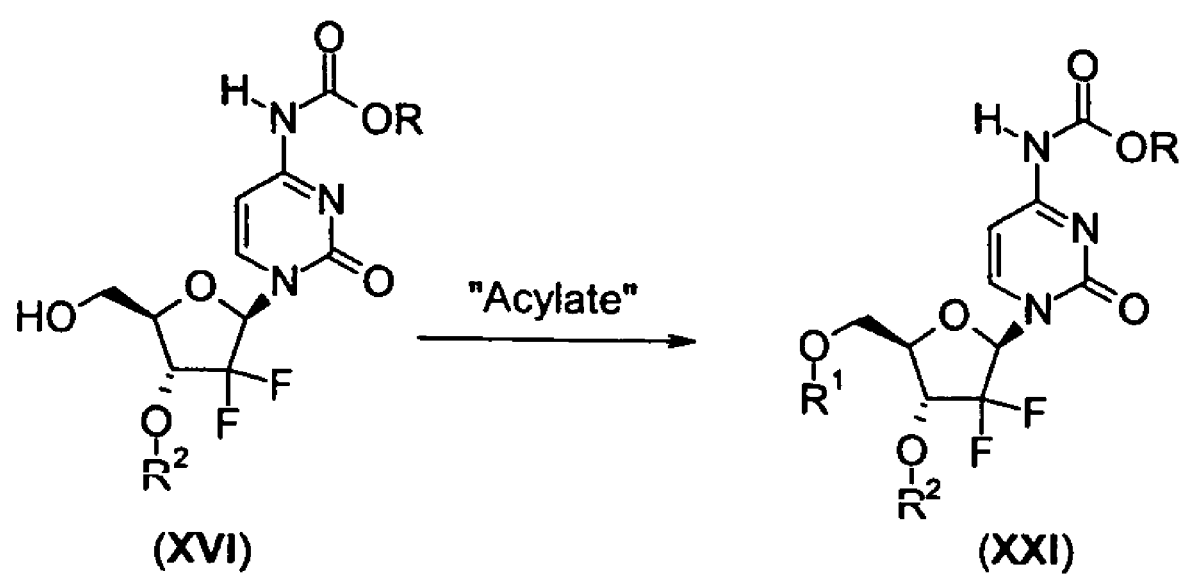
FIG. 8 illustrates a general synthetic route to trisubstituted gemcitabine analogs.

FIG. 8 illustrates a general synthetic route to gemcitabine analogs selectively substituted at the 3', 5' and N-4 positions. Disubstituted nucleoside derivative (XVI) is reacted with a suitable acylating, acyloxyalkylcarbonylating, oxycarbonylating or aminoacylating agent (or substituted variations thereof) to provide the triply substituted gemcitabine analog (XXI).

5.4 Therapeutic Uses

The compounds and pharmaceutical compositions thereof disclosed herein may be used to treat a variety of cancers. In a preferred embodiment, a compound and/or a pharmaceutical composition thereof is administered to a patient, preferably a human, suffering from at least one cancer.

Preferably, the types of cancer, which may be treated by administration of a compound and/or a pharmaceutical composition thereof include, but are not limited to, carcinomas of the lung, breast, ovary, stomach, pancreas, larynx, esophagus, testes, liver, parotid, bilary tract, colon, rectum, cervix, uterus, endometrium, kidney, bladder, prostrate, thyroid, squamous cell carcinomas, adenocarcinomas, small cell carcinomas, melanomas, gliomas, neuroblastomas, eminoma, tetratocarcinoma sarcomas (e.g., angiosarcoma, chondrosarcoma, fibrosarcoma, etc.), hematopoietic tumors of lymphoid linkage (e.g., leukemia, acute lymphocytic leukemia, acute lymphoblastic leukemia, T-cell lymphoma, B-cell lymphoma, Hodgkin's disease, Burkett's lymphoma, etc.), and hematopoietic tumors of mylenoid linkage. The compounds and/or pharmaceutical compositions thereof may also be used to treat viral infections (e.g., herpes virus, Epstein-Barr virus, hepatitis virus (including hepatitis B and C viruses), cytomegalovirus, papilloma virus, Sindbis virus, respiratory syncitial virus, adenovirus, HIV, human leukemia viruses, etc.).

Further, in certain embodiments, compounds and/or pharmaceutical compositions thereof are administered to a patient, preferably a human, as a preventative measure against the above diseases or disorders. Thus, the compounds and/or pharmaceutical compositions thereof may be administered as a preventative measure to a patient having a predisposition for any of the above diseases or disorders. Accordingly, the compounds and/or pharmaceutical compositions thereof may be used for the prevention of one disease or disorder and concurrently treating another (e.g., preventing cancer while treating a viral infection).

The suitability of the compounds and/or pharmaceutical compositions thereof in treating or preventing the various diseases or disorders listed above may be determined by methods described in the art. For example, screens developed to demonstrate the anti-tumor activity of oncolytic agents are disclosed in, e.g., Miller et al., *J. Med. Chem.* 1977, 20, 409-413; Sweeney et al., *Cancer Research,* 1978, 38, 2886-2891; and Weiss et al., *Semin. Oncol.* 1985, 12 (Suppl 4), 69-74. Screens developed to demonstrate the antiviral activity of experimental chemotherapeutic agents are disclosed in, e.g., Sudo et al., *J. Virol. Methods* 1994, 49, 169-178 and Nakashima et al., *J. Virol. Methods* 1989, 26, 319-329. Accordingly, it is well with the capability of those of skill in the art to assay and use the compounds and/or pharmaceutical compositions thereof to treat the above diseases or disorders.

5.5 Therapeutic/Prophylactic Administration

The compounds and/or pharmaceutical compositions thereof may be advantageously used in human medicine. As previously described in Section 5.4 above, compounds and/or pharmaceutical compositions thereof are useful for the treatment or prevention of various diseases or disorders.

When used to treat or prevent the above disease or disorders compounds and/or pharmaceutical compositions thereof may be administered or applied singly, in combination with other agents. The compounds and/or pharmaceutical compositions thereof may also be administered or applied singly, in combination with other pharmaceutically active agents, including other compounds.

The current disclosure provides methods of treatment and prophylaxis by administration to a patient of a therapeutically effective amount of a compound or pharmaceutical composition thereof. The patient may be an animal, is more preferably a mammal, and most preferably a human.

The present compounds and/or pharmaceutical compositions thereof, which comprise one or more compounds, are preferably administered orally. The compounds and/or pharmaceutical compositions thereof may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound and/or pharmaceutical composition thereof. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin.

In particularly preferred embodiments, the compounds and/or pharmaceutical compositions thereof can be delivered via sustained release systems, preferably oral sustained release systems. In one embodiment, a pump may be used (see Langer, supra; Sefton, 1987, *CRC Crit. Ref. Biomed. Eng.* 14:201; Saudek et al., 1989, *N. Engl. J. Med.* 321:574).

In another embodiment, polymeric materials can be used (see "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Langer et al., 1983, *J Macromol. Sci. Rev. Macromol Chem.* 23:61; Levy et al., 1985, *Science* 228: 190; During et al., 1989, *Ann. Neurol.* 25:351; Howard et al., 1989, *J. Neurosurg* 71:105). In a preferred embodiment, polymeric materials are used for oral sustained release delivery. Preferred polymers include sodium carboxymethylcellulose, hydroxypropylcellulose, hydroxypropylmethylcellulose and hydroxyethylcellulose (most preferred, hydroxypropylmethylcellulose). Other preferred cellulose ethers have been described (Alderman, *Int. J. Pharm. Tech. & Prod. Mfr.,* 1984, 5(3) 1-9). Factors affecting drug release are well known to the skilled artisan and have been described in the art (Bamba et al., *Int. J. Pharm.,* 1979, 2, 307).

In another embodiment, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In still another embodiment, osmotic delivery systems are used for oral sustained release administration (Verma et al., *Drug Dev. Ind. Pharm.,* 2000, 26:695-708). In a preferred embodiment, OROS™ osmotic devices are used for oral sustained release delivery devices (Theeuwes et al., U.S. Pat. No. 3,845,770; Theeuwes et al., U.S. Pat. No. 3,916,899).

In yet another embodiment, a controlled-release system can be placed in proximity of the target of the compounds and/or pharmaceutical compositions thereof, thus requiring only a fraction of the systemic dose (e.g., Goodson, in "Medical Applications of Controlled Release," supra, vol. 2, pp. 115-138 (1984)). Other controlled-release systems discussed in Langer, 1990, *Science* 249:1527-1533 may also be used.

The compounds and/or pharmaceutical compositions preferably provide gemcitabine upon in vivo administration to a patient. While not wishing to bound by theory, the promoiety or promoieties of the compounds may be cleaved either chemically and/or enzymatically. One or more enzymes present in the stomach, intestinal lumen, intestinal tissue, blood, liver, brain or any other suitable tissue of a mammal may enzymatically cleave the promoiety or promoieties of the compounds. When intravenously administered gemcitabine is known to cause gastrointestinal side-effects (e.g., nausea, vomiting, diarrhea) (see Green, *Semin Oncol.* 1996, 23(5 Suppl 10), 32-35). Accordingly, it is likely that gastrointestinal toxicity would be exacerbated by oral administration of the parent drug. For this reason it is preferred that gemcitabine prodrugs are absorbed across the gastrointestinal mucosa largely intact, before being converted to the active cytotoxic drug within the blood, plasma, liver, brain, tumor or any other suitable tissue of the subject.

If the promoiety or promoieties of the compounds are cleaved after absorption by the gastrointestinal tract, these gemcitabine analogs may have the opportunity to be absorbed into the systemic circulation from the large intestine. In this situation, the compounds and/or pharmaceutical compositions thereof may preferably be administered as sustained release systems. In a preferred embodiment, the compounds and/or pharmaceutical compositions thereof are delivered by oral sustained release administration. Delivery from a sustained release system may allow the drug to be administered in such a way that reduces the side-effect profile associated with high peak plasma concentrations of the drug following bolus injection. Preferably, in this embodiment, the compounds and/or pharmaceutical compositions thereof are administered no more than once per day.

5.6 Pharmaceutical Compositions

The present pharmaceutical compositions typically contain a therapeutically effective amount of one or more compounds, preferably in purified form, together with a suitable amount of a pharmaceutically acceptable vehicle, so as to provide the form for proper administration to a patient. When administered to a patient, the compounds and pharmaceutically acceptable vehicles are preferably sterile. Water is a preferred vehicle when the compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emu 1 sifying agents, or pH buffering agents. In addition, auxiliary, stabilizing, thickening, lubricating and coloring agents may be used.

Pharmaceutical compositions comprising a compound may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds into preparations which can be used pharmaceutically. Proper formulation is dependent upon the route of administration chosen.

The present pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 19th Edition, 1995).

For topical administration a compound may be formulated as solutions, gels, ointments, creams, suspensions, etc. as is well-known in the art. For transmucosal administration, penetrants appropriate to the barrier to be permeated are used in the formulation. Such penetrants are generally known in the art. Systemic formulations include those designed for administration by injection, e.g., subcutaneous, intravenous, intramuscular, intrathecal or intraperitoneal injection, as well as those designed for transdermal, transmucosal, oral or pulmonary administration. Systemic formulations may be made in combination with a further active agent that improves mucociliary clearance of airway mucus or reduces mucous viscosity. These active agents include, but are not limited to, sodium channel blockers, antibiotics, N-acetyl cysteine, homocysteine and phospholipids.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optional agents, for example, sweetening agents such as fructose, aspartame or saccharin; flavoring agents such as peppermint, oil of wintergreen, or cherry coloring agents and preserving agents, to provide a pharmaceutically palatable preparation. Moreover, when in tablet or pill form, the pharmaceutical compositions may be coated to delay disintegration and absorption in the gastrointestinal tract, thereby providing a sustained action over an extended period of time. Selectively permeable membranes surrounding an osmotically active driving compound are also suitable for orally administered compounds. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmnaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5.0 mM to about 50.0 mM), etc. Additionally, flavoring agents, preservatives, coloring agents, bile salts, acylcarnitines and the like may be added.

For buccal administration, the pharmaceutical compositions may take the form of tablets, lozenges, etc. formulated in conventional manner.

In addition to the formulations described previously, a compound may also be formulated as a depot preparation. Such long acting formulations may be administered by implantation (for example subcutaneously or intramuscularly) or by intramuscular injection. Thus, for example, a compound may be formulated with suitable polymeric or hydrophobic materials (for example, as an emulsion in an acceptable oil) or ion exchange resins, or as sparingly soluble derivatives, for example, as a sparingly soluble salt.

When a compound is acidic or basic, it may be included in any of the above-described formulations as the free acid or free base, a pharmaceutically acceptable salt, a solvate or hydrate. Pharmaceutically acceptable salts substantially retain the activity of the free acid or base, may be prepared by reaction with bases or acids and tend to be more soluble in aqueous and other protic solvents than the corresponding free acid or base form.

5.7 Therapeutic Doses

A compound and/or pharmaceutical composition thereof, will generally be used in an amount effective to achieve the intended purpose. For use to treat or prevent the above diseases or disorders the compounds and/or pharmaceutical compositions thereof, are administered or applied in a therapeutically effective amount.

The amount of a compound and/or pharmaceutical composition thereof that will be effective in the treatment of a particular disorder or condition disclosed herein will depend on the nature of the disorder or condition, and can be determined by standard clinical techniques known in the art. In addition, in vitro or in vivo assays may optionally be employed to help identify optimal dosage ranges. The amount of a compound and/or pharmaceutical composition thereof administered will, of course, be dependent on, among other factors, the subject being treated, the weight of the subject, the severity of the affliction, the manner of administration and the judgment of the prescribing physician.

For treatment of the labeled indications of locally advanced or metastatic non-small cell lung cancer or pancreatic adenocarcinoma, gemcitabine is typically administered by intravenous infusion at a dose of 1000 mg/m$^2$ over 30 minutes (i.e. ~30 mg/m$^2$/min) once weekly. Intravenous dosing schedules frequently follow 4-week cycles where drug is administered weekly for 3 consecutive weeks followed by a rest from treatment. Studies in preclinical animal models as well several clinical studies in patients with hematological and solid tumors have documented that prolonged, low-dose infusion of gemcitabine can show superior antitumor activity relative to bolus or shorter-term infusion schedules (for example, see Veerman et al., *Cancer Chemother. Pharmacol.* 1996, 38, 335-342; Tempero et al., *J. Clin. Oncol.* 2003, 21, 3402-3408; Gandhi et al., *J. Clin. Oncol.* 2002, 20, 665-673; Rizzieri et al., *J. Clin. Oncol.* 2002, 20, 674-679; Patel et al., *J. Clin. Oncol.* 2001, 19, 3483-3489; Maurel et al., *Anti-Cancer Drugs* 2001, 12, 713-717; Akrivakis et al., Anti-Cancer Drugs 199, 10, 525-531). Doses of 10 mg/m$^2$/min for up to 12 hours have been reported to be tolerated in patients. Long-term intravenous administration of gemcitabine itself is inconvenient for patients and requires close supervision by medical staff. Oral dosage of gemcitabine prodrugs of the type disclosed herein offer considerable advantages in providing gemcitabine exposure over prolonged time periods, while minimizing acute side effects associated with gastrointestinal toxicity of the drug.

For example, the dosage may be delivered in a pharmaceutical composition by a single administration, by multiple applications or controlled release. In one embodiment, the compounds are delivered by oral sustained release administration. Preferably, in this embodiment, the compounds are administered no more than once per day. Dosing may be repeated intermittently, may be provided alone or in combination with other drugs and may continue as long as required for effective treatment of the disease state or disorder.

Suitable dosage ranges for oral administration are dependent on the potency of gemcitabine in the particular indication of interest as well as the prodrug bioavailability, but are generally about 100 mg-eq/m$^2$/day to about 7000 mg-eq/m$^2$ of a compound. Dosage ranges may be readily determined by methods known to the artisan of ordinary skill.

The compounds are preferably assayed in vitro and in vivo, for the desired therapeutic or prophylactic activity, prior to use in humans. For example, in vitro assays can be used to determine whether administration of a specific compound or a combination of compounds is preferred. The compounds may also be demonstrated to be effective and safe using animal model systems.

Preferably, a therapeutically effective dose of a compound and/or pharmaceutical composition thereof described herein will provide therapeutic benefit without causing substantial toxicity. Toxicity of compounds and/or pharmaceutical compositions thereof may be determined using standard pharmaceutical procedures and may be readily ascertained by the skilled artisan. The dose ratio between toxic and therapeutic effect is the therapeutic index. A compound and/or pharmaceutical composition thereof will preferably exhibit particularly high therapeutic indices in treating disease and disorders. The dosage of a compound and/or pharmaceutical composition thereof described herein will preferably be within a range of circulating concentrations that include an effective dose with minimal toxicity. Gemcitabine exerts toxic effects on the gastrointestinal tract via accumulation as the cytotoxic triphosphate metabolite within enterocytes. Oral administration of a gemcitabine prodrug that is substantially stable within enterocytes, but which is capable of conversion to the parent drug following absorption provides a mechanism for reducing intestinal cell exposure to gemcitabine. For example, as described in Example 63 below, (see Section 6.63) oral administration to mice of β-1-(4-ethoxycarbonylamino-2-oxo-1H-pyrimidin-1-yl)-2-deoxy-2,2-difluororibose (11) resulted in a greater than 5-fold reduction in the ratio of the maximal intestinal tissue gemcitabine concentration to maximal plasma concentration of gemcitabine ($C_{max}$) liberated from the prodrug, relative to oral administration of gemcitabine itself. Data is also presented in Section 6.63 demonstrating that prodrugs disclosed herein provided substantial increases in oral bioavailability as gemcitabine when compared with oral dosing of gemcitabine itself.

5.8 Combination Therapy

In certain embodiments of the present disclosure, the compounds and/or pharmaceutical compositions thereof can be used in combination therapy with at least one other therapeutic agent. The compound and/or pharmaceutical composition thereof and the therapeutic agent can act additively or, more preferably, synergistically. In a preferred embodiment, a compound and/or a pharmaceutical composition thereof is administered concurrently with the administration of another therapeutic agent. In another embodiment, a compound and/or pharmaceutical composition thereof is administered prior or subsequent to administration of another therapeutic agent.

In particular, in one preferred embodiment, the compounds and/or pharmaceutical compositions thereof can be used in combination therapy with other chemotherapeutic agents (e.g., alkylating agents (e.g., nitrogen mustards (e.g., cyclophosphamide, ifosfamide, mechlorethamine, melphalen, chlorambucil, hexamethylmelamine, thiotepa), alkyl sulfonates (e.g., busulfan), nitrosoureas, triazines) antimetabolites (e.g., folic acid analogs, pyrimidine analogs (e.g., fluorouracil, floxuridine, cytosine arabinoside, etc.), purine analogs (e.g., mercaptopurine, thiogunaine, pentostatin, etc.), natural products (e.g., vinblastine, vincristine, etoposide, tertiposide, dactinomycin, daunorubicin, doxurubicin, bleomycin, mithrmycin, mitomycin C, L-asparaginase, interferon alpha), platinum coordination complexes (e.g., cis-platinum, carboplatin, etc.), mitoxantrone, hydroxyurea, procarbazine, hormones and antagonists (e.g., prednisone, hydroxyprogesterone caproate, medroxyprogesterone acetate, megestrol acetate, diethylstilbestrol, ethinyl estradiol, tamoxifen, testosterone propionate, fluoxymesterone, flutamide, leuprolide, etc.), anti-angiogenesis agents or inhibitors (e.g., angiostatin, retinoic acids and paclitaxel, estradiol derivatives, thiazolopyrimidine derivatives, etc.), apoptosis prevention agents and radiation therapy.

6. EXAMPLES

The invention is further defined by reference to the following examples, which describe in detail, preparation of compounds and methods for assaying for biological activity. It will be apparent to those skilled in the art that many modifications, both to materials and methods, may be practiced without departing from the scope of the invention.

In the examples below, the following abbreviations have the following meanings. If an abbreviation is not defined, it has its generally accepted meaning.

| | |
|---|---|
| Atm = | atmosphere |
| Boc = | tert-butyloxycarbonyl |
| Bzl = | benzyl |
| Cbz = | carbobenzyloxy |
| DCC = | dicyclohexylcarbodiimide |
| DMAP = | 4-N,N-dimethylaminopyridine |
| DMF = | N,N-dimethylformamide |
| DMSO = | dimethylsulfoxide |
| Fmoc = | 9-fluorenylmethyloxycarbonyl |
| g = | gram |
| h = | hour |
| L = | liter |
| LC/MS = | liquid chromatography/mass spectroscopy |
| M = | molar |
| min = | minute |
| mL = | milliliter |
| mmol = | millimoles |
| NHS = | N-hydroxysuccinimide |
| PBS = | phosphate buffered saline |
| THF = | tetrahydrofuran |
| TFA = | trifluoroacetic acid |
| TMS = | trimethylsilyl |
| μL = | microliter |
| μM = | micromolar |
| v/v = | volume to volume |

6.1 Example 1

β-1-(4-Allyloxycarbonylamino-2-oxo-1H-pyrimidin-1-yl)-2-deoxy-2,2-difluororibose (1)

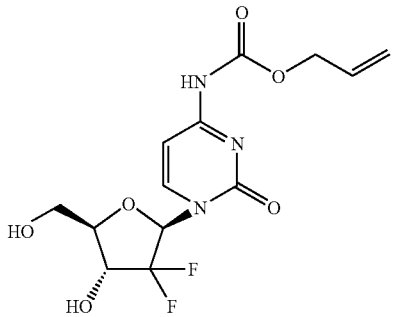

To a suspension of β-1-(4-amino-2-oxo-1H-pyrimidin-1-yl)-2-deoxy-2,2-difluororibose. HCl (3.0 g, 10.0 mmol, 1.0 eq.) in anhydrous pyridine (36 mL) under N$_2$ was added diisopropylethylamine (3.48 mL, 20.0 mmol, 2.0 eq.), resulting in a homogenous solution. This solution was cooled to 0° C., and chlorotrimethylsilane (5.1 mL, 40.0 mmol, 4.0 eq.) was added. The solution was warmed to room temperature following completion of the addition of chlorotrimethylsilane. After 1 hour at room temperature, allyl 1-benzotriazolyl carbonate (4.4 g, 20.0 mmol, 2.0 eq.) was added, and the solution was stirred overnight at room temperature. After overnight stirring, additional allyl 1-benzotriazolyl carbonate (2.2 g, 10.0 mmol, 1.0 eq.) was added, and the solution was stirred an additional 24 hours at room temperature. After this time, 50 mL 10% aqueous sodium bicarbonate was added and the solution was stirred at room temperature for 3 hours. Water (30 mL) was added, and this solution was extracted four times with dichloromethane. The organic layers were combined, dried over Na$_2$SO$_4$ and concentrated to yield a viscous oil. This oil was dissolved in 8 mL dichloromethane and treated with 6 mL trifluoroacetic acid at room temperature for 1 hour. This solution was concentrated, leaving a viscous oil that was purified by chromatography over silica gel (solvent gradient=1:4 hexanes: ethyl acetate to 100% ethyl acetate) to provide β-1-(4-allyloxycarbonylamino-2-oxo-1H-pyrimidin-1-yl)-2-deoxy-2,2-difluororibose (1) (3.42 g, 98%) as a white powder.

$^1$H NMR (CD$_3$OD, 400 MHz): 3.80 (m, 1H), 3.96 (m, 2H), 4.29 (m, 1H), 4.69 (d, J=5.6 Hz, 2H), 5.25 (m, 1H), 5.40 (m, 1H), 5.98 (m, 1H), 6.23 (t, J=7.2 Hz, 1H), 7.34 (d, J=7.6 Hz, 1H), 8.32 (d, J=7.6 Hz, 1H). MS (ESI) m/z 348.25 (M+H)$^+$, 346.28 (M−H)$^−$.

6.2 Example 2

β-1-(4-Benzyloxycarbonylamino-2-oxo-1H-pyrimidin-1-yl)-2-deoxy-2,2-difluororibose (2)

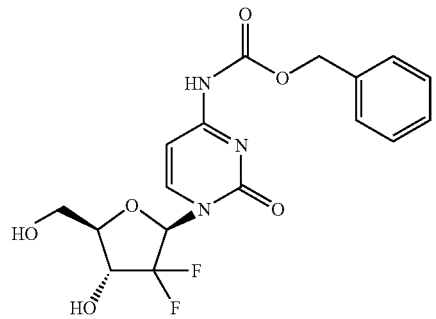

Chlorotrimethylsilane (507 μL, 4.0 mmol, 4.0 eq.) was added dropwise to a solution of β-1-(4-amino-2-oxo-1H-pyrimidin-1-yl)-2-deoxy-2,2-difluororibose. HCl (300 mg, 1.0 mmol, 1.0 eq.) and diisopropylethylamine (261 μL, 1.5 mmol, 1.5 eq.) in 10 mL pyridine at room temperature. After stirring 1 hour at room temperature, benzyl chloroformate (171 μL, 1.2 mmol, 1.2 eq.) was added, and the solution was stirred overnight at room temperature. After overnight stirring, additional diisopropylethylamine (0.75 eq.) and benzyl chloroformate (0.6 eq.) were added, and the solution was again stirred overnight at room temperature. 10% aqueous NaHCO$_3$ (20 mL) was added, and the solution was stirred 1 hour at room temperature. Water (10 mL) was added, and the solution was extracted with dichloromethane. The dichloromethane layers were combined and concentrated to remove the pyridine, leaving a viscous oil, which was dissolved in 6 mL dichloromethane and treated with 4 mL trifluoroacetic acid for 15 minutes at room temperature. This solution was concentrated to yield a viscous oil, which was dissolved in 1:1 acetonitrile: water, filtered and purified by preparative LC-MS to provide β-1-(4-benzyloxycarbonylamino-2-oxo-1H-pyrimidin-1-yl)-2-deoxy-2,2-difluororibose (2) (108 mg, 27%) as a white powder. $^1$H NMR (CD$_3$OD, 400 MHz): 3.80 (m, 1H), 3.96 (m, 2H), 4.29 (m, 1H), 5.22 (s, 2H), 6.23 (t, J=7.6 Hz, 1H), 7.30-7.42 (m, 6H), 8.31 (d, J=7.2 Hz, 1H). MS (ESI) m/z 398.17 (M+H)$^+$, 396.21 (M−H)$^−$.

6.3 Example 3

β-1-(4-Amino-2-oxo-1H-pyrimidin-1-yl)-3-O-(L-valinyl)-2-deoxy-2,2-difluororibose (3)

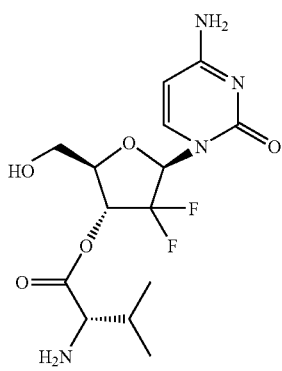

β-1-(4-Amino-2-oxo-1H-pyrimidin-1-yl)-5-O-(L-valinyl)-2-deoxy-2,2-difluororibose (4)

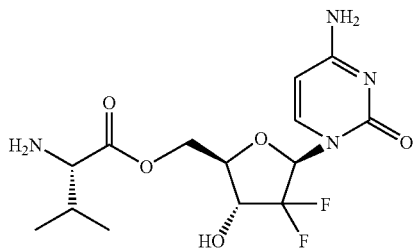

The above 2 compounds were each isolated by preparative HPLC chromatography from the following reaction. N-tert-Butyloxycarbonyl-L-valine (350 mg, 1.6 mmol, 2.4 eq.) was dissolved in 10 mL dichloromethane. To this solution was added dicyclohexylcarbodiimide (170 mg, 0.8 mmol, 1.2 eq.). Shortly after the addition of dicyclohexylcarbodiimide, a white precipitate formed. This suspension was stirred at room temperature for 2 hours, then filtered directly into a separate flask containing β-1-(4-alloxycarbonylamino-2-oxo-1H-pyrimidin-1-yl)-2-deoxy-2,2-difluororibose (232 mg, 0.67 mmol, 1.0 eq.) and 4-dimethylaminopyridine (10 mg, 0.07 mmol, 0.1 eq.) dissolved in 10 mL dichloromethane. This solution was stirred overnight at room temperature, then the crude product was washed with 5 mL saturated sodium bicarbonate solution. The dichloromethane solution was dried over sodium sulfate and concentrated to yield 220 mg of a viscous oil. The oil was dissolved in 15 mL tetrahydrofuran, then triphenylphosphine (21 mg, 0.08 mmol, 0.2 eq.), ethanolamine (49 μL, 0.8 mmol, 2.0 eq.), and formic acid (61 μL, 1.6 mmol, 4.0 eq.) were added, the solution being degassed by bubbling under $N_2$ for 2 minutes. Tetrakis(triphenylphosphine)palladium(0) (46 mg, 0.04 mmol, 0.1 eq.) was added, and the solution was stirred at room temperature for 1 hour. The reaction solution was concentrated to yield a viscous oil, which was dissolved in 6 mL dichloromethane and treated with 6 mL trifluoroacetic acid at room temperature for 1 hour. The reaction was concentrated to yield a viscous oil, which was dissolved in 1:1 acetonitrile: water, filtered and purified by preparative HPLC.

β-1-(4-amino-2-oxo-1H-pyrimidin-1-yl)-3-O-(L-valinyl)-2-deoxy-2,2-difluororibose (3) (5 mg, 3.4%, white powder): $^1$H NMR (CD$_3$OD, 400 MHz): 1.19 (d, J=7.2 Hz, 6H), 2.37 (m, 1H), 3.80 (d, J=12.4 Hz, 1H), 3.97(d, J=12.4 Hz, 1H), 4.16(d, J=4.4 Hz, 1H), 4.35(m, 1H), 5.62 (m, 1H), 6.17 (d, J=8.0 Hz, 1H), 6.30 (t, J=8.0 Hz, 1H), 8.13 (d, J=8.0 Hz, 1H). MS (ESI) m/z 363.31 (M+H)$^+$, 361.43 (M−H)$^−$.

β-1-(4-amino-2-oxo-1H-pyrimidin-1-yl)-5-O-(L-valinyl)-2-deoxy-2,2-difluororibose (4) (45 mg, 31%, white powder): $^1$H NMR (CD$_3$OD, 400 MHz): 1.07 (d, J=7.2 Hz, 6H), 2.32 (m, 1H), 4.03(dd, J1=4.4 Hz, J2=1.2 Hz, 1H), 4.21 (m, 1H), 4.31 (dd, J1=18.8, J2=10.4, 1H), 4.62 (d, J=4.8 Hz, 2H), 6.12 (d, J=8.0 Hz, 1H), 6.16 (J=8.0 Hz, 1H), 7.85 (d, J=8.0 Hz, 1H). MS (ESI) m/z 363.30 (M+H)$^+$, 361.46 (M−H)$^−$.

6.4 Example 4

β-1-(4-Amino-2-oxo-1H-pyrimidin-1-yl)-3-O-(L-tert-butylglycinyl)-2-deoxy-2,2-difluororibose (5)

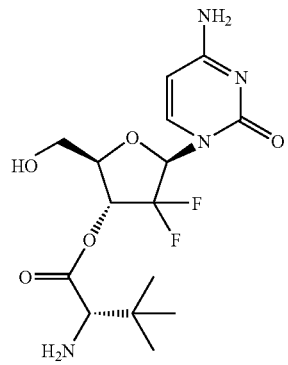

β-1-(4-Amino-2-oxo-1H-pyrimidin-1-yl)-5-O-(L-tert-butylglycinyl)-2-deoxy-2,2-difluororibose (6)

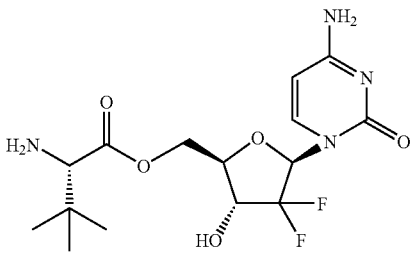

The above compounds were prepared in a similar manner as previously described substituting N-tert-butyloxycarbonyl-L-tert-butylglycine for N-tert-butyloxycarbonyl-L-valine.

β-1-(4-amino-2-oxo-1H-pyrimidin-1-yl)-3-O-(L-tert-butylglycinyl)-2-deoxy-2,2-difluororibose (5). $^1$H NMR (CD$_3$OD, 400 MHz): 1.15(s, 9H), 3.80 (dd, J1=12.4 Hz, J2=3.2 Hz, 1H), 3.97(dd, J1=12.4 Hz, J2=3.2 Hz, 1H), 4.05(s, 1H), 4.36(m, 1H), 5.64 (dd, J1=19.2 Hz, J2=7.6 Hz, 1H), 6.14 (d, J=8.0 Hz, 1H), 6.31(t, J=8.0 Hz, 1H), 8.09 (d, J=8.0 Hz, 1H). MS (ESI) m/z 377.22 (M+H)⁺, 375.33 (M−H)⁻.

β-1-(4-amino-2-oxo-1H-pyrimidin-1-yl)-5-O-(L-tert-butylglycinyl)-2-deoxy-2,2-difluororibose (6). ¹H NMR (CD₃OD, 400 MHz): 1.12(s, 9H), 3.90 (s, 1H), 4.21(m, 1H), 4.26(m, 1H), 6.60 (d, J=4.8 Hz, 2H), 6.11 (d, J=8.0 Hz, 1H), 6.17 (t, J=8.0 Hz, 1H), 7.83 (d, J=8.0 Hz, 1H). MS (ESI) m/z 377.30 (M+H)⁺, 375.40 (M−H)⁻.

6.5 Example 5

β-1-(4-Amino-2-oxo-1H-pyrimidin-1-yl)-3-O-(L-phenylalaninyl)-2-deoxy-2,2-difluororibose (7)

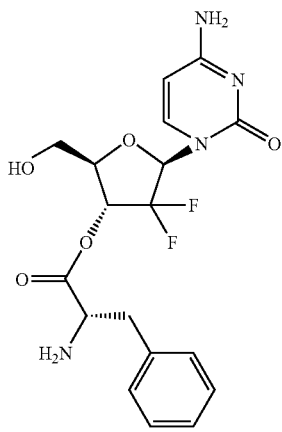

β-1-(4-Amino-2-oxo-1H-pyrimidin-1-yl)-5-O-(L-phenylalaninyl)-2-deoxy-2,2-difluororibose (8)

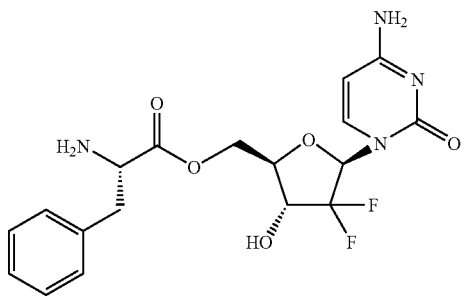

The above compounds were prepared in a similar manner as previously described substituting N-tert-butyloxycarbonyl-L-phenylalanine for N-tert-butyloxycarbonyl-L-valine.

β-1-(4-amino-2-oxo-1H-pyrimidin-1-yl)-3-O-(L-phenylalaninyl)-2-deoxy-2,2-difluororibose (7). ¹H NMR (CD₃OD, 400 MHz): 3.30 (m, 2H), 3.61 (dd, J=12.4 Hz, J=3.2 Hz, 1H), 3.83 (dd, J=12.4 Hz, J=3.2 Hz, 1H), 4.00 (m, 1H), 4.57(t, J=7.6 Hz, 1H), 5.50 (m, 1H), 6.11 (d, J=8.0 Hz, 1H), 6.20 (t, J=8.0 Hz, 1H), 7.37 (m, 5H), 8.03 (d, J=8.0 Hz, 1H). MS (ESI) m/z 411.26 (M+H)⁺, 409.33 (M−H)⁻.

β-1-(4-amino-2-oxo-1H-pyrimidin-1-yl)-5-O-(L-phenylalaninyl)-2-deoxy-2,2-difluororibose (8). ¹H NMR (CD₃OD, 400 MHz): 3.23 (m, 2H), 4.12 (m, 2H), 4.26 (m, 1H), 4.42 (t, J=6.8 Hz, 1H), 4.49 (dd, J=12.4 Hz, J=5.6 Hz, 1H), 4.58 (dd, J=12.0 Hz, J=2.4 Hz, 1H), 6.13 (m, 2H), 7.31 (m, 5H), 7.74 (d, J=8.0 Hz, 1H). MS (ESI) m/z 411.20 (M+H)⁺, 409.30 (M−H)⁻.

6.6: Example 6

β-1-(4-Amino-2-oxo-1H-pyrimidin-1-yl)-3-O-(L-isoleucinyl)-2-deoxy-2,2-difluororibose (9)

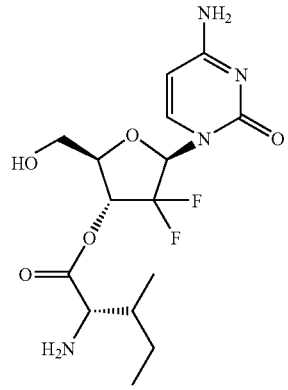

β-1-(4-Amino-2-oxo-1H-pyrimidin-1-yl)-5-O-(L-isoleucinyl)-2-deoxy-2,2-difluororibose (10)

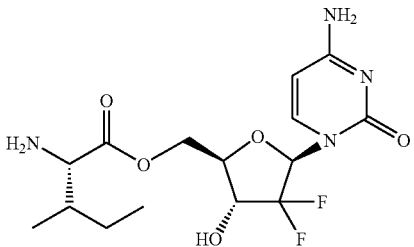

The above compounds were prepared in a similar manner as previously described substituting N-tert-butyloxycarbonyl-L-isoleucine for N-tert-butyloxycarbonyl-L-valine.

β-1-(4-amino-2-oxo-1H-pyrimidin-1-yl)-3-O-(L-isoleucinyl)-2-deoxy-2,2-difluororibose (9): ¹H NMR (CD₃OD, 400 MHz): 1.03 (t, J=7.2 Hz, 3H), 1.07 (d, J=6.4 Hz, 3H), 1.40 (m, 1H), 1.55 (m, 1H), 2.06 (m, 1H), 3.79 (dd, J=12.4 Hz, J=3.2 Hz, 1H), 3.96 (dd, J=12.8 Hz, J=2.8 Hz, 1H), 3.24 (d, J=4.00 Hz, 1H), 4.24 (d, J=4.0 Hz, 1H), 4.35 (m, 1H), 5.62 (dd, J=18.8 Hz, J=7.6 Hz, 1H), 6.16 (d, J=8.0 Hz, 1H), 6.31 (t, J=8.0 Hz, 1H), 8.12 (d, J=8.0 Hz, 1H). MS (ESI) m/z 377.30 (M+H)⁺, 375.22 (M−H)⁻.

β-1-(4-amino-2-oxo-1H-pyrimidin-1-yl)-5-O-(L-isoleucinyl)-2-deoxy-2,2-difluororibose (10): ¹H NMR (CD₃OD, 400 MHz): 0.98 (t, J=7.6 Hz, 3H), 1.02 (d, J=6.8 Hz, 3H), 1.36 (m, 1H), 1.53 (m, 1H), 2.00 (m, 1H), 4.11 (d, J=4 Hz, 1H), 4.21 (m, 1H), 4.32 (dd, J=10.0 Hz, J=7.6 Hz, 1H), 4.60 (m, 2H), 6.18 (m, 2H), 7.89 (d, J=8.0 Hz, 1H). MS (ESI) m/z 377.30 (M+H)⁺, 375.40 (M−H)⁻.

6.7 Example 7

β-1-(4-Ethoxycarbonylamino-2-oxo-1H-pyrimidin-1-yl)-2-deoxy-2,2-difluororibose (11)

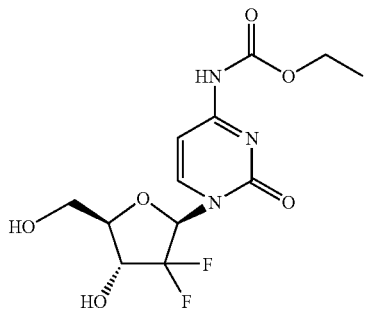

β-1-(4-Amino-2-oxo-1H-pyrimidin-1-yl)-2-deoxy-2,2-difluororibose. HCl (500 mg, 1.67 mmol, 1.0 eq.) and diisopropylethylamine (291 μL, 1.67 mmol, 1.0 eq.) were dissolved in 8 mL pyridine, and the solution was cooled to 0° C. Chlorotrimethylsilane (849 μL, 6.7 mmol, 4.0 eq.) was added and the solution was stirred from 0° C. to room temperature over 2 hours. Ethylchloroformate (206 μL, 2.17 mmol, 1.3 eq.) was then added, and the solution was stirred at room temperature overnight. 10% aqueous sodium bicarbonate (10 mL) was added, and the solution was stirred vigorously at room temperature for 3 hours. Water (10 mL) was added, and the solution was extracted with dichloromethane. The organic layers were combined, dried over $Na_2SO_4$, and concentrated, providing a viscous oil. This oil was dissolved in 4 mL dichloromethane and treated with 2 mL trifluoroacetic acid for 1 hour at room temperature. The solution was concentrated, yielding a viscous oil, which was purified by chromatography over silica gel (solvent gradient=2:3 hexanes:ethyl acetate to 100% ethyl acetate) to provide β-1-(4-ethoxycarbonylamino-2-oxo-1H-pyrimidin-1-yl)-2-deoxy-2,2-difluororibose (11) (480 mg, 86%) as a white powder. $^1$H NMR ($CD_3OD$, 400 MHz): 1.36 (t, J=6.8 Hz, 3H), 3.80 (m, 1H), 3.98 (m, 2H), 4.21-4.39 (m, 3H), 6.22 (t, J=7.2 Hz, 1H), 7.21 (d, J=8.0 Hz, 1H), 8.36 (d, J=8.0 Hz, 1H). MS (ESI) m/z 336.20 (M+H)$^+$, 334.19 (M−H)$^−$.

6.9 Example 9

β-1-(4-Ethoxycarbonylamino-2-oxo-1H-pyrimidin-1-yl)-5-O-(tert-butyldimethylsilyl)-2-deoxy-2,2-difluororibose (12)

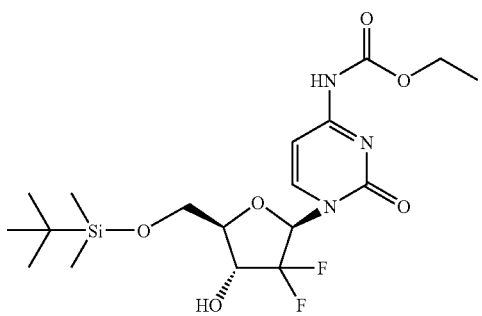

β-1-(4-Ethoxycarbonylamino-2-oxo-1H-pyrimidin-1-yl)-2-deoxy-2,2-difluororibose (240 mg, 0.72 mmol, 1.0 eq.) was dissolved in 5 mL acetonitrile and the solution was cooled to 0° C. Imidazole (97 mg, 1.43 mmol, 2.0 eq.) and tert-butyldimethylsilyl chloride (216 mg, 1.43 mmol, 2.0 eq.) were added, and the reaction was stirred from 0° C. to room temperature overnight. The reaction was filtered and concentrated to provide a viscous oil, which was purified by chromatography over silica gel (solvent gradient=3:2 hexanes:ethyl acetate to 3:7 hexanes:ethyl acetate) to yield β-1-(4-ethoxycarbonylamino-2-oxo-1H-pyrimidin-1-yl)-5-O-(tert-butyldimethylsilyl)-2-deoxy-2,2-difluororibose (12) (180 mg, 55%) as a white solid.

$^1$H NMR ($CDCl_3$, 400 MHz): 0.00 (s, 6H). 0.80 (s, 9H), 1.20 (t, J=7.2 Hz, 3H), 3.78 (m, 1H), 3.96 (m, 2H), 4.12 (m, 2H), 4.23 (m, 1H), 6.22 (m, 1H), 7.10 (m, 1H), 8.00 (d, 1H). MS (ESI) m/z 450.26 (M+H)$^+$, 448.26 (M−H)$^−$.

6.10 Example 10

β-1-(4-Ethoxycarbonylamino-2-oxo-1H-pyrimidin-1-yl)-3-O-(N-tert-butyloxycarbonyl-L-valinyl)-5-O-(tert-butyldimethylsilyl)-2-deoxy-2,2-difluororibose (13)

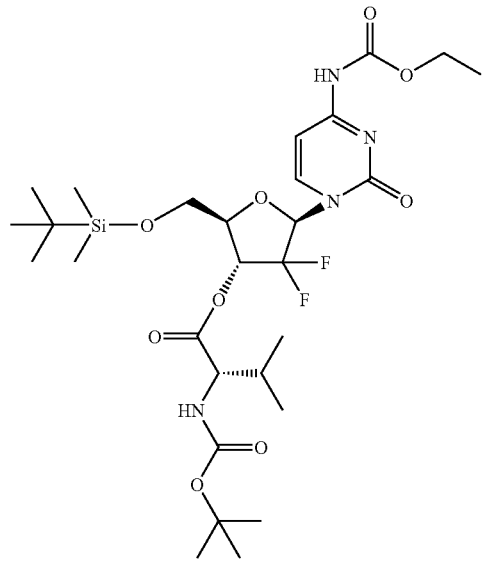

N-tert-Butyloxycarbonyl-L-valine (35 mg, 0.16 mmol, 2.4 eq.) was dissolved in 1 mL dichloromethane. To this solution was added dicyclohexylcarbodiimide (17 mg, 0.08 mmol, 1.2 eq.). Shortly after the addition of dicyclohexylcarbodiimide, a white precipitate formed. This suspension was stirred at room temperature for 2 hours, then filtered directly into a separate flask containing β-1-(4-ethoxycarbonylamino-2-oxo-1H-pyrimidin-1-yl)-5-O-(tert-butyldimethylsilyl)-2-deoxy-2,2-difluororibose (30 mg, 0.067 mmol, 1.0 eq.) and 4-dimethylaminopyridine (1 mg, 0.007 mmol, 0.1 eq.) dissolved in 1 mL acetonitrile. This solution was stirred overnight at room temperature, then concentrated to provide a viscous oil, which was purified by chromatography over silica gel (solvent gradient=7:3 hexanes: ethyl acetate to 1:1 hexanes:ethyl acetate), yielding β-1-(4-ethoxycarbonylamino-2-oxo-1H-pyrimidin-1-yl)-3-O-(N-tert-butyloxycarbonyl-L-valinyl)-5-O-(tert-butyldimethylsilyl)-2-deoxy-2,2-difluororibose (13) (42 mg, 97%) as a clear viscous oil. $^1$H NMR ($CDCl_3$, 400 MHz): 0.00 (s, 6H), 0.80 (m, 12H), 0.87 (d, J=7.6 Hz, 3H), 1.21 (t, J=6.8 Hz), 3H), 1.32 (s, 9H), 2.06 (m, 1H), 3.68 (m, 1H), 3.88 (m, 1H), 4.03 (m, 1H), 4.15 (m, 3H), 5.38 (m, 1H), 6.32 (m, 1H), 7.12 (m, 1H), 7.90 (m, 1H)

6.11 Example 11

β-1-(4-Ethoxycarbonylamino-2-oxo-1H-pyrimidin-1-yl)-3-O-(L-valinyl)-2-deoxy-2,2-difluororibose (14)

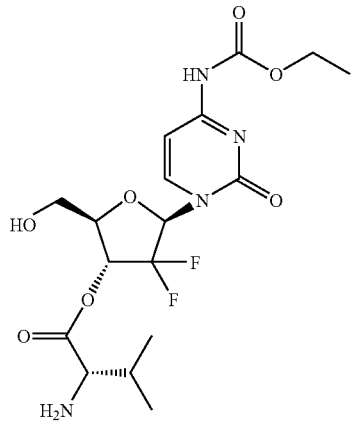

β-1-(4-Ethoxycarbonylamino-2-oxo-1H-pyrimidin-1-yl)-3-O-(N-tert-butyloxycarbonyl-L-valinyl)-5-O-(tert-butyldimethylsilyl)-2-deoxy-2,2-difluororibose (42 mg, 0.065 mmol) was dissolved in 4 mL dichloromethane. 1 mL of trifluoroacetic acid was added, and the solution was stirred at room temperature for 1 hour, at which time an additional 2 mL of trifluoroacetic acid were added, and the solution was stirred overnight at room temperature. The reaction was concentrated, leaving a viscous oil that was dissolved in acetonitrile:water (1:1), filtered, and purified by preparative LC-MS, yielding β-1-(4-ethoxycarbonylamino-2-oxo-1H-pyrimidin-1-yl)-3-O-(L-valinyl)-2-deoxy-2,2-difluororibose (14) (9 mg, 32%) as a white powder. $^1$H NMR (CD$_3$OD, 400 MHz): 1.12 (d, J=7.2 Hz, 6H), 1.32 (t, J=7.2 Hz, 3H), 2.46 (m, 1H), 3.80 (m, 1H), 3.98 (m, 1H), 4.15 (d, J=4.8 Hz, 1H), 4.24 (m, 2H), 4.33 (m, 1H), 5.61 (m, 1H), 6.34 (m, 1H), 7.36 (d, J=7.6 Hz, 1H), 8.19 (d, J=7.6 Hz, 1H). Ms (ESI) m/z 435.29 (M+H)$^+$, 433.25 (M−H)$^−$.

6.12 Example 12

β-1-(4-Ethoxycarbonylamino-2-oxo-1H-pyrimidin-1-yl)-3-O-(tetrahydropyranyl)-5-O-(tert-butyldimethylsilyl)-2-deoxy-2,2-difluororibose (15)

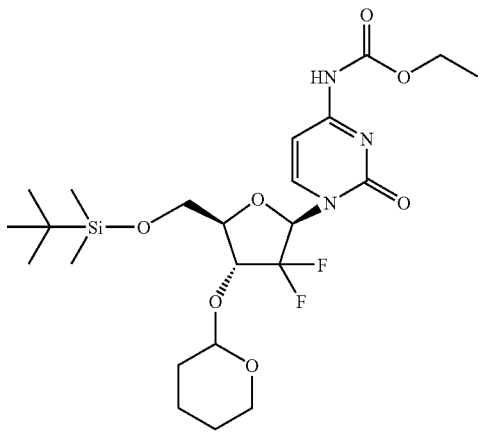

β-1-(4-Ethoxycarbonylamino-2-oxo-1H-pyrimidin-1-yl)-5-O-(tert-butyldimethylsilyl)-2-deoxy-2,2-difluororibose (90 mg, 0.20 mmol, 1.0 eq.), 3,4-dihydro-2H-pyran (36 μL, 0.40 mmol, 2.0 eq.) and pyridinium p-toluenesulfonate (10 mg, 0.04 mmol, 0.2 eq.) were dissolved in 2 mL dichloromethane, and the solution was stirred at room temperature 2 hours. At this time, additional dihydro-2H-pyran (36 μL, 0.40 mmol, 2.0 eq.), pyridinium p-toluenesulfonate (10 mg, 0.04 mmol, 0.2 eq.) and 2 mL chloroform were added and the solution was stirred at 40° C. overnight. The reaction was then concentrated, yielding a viscous oil, which was purified by chromatography over silica gel (solvent gradient=3:2 hexanes:ethyl acetate to 1:1 hexanes:ethyl acetate) to provide β-1-(4-ethoxycarbonylamino-2-oxo-1H-pyrimidin-1-yl)-3-O-(tetrahydropyranyl)-5-O-(tert-butyldimethylsilyl)-2-deoxy-2,2-difluororibose (15) (83 mg, 80%) as a viscous oil. $^1$H NMR (CDCl$_3$, 400 MHz): 0.12 (s, 6H), 0.98 (s, 9H), 1.25 (t, J=7.2 Hz, 3H), 1.50-1.90 (m, 8H), 3.55 (m, 1 m), 3.75-4.05 (m, 2H), 4.22 (m, 2H), 4.30-4.50 (m, 1H), 4.70-4.90 (m, 1H), 6.40 (m, 1H), 7.20 (m, 1H), 8.05 (m, 1H). MS (ESI) m/z 534.39 (M+H)$^+$.

6.13 Example 13

β-1-(4-Ethoxycarbonylamino-2-oxo-1H-pyrimidin-1-yl)-3-O-(tetrahydropyranyl)-2-deoxy-2,2-difluororibose (16)

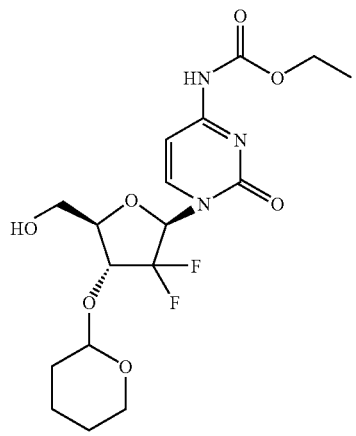

β-1-(4-Ethoxycarbonylamino-2-oxo-1H-pyrimidin-1-yl)-3-O-(tetrahydropyranyl)-5-O-(tert-butyldimethylsilyl)-2-deoxy-2,2-difluororibose (83 mg, 0.16 mmol, 1.0 eq.) was dissolved in 2 mL tetrahydrofuran. Triethylamine trihydrofluoride (8.5 μL, 0.05 mmol, 0.33 eq.) was added, and the reaction was stirred at room temperature overnight. Additional triethylamine trihydrofluoride was added in 0.33 eq. aliquots until a total of 1.5 eq. had been added over the course of 3 days. The reaction was monitored by TLC (2:3 hexane:ethyl acetate). When TLC showed complete consumption of the starting material, the reaction was concentrated to provide a viscous oil, which was purified over silica gel (solvent gradient of 1:1 hexane:ethyl acetate to 100% ethyl acetate) to provide β-1-(4-ethoxycarbonylamino-2-oxo-1H-pyrimidin-1-yl)-3-O-(tetrahydropyranyl)-2-deoxy-2,2-difluororibose (16) (56 mg, 85%) as a white solid. $^1$H NMR (CDCl$_3$, 400 MHz): 1.32 (t, J=7.2 Hz, 3H), 1.50-1.90 (m, 8H), 3.60 (m, 1H), 3.80-4.10 (m, 2H), 4.20 (m, 2H), 4.50-4.70 (m, 1H), 4.80-5.0 (m, 1H), 6.35 (m, 1H), 7.10-7.20 (m, 1H), 7.98-8.18 (m, 1H). MS (ESI) m/z 420.24 (M+H)$^+$, 418.26 (M−H)$^−$.

6.14 Example 14

β-1-(4-Ethoxycarbonylamino-2-oxo-1H-pyrimidin-1-yl)-3-O-(tetrahydropyranyl)-5-O-(N-tert-butoxycarbonyl-L-valinyl)-2-deoxy-2,2-difluororibose (17)

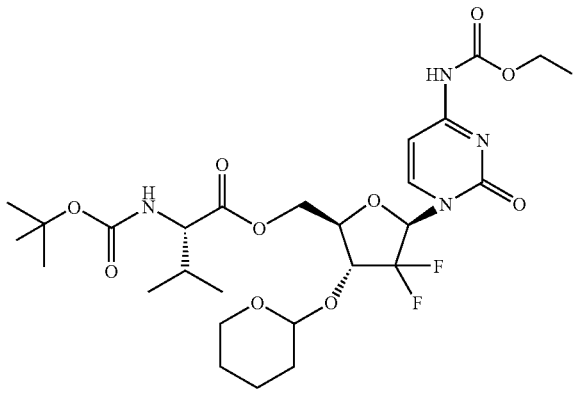

To a solution of N-tert-butoxycarbonyl-L-valine (87 mg, 0.40 mmol, 3.0 eq.) in 4 mL dichloromethane was added dicyclohexylcarbodiimide (41 mg, 0.20 mmol, 1.5 eq.). A white precipitate formed shortly after the addition of dicyclohexylcarbodiimide. The resultant suspension was stirred at room temperature for 2 hours, then filtered directly into a solution of β-1-(4-ethoxycarbonylamino-2-oxo-1H-pyrimidin-1-yl)-3-O-(tetrahydropyranyl)-2-deoxy-2,2-difluororibose (56 mg, 0.14 mmol, 1.0 eq.) and 4-dimethylaminopyridine (2 mg, 0.013 mmol, 0.1 eq.) in 2 mL dichloromethane. The resultant solution was stirred overnight at room temperature, then concentrated to yield a viscous oil, which was purified by chromatography over silica gel (solvent gradient 1:1 hexanes:ethyl acetate to 2:3 hexanes:ethyl acetate) to provide β-1-(4-ethoxycarbonylamino-2-oxo-1H-pyrimidin-1-yl)-3-O-(tetrahydropyranyl)-5-O-(N-tert-butoxycarbonyl-L-valinyl)-2-deoxy-2,2-difluororibose (17) (80 mg, 97%) as a viscous oil. $^1$H NMR (CDCl$_3$, 400 MHz): 0.90 (d, 3H), 1.00 (d, 3H), 1.35 (t, 3H), 1.40 (s, 9H), 1.50-1.90 (m, 8H), 2.10-2.30 (m, 1H), 3.50-5.10 (m, 8H), 6.35 (m, 1H), 7.40 (m, 1H), 7.80 (m, 1H). MS (ESI) m/z 619.42 (M+H)$^+$, 617.42 (M−H)$^-$.

6.15 Example 15

β-1-(4-Ethoxycarbonylamino-2-oxo-1H-pyrimidin-1-yl)-5-O-(L-valinyl)-2-deoxy-2,2-difluororibose (18)

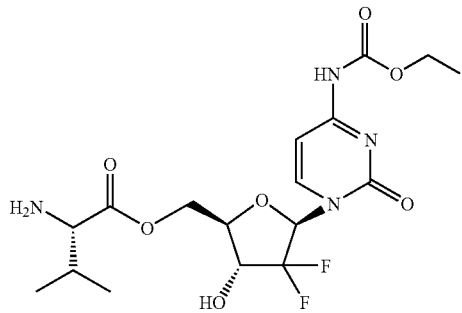

To a solution of β-1-(4-ethoxycarbonylamino-2-oxo-1H-pyrimidin-1-yl)-3-O-(tetrahydropyranyl)-5-O-(N-tert-butoxycarbonyl-L-valinyl)-2-deoxy-2,2-difluororibose (80 mg, 0.13 mmol, 1.0 eq.) in 2 mL dichloromethane was added 2 mL trifluoroacetic acid. The solution was stirred at room temperature for 1 hour, then concentrated to provide a viscous oil, which was dissolved in 1:1 acetonitrile:water, filtered and purified by preparative LC-MS to yield β-1-(4-ethoxycarbonylamino-2-oxo-1H-pyrimidin-1-yl)-5-O-(L-valinyl)-2-deoxy-2,2-difluororibose (18) (28 mg, 50%) as a white powder. $^1$H NMR (CD$_3$OD, 400 MHz): 1.06 (d, J=7.2 Hz, 6H), 1.31 (t, J=7.2 Hz, 3H), 2.28 (m, 1H), 3.98 (m, 1H), 4.19-4.34 (m, 4H), 4.61 (m, 2H), 6.20 (m, 1H), 7.30 (d, J=8.0 Hz, 1H), 7.93 (d, J=8.0 Hz, 1H). MS (ESI) m/z 435.22 (M+H)$^+$, 433.25 (M−H)$^-$.

6.16 Example 16

β-1-(4-Allyloxycarbonylamino-2-oxo-1H-pyrimidin-1-yl)-5-O-(tert-butyldimethylsilyl)-2-deoxy-2,2-difluororibose (19)

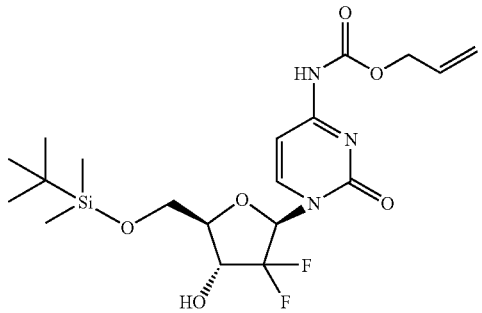

β-1-(4-Allyloxycarbonylamino-2-oxo-1H-pyrimidin-1-yl)-2-deoxy-2,2-difluororibose (3.42 g, 9.86 mmol, 1.0 eq.) and imidazole (1.34 g, 19.7 mmol, 2.0 eq.) were dissolved in 100 mL acetonitrile and cooled to 0° C. To this was added tert-butyldimethylsilyl chloride (2.98 g, 19.7 mmol, 2.0 eq.), and the solution was stirred from 0° C. to room temperature overnight. After overnight stirring, the reaction was filtered and concentrated to give a viscous oil, which was purified by chromatography over silica gel (solvent gradient=2:3 hexanes:ethyl acetate to 3:7 hexanes:ethyl acetate) to provide β-1-(4-allyloxycarbonylamino-2-oxo-1H-pyrimidin-1-yl)-5-O-(tert-butyldimethylsilyl)-2-deoxy-2,2-difluororibose (19) (2.80 g, 62%) as a white powder. $^1$H NMR (CDCl$_3$, 400 MHz): 0.00 (s, 6H), 0.79 (s, 9H), 3.79 (m, 1H), 3.93 (m, 2H), 4.23 (m, 1H), 4.54 (d, J=5.6 Hz, 2H), 5.19 (m, 2H), 5.78 (m, 1H), 6.22 (m, 1H), 7.20 (m, 1H), 8.01 (m, 1H). MS (ESI) m/z 462.28 (M+H)$^+$, 460.25 (M−H)$^-$.

6.17 Example 17

β-1-(4-Allyloxycarbonylamino-2-oxo-1H-pyrimidin-1-yl)-3-O-(4-carboxybutyro-1-yl)-2-deoxy-2,2-difluororibose (20)

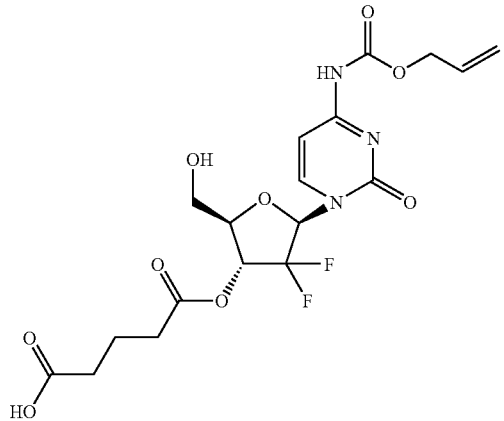

β-1-(4-Allyloxycarbonylamino-2-oxo-1H-pyrimidin-1-yl)-5-O-(tert-butyldimethylsilyl)-2-deoxy-2,2-difluororibose (290 mg, 0.63 mmol, 1.0 eq.) was dissolved in 6 mL chloroform. Glutaric anhydride (107 mg, 0.94 mmol, 1.5 eq.) and pyridine (254 µL, 3.15 mmol, 5.0 eq.) were added, and the solution was stirred at 45° C. overnight. After overnight stirring, 4-dimethylaminopyridine (15 mg, 0.13 mmol, 0.2 eq.) and additional glutaric anhydride (107 mg, 0.94 mmol, 1.5 eq.) were added, and the solution was stirred at 30° C. for 3 days, after which the reaction was concentrated, leaving a viscous oil. This oil was dissolved in 6 mL dichloromethane and treated with 6 mL trifluoroacetic acid at room temperature for 4 hours. The reaction was concentrated yielding a viscous oil, which was dissolved in 1:1 acetonitrile:water, filtered and purified by preparative LC-MS, yielding β-1-(4-allyloxycarbonylamino-2-oxo-1H-pyrimidin-1-yl)-3-O-(4-carboxybutyro-1-yl)-2-deoxy-2,2-difluororibose (20) (121 mg, 42%) as a white powder. $^1$H NMR (CD$_3$OD, 400 MHz): 1.93 (m, 2H), 2.38 (t, J=7.2 Hz, 2H), 2.56 (t, J=7.2 Hz, 2H), 3.80 (m, 1H), 3.96 (m, 1H), 4.25 (m, 1H), 4.69 (d, J=5.6 Hz, 2H), 5.26 (m, 1H), 5.38 (m, 1H), 5.46 (m, 1H), 6.00 (m, 1H), 6.33 (t, J=8 Hz, 1H), 7.36 (d, J=8 Hz, 1H), 8.23 (d, J=8 Hz, 1H). MS (ESI) m/z 462.20 (M+H)$^+$, 460.21 (M−H)$^−$.

6.18 Example 18

β-1-(4-Amino-2-oxo-1H-pyrimidin-1-yl)-3-O-(4-carboxybutyro-1-yl)-2-deoxy-2,2-difluororibose (21)

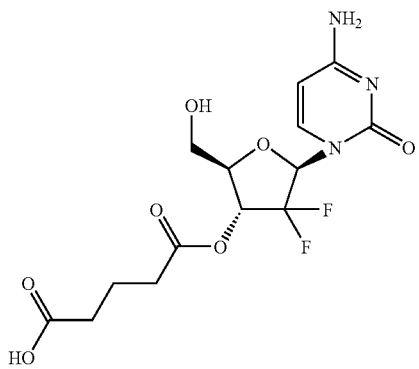

β-1-(4-Allyloxycarbonylamino-2-oxo-1H-pyrimidin-1-yl)-3-O-(4-carboxybutyro-1-yl)-2-deoxy-2,2-difluororibose (103 mg, 0.22 mmol, 1.0 eq.), triphenylphosphine (24 mg, 0.09 mmol, 0.4 eq.), ethanolamine (27 µL, 0.44 mmol, 2.0 eq.), and formic acid (33 µL, 0.88 mmol, 4.0 eq.) were dissolved in 2 mL tetrahydrofuran, 2 mL acetonitrile and 1 mL water and the solution degassed by bubbling under N$_2$ for 1 min. Tetrakis(triphenylphosphine)palladium(0) (23 mg, 0.02 mmol, 0.1 eq.) was added, and the solution was stirred at room temperature 1 hour. At this point, additional tetrakis(triphenylphosphine)palladium(0) (23 mg, 0.02 mmol, 0.1 eq.) from a fresh bottle was added, and the reaction was stirred overnight at room temperature. The reaction solution was concentrated to yield a viscous oil, which was dissolved in 1:1 acetonitrile:water, filtered and purified by preparative LC-MS to yield β-1-(4-amino-2-oxo-1H-pyrimidin-1-yl)-3-O-(4-carboxybutyro-1-yl)-2-deoxy-2,2-difluororibose (21) (53 mg, 63%) as a white powder. $^1$H NMR (CD$_3$OD, 400 MHz): 1.94 (m, 2H), 2.39 (t, J=7.2 Hz, 2H), 2.56 (t, J=7.2 Hz, 2H), 3.79 (m, 1H), 3.94 (m, 1H), 4.19 (m, 1H), 5.41 (m, 1H), 5.92 (d, J=8.0 Hz, 1H), 6.29 (t, J=8.0 Hz, 1H), 7.81 (d, J=8.0 Hz, 1H). MS (ESI) m/z 378.26 (M+H)$^+$, 376.24 (M−H)$^−$.

6.19 Example 19

β1-(4-Allyloxycarbonylamino-2-oxo-1H-pyrimidin-1-yl)-3-O-(tetrahydropyranyl)-5-O-(tert-butyldimethylsilyl)-2-deoxy-2,2-difluororibose (22)

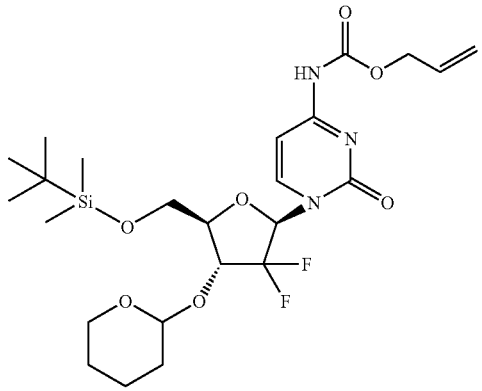

β-1-(4-Allyloxycarbonylamino-2-oxo-1H-pyrimidin-1-yl)-5-O-(tert-butyldimethylsilyl)-2-deoxy-2,2-difluororibose (1.24 g, 2.69 mmol, 1.0 eq.) was dissolved in 10 mL chloroform. To this solution was added 3,4-dihydro-2H-pyran (491 µL, 5.38 mmol, 2.0 eq.) and pyridinium p-toluenesulfonate (136 mg, 0.54 mmol, 0.2 eq.), and the solution was stirred at room temperature. After 48 hours, additional 3,4-dihydro-2H-pyran (491 µL, 5.38 mmol, 2.0 eq.) was added, and the reaction was stirred at 45° C. for 4 hours. The reaction was concentrated, yielding a viscous oil, which was purified by chromatography over silica gel (solvent gradient=3:2 hexanes: ethyl acetate to 1:1 hexanes:ethyl acetate) to provide β-1-(4-allyloxycarbonylamino-2-oxo-1H-pyrimidin-1-yl)-3-O-(tetrahydropyranyl)-5-O-(tert-butyldimethylsilyl)-2-deoxy-2,2-difluororibose (22) (1.46 g quantitative) as a viscous oil. $^1$H NMR (CDCl$_3$, 400 MHz) 0.00 (s, 6H), 0.80 (s, 9H), 1.40-1.80 (m, 8H), 3.40 (m, 1H), 3.60-4.80 (m, 6H), 5.20 (m, 2H), 5.80 (m, 1H), 6.22 (m, 1H), 7.02 (m, 1H), 7.98 (m, 1H). MS (ESI) m/z 546.33 (M+H)+, 544.30 (M−H)−.

6.20 Example 20

β-1-(4-Allyloxycarbonylamino-2-oxo-1H-pyrimidin-1-yl)-3-O-(tetrahydropyranyl)-2-deoxy-2,2-difluororibose (23)

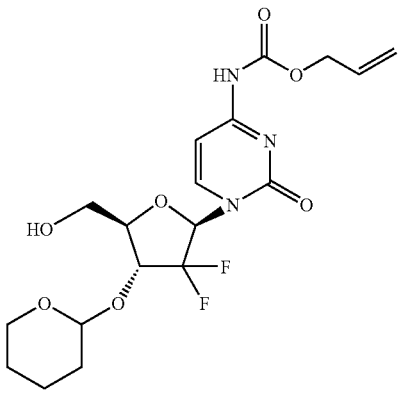

β-1-(4-Allyloxycarbonylamino-2-oxo-1H-pyrimidin-1-yl)-3-O-(tetrahydropyranyl)-5-O-(tert-butyldimethylsilyl)-2-deoxy-2,2-difluororibose (1.46 g, 2.7 mmol, 1.0 eq.) was dissolved in 10 mL THF. Triethylamine trihydrofluoride (653 μL, 4.0 mmol, 1.5 eq.) was added, and the solution was stirred at room temperature for 3 days. The reaction was concentrated, yielding a viscous oil, which was purified by chromatography over silica gel (solvent gradient=1:1 hexanes:ethyl acetate to 1:4 hexanes:ethyl acetate) to provide β-1-(4-allyloxycarbonylamino-2-oxo-1H-pyrimidin-1-yl)-3-O-(tetrahydropyranyl)-2-deoxy-2,2-difluororibose (23) (760 mg, 66%) as a white powder. $^1$H NMR (CDCl3, 400 MHz) 1.50-1.90 (m, 8H), 3.60 (m, 1H), 3.80-4.10 (m, 4H), 4.60 (m, 2H), 5.30-5.40 (m, 2H), 5.90 (m, 1H), 6.35 (m, 1H), 7.10-7.30 (m, 1H), 7.90-8.10 (m, 1H). MS (ESI) m/z 432.21 (M+H)+, 430.25 (M−H)−.

6.21 Example 21

β-1-(4-Allyloxycarbonylamino-2-oxo-1H-pyrimidin-1-yl)-5-O-(4-carboxybutyro-1-yl)-2-deoxy-2,2-difluororibose (24)

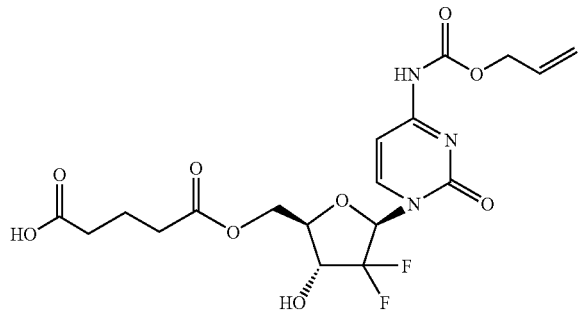

β-1-(4-Allyloxycarbonylamino-2-oxo-1H-pyrimidin-1-yl)-3-O-(tetrahydropyranyl)-2-deoxy-2,2-difluororibose (265 mg, 0.61 mmol, 1.0 eq.) was dissolved in 6 mL chloroform. Glutaric anhydride (140 mg, 1.23 mmol, 2.0 eq.), pyridine (246 μL, 3.05 mmol, 5.0 eq.) and 4-dimethylaminopyridine (15 mg, 0.12 mmol, 0.2 eq.) were added, and the reaction was stirred at 35° C. overnight. The reaction was then cooled and concentrated, leaving a viscous oil. This oil was dissolved in 6 mL dichloromethane, to which was added 6 mL trifluoroacetic acid, and the solution was stirred at room temperature 1 hour. The reaction was concentrated, yielding a viscous oil, which was dissolved in 1:1 acetonitrile:water, filtered and purified by preparative LC-MS, to provide β-1-(4-allyloxycarbonylamino-2-oxo-1H-pyrimidin-1-yl)-5-O-(4-carboxybutyro-1-yl)-2-deoxy-2,2-difluororibose (24) (140 mg, 53%) as a white powder. $^1$H NMR (CD$_3$OD, 400 MHz): 1.93 (m, 2H). 2.38 (t, J=7.2 Hz, 2H), 2.49 (t, J=7.2 Hz, 2H), 4.15-4.28 (m, 2H), 4.46 (d, J=4 Hz, 2H), 4.69 (m, 2H), 5.26 (m, 1H), 5.39 (m, 1H), 5.98 (m, 1H), 6.26 (t, J=8 Hz, 1H), 7.36 (d, J=7.2 Hz, 1H), 7.98 (d, J=7.2 Hz, 1H). MS (ESI) m/z 462.20 (M+H)+, 460.21 (M−H)−.

6.22 Example 22

β-1-(4-Amino-2-oxo-1H-pyrimidin-1-yl)-5-O-(4-carboxybutyro-1-yl)-2-deoxy-2,2-difluororibose (25)

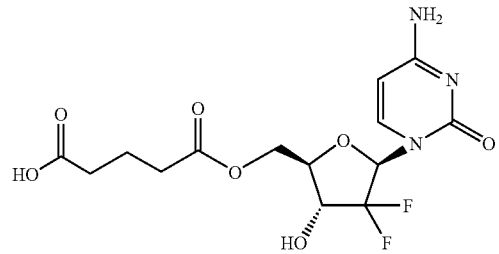

β-1-(4-Allyloxycarbonylamino-2-oxo-1H-pyrimidin-1-yl)-5-O-(4-carboxybutyro-1-yl)-2-deoxy-2,2-difluororibose (119 mg, 0.26 mmol, 1.0 eq.), triphenylphosphine (26 mg, 0.10 mmol, 0.4 eq.), ethanolamine (32 μL, 0.52 mmol, 2.0 eq.), and formic acid (39 μL, 1.04 mmol, 4.0 eq.) were dissolved in 4 mL tetrahydrofuran, and 500 μL water and the solution degassed by bubbling under N$_2$ for 1 min. Tetrakis(triphenylphosphine)-palladium(0) (30 mg, 0.026 mmol, 0.1 eq.) was added, and the solution was stirred at room temperature 1 hour. At this point additional tetrakis(triphenylphosphine)palladium(0) (30 mg, 0.026 mmol, 0.1 eq.) from a fresh bottle was added, and the reaction was stirred an additional 1 hour at room temperature, then concentrated to yield a viscous oil. This oil was dissolved in 1:1 acetonitrile:water, filtered, and purified by preparative LC-MS to provide β-1-(4-amino-2-oxo-1H-pyrimidin-1-yl)-5-O-(4-carboxybutyro-1-yl)-2-deoxy-2,2-difluororibose (25) (59 mg, 61%) as a white powder. $^1$H NMR (CD$_3$OD, 400 MHz): 1.92 (m, 2H), 2.36 (t, J=7.2 Hz, 2H), 2.48 (t, J=7.2 Hz, 2H), 4.10-4.22 (m, 2H), 4.41 (m, 2H), 5.98 (m, 1H), 6.21 (t, J=8.0 Hz, 1H), 7.60 (m, 1H). MS (ESI) m/z 378.26 (M+H)+, 376.24 (M−H)−.

6.23 Example 23

β-1-(4-Pentyloxycarbonylamino-2-oxo-1H-pyrimidin-1-yl)-2-deoxy-2,2-difluororibose (26)

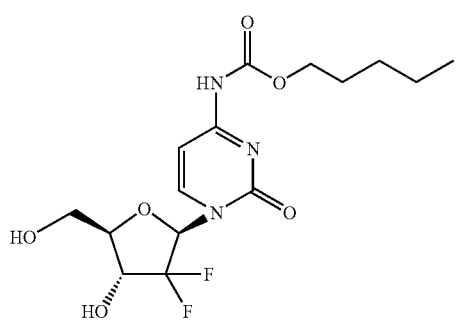

β-1-(4-Amino-2-oxo-1H-pyrimidin-1-yl)-5-O-(pentyloxycarbonyl)-2-deoxy-2,2-difluororibose (27)

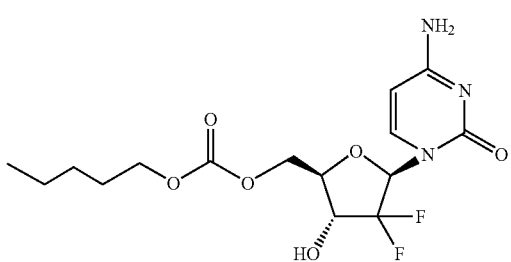

β-1-(4-Amino-2-oxo-1H-pyrimidin-1-yl)-3-O-(pentyloxycarbonyl)-2-deoxy-2,2-difluororibose (28)

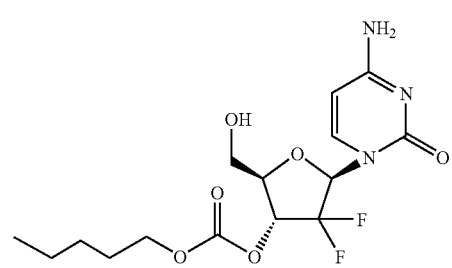

β-1-(4-Pentyloxycarbonylamino-2-oxo-1H-pyrimidin-1-yl)-3-O-(pentyloxycarbonyl)-2-deoxy-2,2-difluororibose (29)

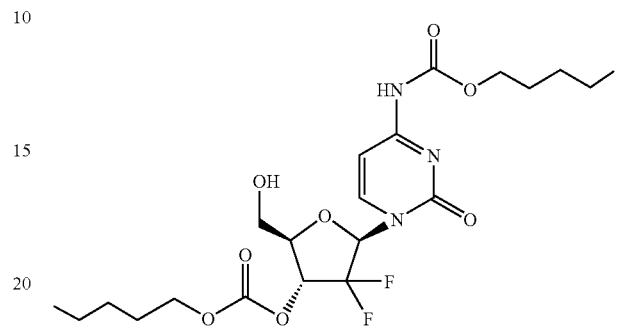

β-1-(4-Pentyloxycarbonylamino-2-oxo-1H-pyrimidin-1-yl)-5-O-(pentyloxycarbonyl)-2-deoxy-2,2-difluororibose (30)

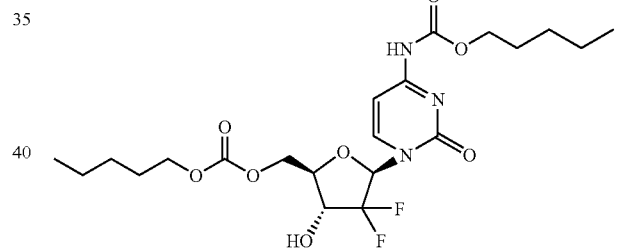

β-1-(4-Amino-2-oxo-1H-pyrimidin-1-yl)-3-O-(Pentyloxycarbonyl)-5-O-(pentyloxycarbonyl)-2-deoxy-2,2-difluororibose (31)

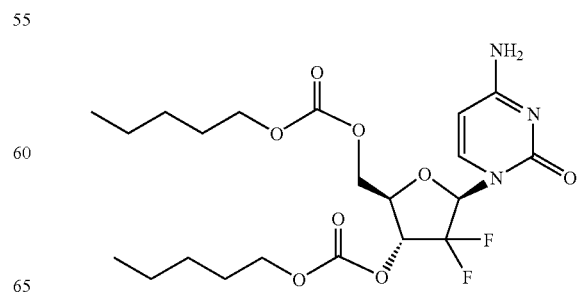

β-1-(4-Pentyloxycarbonylamino-2-oxo-1H-pyrimidin-1-yl)-3-O-(pentyloxycarbonyl)-5-O-(Pentyloxycarbonyl)-2-deoxy-2,2-difluororibose (32)

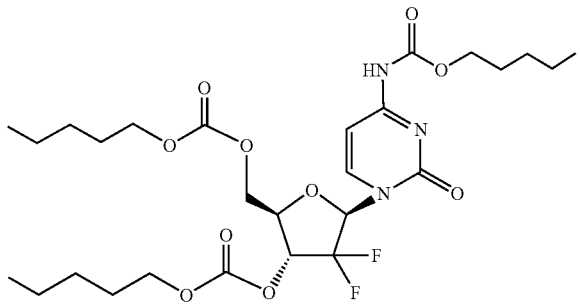

The above 7 compounds were each isolated by preparative LC-MS chromatography from the following reaction. To a solution of β-1-(4-amino-2-oxo-1H-pyrimidin-1-yl)-2-deoxy-2,2-difluororibose. HCl (300 mg, 1.0 mmol, 1.0 eq.) and diisopropylethylamine (436 μL, 2.5 mmol, 2.5 eq.) in 10 mL pyridine was added n-pentyl chloroformate (290 μL, 2.0 mmol, 2.0 eq.), and the solution was stirred overnight at room temperature. The reaction solution was concentrated to remove the pyridine, leaving a viscous oil, which was dissolved in 1:1 acetonitrile:water, filtered and purified by preparative LC-MS to provide the titled compounds in the amounts indicated below:

β-1-(4-Pentyloxycarbonylamino-2-oxo-1H-pyrimidin-1-yl)-2-deoxy-2,2-difluororibose (26): (101 mg, 27%, white powder) $^1$H NMR (CD$_3$OD, 400 MHz): 0.92 (m, 3H), 1.39 (m, 4H), 1.61 (m, 2H), 3.81 (m, 1H), 3.97 (m, 2H), 4.18 (m, 2H), 4.30 (m, 1H), 6.21 (m, 1H), 7.35 (d, J=7.6 Hz, 1H), 8.28 (d, J=7.6 Hz, 1H). MS (ESI) m/z 378.26 (M+H)$^+$, 376.30 (M−H)$^−$.

β-1-(4-Amino-2-oxo-1H-pyrimidin-1-yl)-5-O-(pentyloxycarbonyl)-2-deoxy-2,2-difluororibose (27): (1 mg, <1%, white powder) $^1$H NMR (CD$_3$OD, 400 MHz): 0.92 (m, 3H), 1.38 (m, 4H), 1.68 (m, 2H), 4.08-4.22 (m, 4H), 4.40-4.58 (m, 2H), 5.90 (d, J=7.6, 1H), 6.22 (t, J=8.0 Hz, 1H), 7.60 (d, J=7.6 Hz, 1H). MS (ESI) m/z 378.19 (M+H)$^+$.

β-1-(4-Amino-2-oxo-1H-pyrimidin-1-yl)-3-O-(pentyloxycarbonyl)-2-deoxy-2,2-difluororibose (28): (4 mg, 1%, white powder) $^1$H NMR (CD$_3$OD, 400 MHz): 0.96 (m, 3H), 1.39 (m, 4H), 1.70 (m, 2H), 3.79 (m, 1H), 3.96 (m, 1H), 4.20 (m, 3H), 5.28 (m, 1H), 5.96 (d, J=7.6 Hz, 1H), 6.26 (t, J=8.0 Hz, 1H), 7.79 (d, J=7.6 Hz, 1H). MS (ESI) m/z 378.24 (M+H)$^+$.

β-1-(4-Pentyloxycarbonylamino-2-oxo-1H-pyrimidin-1-yl)-3-O-(pentyloxycarbonyl)-2-deoxy-2,2-difluororibose (29): (54 mg, 11%, white powder) $^1$H NMR (CD$_3$OD, 400 MHz): 0.96 (m, 6H), 1.39 (m, 8H), 1.70 (m, 4H), 3.80 (m, 1H), 3.98 (m, 1H), 4.18-4.30 (m, 5H), 5.35 (m, 1H), 6.36 (t, J=8.0 Hz, 1H), 7.38 (d, J=7.6 Hz, 1H), 8.20 (d, J=7.6 Hz, 1H). MS (ESI) m/z 492.25 (M+H)$^+$, 490.29 (M−H)$^−$.

β-1-(4-Pentyloxycarbonylamino-2-oxo-1H-pyrimidin-1-yl)-5-O-(pentyloxycarbonyl)-2-deoxy-2,2-difluororibose (30): (12 mg, 2%, white powder) $^1$H NMR (CD$_3$OD, 400 MHz): 0.96 (m, 6H), 1.40 (m, 8H), 1.70 (m, 4H), 4.15-4.25 (m, 6H), 4.45 (m, 1H), 4.55 (m, 1H), 6.28 (t, J=7.6 Hz, 1H), 7.36 (d, J=7.6 Hz, 1H), 8.01 (d, J=7.6 Hz, 1H), MS (ESI) m/z 492.25 (M+H)$^+$, 490.29 (M−H)$^−$.

β-1-(4-Amino-2-oxo-1H-pyrimidin-1-yl)-3-O-(pentyloxycarbonyl)-5-O-(pentyloxycarbonyl)-2-deoxy-2,2-difluororibose (31): (9 mg, 2%, white powder) $^1$H NMR (CD$_3$OD, 400 MHz): 0.96 (m, 6H), 1.39 (m, 8H), 1.70 (m, 4H), 4.15-4.25 (m, 4H), 4.40 (m, 1H), 4.50 (m, 2H), 5.24 (m, 1H), 5.92 (d, J=8.0 Hz, 1H), 6.28 (t, J=8.4 Hz, 1H), 7.59 (d, J=8.0 Hz, 1H). MS (ESI) m/z 492.29 (M+H)$^+$, 490.29 (M−H)$^−$.

β-1-(4-Pentyloxycarbonylamino-2-oxo-1H-pyrimidin-1-yl)-3-O-(pentyloxycarbonyl)-5-O-(pentyloxycarbonyl)-2-deoxy-2,2-difluororibose (32): (39 mg, 6%, white powder) $^1$H NMR (CD$_3$OD, 400 MHz): 0.96 (m, 9H), 1.38 (m, 12H), 1.72 (m, 6H), 4.15-4.25 (m, 6H), 4.45-4.60 (m, 3H), 5.35 (m, 1H), 6.38 (t, J=8.0 Hz, 1H), 7.38 (d, J=7.2 Hz, 1H), 7.99 (d, J=7.2 Hz, 1H). MS (ESI) m/z 606.35 (M+H)$^+$.

6.24 Example 24

β-1-(4-amino-2-oxo-1H-pyrimidin-1-yl)-3,5-O-di-(tert-butyldimethylsilyl)-2-deoxy-2,2-difluororibose (33)

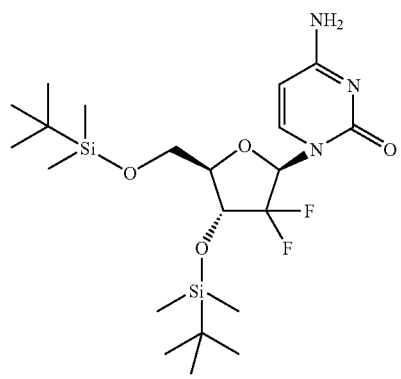

β-1-(4-Allyloxycarbonylamino-2-oxo-1H-pyrimidin-1-yl)-2-deoxy-2,2-difluororibose (1) (3.42 g, 9.86 mmol 1.0 eq.) and imidazole (2.68 g, 39.4 mmol, 4.0 eq.) were dissolved in acetonitrile (100 mL) and cooled to 0° C. To this was added tert-butyldimethylsilyl chloride (5.96 g, 39.4 mmol, 4.0 eq.), and the solution was stirred from 0° C. to room temperature overnight. The reaction was then concentrated in vacuo to a viscous oil, which was dissolved in dichloromethane (100 mL) and extracted twice with 1N HCl solution (25 mL), then twice with saturated sodium bicarbonate solution (25 mL). The organic layer was dried over anhydrous sodium sulfate and concentrated in vacuo, providing a viscous oil. The oil was dissolved in THF (50 mL) and treated with triphenylphosphine (1.03 g, 3.94 mmol, 0.4 eq.), ethanolamine (1.21 mL, 19.7 mmol, 2.0 eq.), and formic acid (1.48 mL, 39.4 mmol, 4.0 eq.). The solution was degassed by bubbling nitrogen gas for 1 min. Tetrakis (triphenylphosphine)-palladium (0) (1.13 g, 0.98 mmol, 0.1 eq.) was added, and the solution was stirred at room temperature 1 h. The reaction solution was then concentrated and dichloromethane (100 mL) was added. The solution was extracted twice with saturated sodium bicarbonate solution (25 mL) and the organic layer dried over sodium sulfate, then concentrated in vacuo to a viscous oil. The oil was purified by silica gel chromatography to provide β-1-(4-amino-2-oxo-1H-pyrimidin-1-yl)-3,5-O-di-(tert-butyldimethylsilyl)-2-deoxy-2,2-difluororibose (33) as colorless oil (4.07 g, 84%). $^1$H NMR (CDCl$_3$, 400 MHz): 0.00 (s, 12H), 0.79 (s, 18H), 3.67 dd, 1H), 3.75 (d, 2H), 3.85 (d, 1H), 4.20

(m, 1H), 5.75 (d, 1H), 6.21 (m, 1H), 7.46 (d, 1H). MS (ESI) m/z 492.37 (M+H)⁺, 490.41 (M−H)⁻.

6.25: Example 25

β-1-(4-Phenyloxycarbonylamino-2-oxo-1H-pyrimidin-1-yl)-2-deoxy-2,2-difluororibose (34)

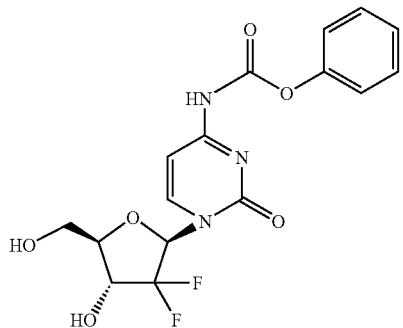

Compound (33) (491 mg, 1 mmol) was dissolved in dichloromethane (15 mL) and cooled to 0° C. To this was added pyridine (97 μL, 1.2 mmol, 1.2 eq.) and phenyl chloroformate (151 μL, 1.2 mmol, 1.2 eq.), and the solution was stirred at 0° C. for 1 h. The solution was extracted with 1N HCl solution (3 mL) and saturated sodium bicarbonate solution (3 mL). The dichloromethane solution was dried over anhydrous sodium sulfate and concentrated in vacuo to a viscous oil. The oil was dissolved in THF (10 mL), triethylamine trihydrofluoride (0.65 mL, 4 mmol, 4 eq.) was added, and the solution was stirred at room temperature for 2 days. The reaction solution was concentrated in vacuo to yield a viscous oil, which was dissolved in 1:1 acetonitrile:water, filtered and purified by preparative HPLC. The title compound (34) was obtained as a white powder (149 mg, 39%). ¹H NMR (CD₃OD, 400 MHz): 3.79 (dd, 1H), 3.96 (m, 2H), 4.29 (m, 1H), 6.25 (t, 1H), 7.19 (d, 2H), 7.28 (m, 2H), 7.40 (t, 2H), 8.34 (d, 1H). MS (ESI) m/z 384.15 (M+H)⁺, 382.19 (M−H)⁻.

6.26: Example 26

β-1-(4-(4-Methoxyphenyl)oxycarbonylamino-2-oxo-1H-pyrimidin-1-yl)-2-deoxy-2,2-difluororibose (35)

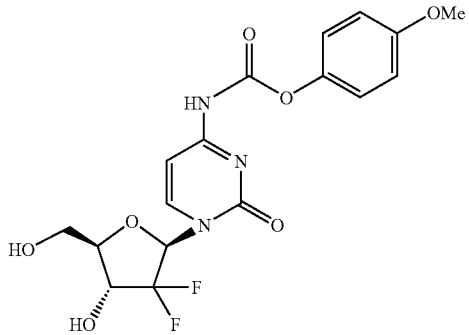

The above compound was prepared in the manner described in Example 25, substituting phenyl chloroformate with 4-methoxyphenyl chloroformate. The title compound (35) was obtained as a white powder (145 mg, 35%). ¹H NMR (CD₃OD, 400 MHz): 3.79 (m, 4H), 3.96 (m, 2H), 4.29 (m, 1H), 6.25 (t, 1H), 6.92 (d, 2H), 7.10 (d, 2H), 7.30 (d, 1H), 8.33 (d, 1H). MS (ESI) m/z 414.01 (M+H)⁺, 412.05 (M−H)⁻.

6.27: Example 27

β-1-(4-(1,1,1-Trifluoroethyl)oxycarbonylamino-2-oxo-1H-pyrimidin-1-yl)-2-deoxy-2,2-difluororibose (36)

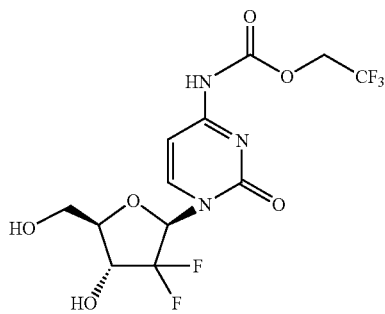

The above compound was prepared in the manner described in Example 25, substituting phenyl chloroformate with 1,1,1-trifluoroethyl chloroformate. The title compound (36) was obtained as a white powder (175 mg, 45%). ¹H NMR (CD₃OD, 400 MHz): 3.79 (dd, 1H), 3.96 (m, 2H), 4.29 (m, 1H), 4.71 (q, 2H), 6.23 (t, 1H), 7.26 (d, 1H), 8.34 (d, 1H). MS (ESI) m/z 390.09 (M+H)⁺, 388.11 (M−H)⁻.

6.28: Example 28

β-1-(4-(4-Methoxybenzyl)oxycarbonylamino-2-oxo-1H-pyrimidin-1-yl)-2-deoxy-2,2-difluororibose (37)

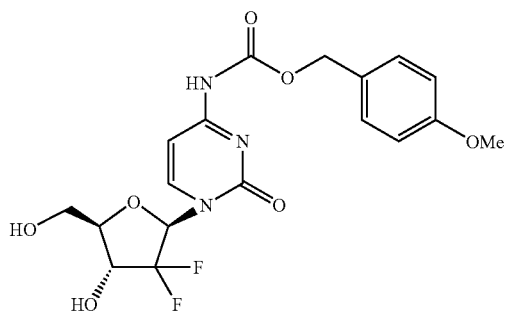

The above compound was prepared in the manner described in Example 25, substituting phenyl chloroformate with 4-methoxybenzyl chloroformate. The title compound (37) was obtained as a white powder (141 mg, 33%) ¹H NMR (CD₃OD, 400 MHz): 3.79 (m, 4H), 3.94 (m, 2H), 4.29 (m, 1H), 5.13 (s, 2H), 6.22 (t, 1H), 6.89 (d, 2H), 7.33 (m, 3H), 8.29 (d, 1H). MS (ESI) m/z 428.05 (M+H)⁺, 426.07 (M−H)⁻.

6.29: Example 29

β-1-(4-(Propen-2-yl)oxycarbonylamino-2-oxo-1H-pyrimidin-1-yl)-2-deoxy-2,2-difluororibose (38)

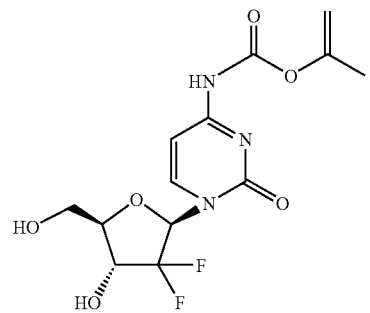

The above compound was prepared in the manner described in Example 25, substituting phenyl chloroformate with isopropenyl chloroformate. The title compound (38) was obtained as a white powder (108 mg, 31%). $^1$H NMR (CD$_3$OD, 400 MHz): 1.98 (s, 3H), 3.80 (dd, 1H), 3.96 (m, 2H), 4.29 (m, 1H), 4.78 (s, 1H), 4.89 (s, 1H), 6.24 (t, 1H), 7.30 (dd, 1H), 8.31 (d, 1H). MS (ESI) m/z 348.31 (M+H)$^+$, 346.27 (M–H)$^-$.

6.30: Example 30

β-1-(4-Pentyloxycarbonylamino-2-oxo-1H-pyrimidin-1-yl)-2-deoxy-2,2-difluororibose (26)

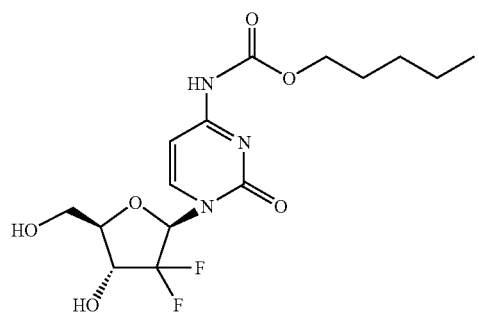

The above compound was prepared in the manner described in Example 25, substituting phenyl chloroformate with n-pentyl chloroformate. The title compound (26) was obtained as a white powder (121 mg, 32%). $^1$H NMR (CD$_3$OD, 400 MHz): 0.92 (m, 3H), 1.39 (m, 4H), 1.61 (m, 2H), 3.81 (m, 1H), 3.97 (m, 2H), 4.18 (m, 2H), 4.30 (m, 1H), 6.21 (m, 1H), 7.35 (d, J=7.6 Hz, 1H), 8.28 (d, J=7.6 Hz, 1H). MS (ESI) m/z 378.26 (M+H)$^+$, 376.30 (M–H)$^-$.

6.31: Example 31

β-1-(4-(2-Carboxy-2-methyl)ethoxycarbonylamino-2-oxo-1H-pyrimidin-1-yl)-2-deoxy-2,2-difluororibose (39)

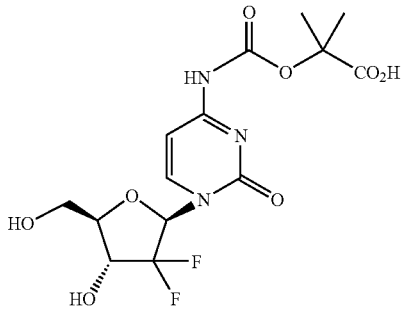

Compound (33) (491 mg, 1 mmol, 1 eq.) was dissolved in dichloromethane (5 mL) and cooled to 0° C. To this was added pyridine (324 ηL, 4 mmol, 4 eq.) and 1.93 M solution of phosgene in toluene (2.07 mL, 4 mmol, 4.0 eq.), and the solution was stirred at 0° C. for 1 h. The reaction solvent was evaporated in vacuo, leaving a viscous oil. The oil was dissolved in toluene (10 mL) and tert-butyl-2-hydroxyisobutyrate (347 μL, 2 mmol, 2 eq.) was added and the solution was heated at 100° C. for 16 h. The solution was diluted with ethyl acetate (30 mL) and extracted with 1N HCl solution (5 mL) and saturated sodium bicarbonate solution (3 mL). The organic layer was dried over anhydrous sodium sulfate and concentrated in vacuo to a viscous oil. The oil was dissolved in THF (10 mL), triethylamine trihydrofluoride (0.65 mL, 4 mmol, 4 eq.) was added, and the solution was stirred at room temperature for 2 days. The solution was concentrated in vacuo to yield a viscous oil, then treated with 1:1 trifluoroacetic acid:dichloromethane (10 mL) for 2 h. The reaction solution was again concentrated in vacuo to yield a viscous oil, which was dissolved in 1:1 acetonitrile:water, filtered and purified by preparative HPLC. The title compound (39) was obtained as a white powder (68 mg, 17%). $^1$H NMR (CD$_3$OD, 400 MHz): 1.40 (s, 6H), 3.80 (m, 1H), 3.94 (m, 2H), 4.28 (m, 1H), 6.23 (t, 1H), 7.25 (d, 1H), 8.28 (d, 1H). MS (ESI) m/z 394.19 (M+H)$^+$, 392.15 (M–H)$^-$.

6.32: Example 32

β-1-(4-Pentyloxycarbonylamino-2-oxo-1H-pyrimidin-1-yl)-5-O-acetyl-2-deoxy-2,2-difluororibose (40)

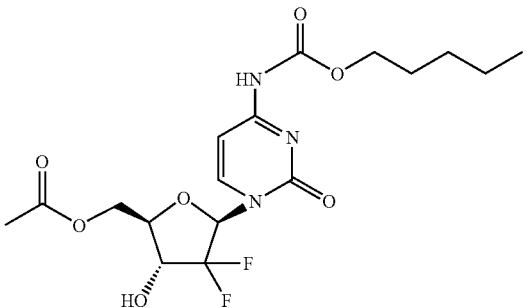

Compound (23) (265 mg, 0.61 mmol, 4.0 eq.) was dissolved in dichloromethane (1 mL), acetic anhydride (288 μL, 3.05 mmol, 5.0 eq.) and pyridine (246 μL, 3.05 mmol, 5.0 eq.) were added, and the reaction was stirred at room temperature for 1 h. The reaction was then concentrated in vacuo, leaving a viscous oil. This oil was dissolved in THF (4 mL), triphenylphosphine (63 mg, 0.24 mmol, 0.4 eq.), ethanolamine (74 μL, 1.22 mmol, 2.0 eq.), and formic acid (92 μL, 2.44 mmol, 4.0 eq.) were added, and the solution was degassed by bubbling nitrogen gas for 1 min. Tetrakis(triphenylphosphine)-palladium(0) (70 mg, 0.061 mmol, 0.1 eq.) was added, and the solution was stirred at room temperature 1 h. The solution was partitioned between aqueous sodium bicarbonate solution (3 mL) and dichloromethane (20 mL), with the organic layer separated and dried over anhydrous sodium sulfate. The solvent was concentrated in vacuo to afford a viscous oil. This oil was dissolved in dichloromethane (10 mL), cooled to 0° C. then pyridine (59 μL, 0.73 mmol, 1.2 eq.) and n-pentyl chloroformate (106 μL, 0.73 mmol, 1.2 eq.) added, and the solution was stirred at 0° C. for 1 h. The solution was extracted with 1N HCl solution (3 mL) and saturated sodium bicarbonate solution (3 mL). The dichloromethane solution was dried over anhydrous sodium sulfate and concentrated in vacuo to yield a viscous oil. The oil was dissolved in dichloromethane (5 mL), to which was added trifluoroacetic acid (2 mL), and the solution was stirred at room temperature for 1 h. The reaction was concentrated in vacuo to a viscous oil, which was dissolved in 1:1 acetonitrile:water, filtered and purified by preparative HPLC-MS, to provide the title compound (40) as a white powder (33 mg, 13%). $^1$H NMR (CD$_3$OD, 400 MHz): 0.87 (t, 3H), 1.31 (m, 4H), 1.65 (m, 2H), 2.08 (s, 3H), 4.15 (t, 2H), 4.26 (m, 2H), 4.41 (m, 2H), 6.31 (t, 1H), 7.33 (d, 1H), 7.83 (d, 1H). MS (ESI) m/z 420.29 (M+H)$^+$, 418.33 (M−H)$^−$.

6.33: Example 33

β-1-(4-Pentyloxycarbonylamino-2-oxo-1H-pyrimidin-1-yl)-3-O-acetyl-2-deoxy-2,2-difluororibose (41)

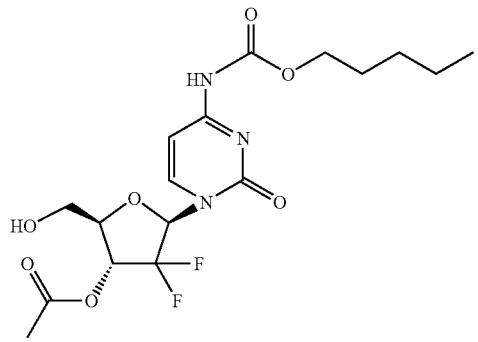

Compound (19) (290 mg, 0.63 mmol, 1.0 eq.) was dissolved in dichloromethane (1 mL), acetic anhydride (297 μL, 3.15 mmol, 5.0 eq.) and pyridine (254 μL, 3.15 mmol, 5.0 eq.) were added, and the reaction was stirred at room temperature for 1 h. The reaction was then concentrated in vacuo, leaving a viscous oil. This oil was dissolved in THF (4 mL), triphenylphosphine (66 mg, 0.25 mmol, 0.4 eq.), ethanolamine (76 μL, 1.26 mmol, 2.0 eq.), and formic acid (95 μL, 2.52 mmol, 4.0 eq.) were added, and the solution was degassed by bubbling nitrogen gas for 1 min. Tetrakis(triphenylphosphine)-palladium(0) (73 mg, 0.063 mmol, 0.1 eq.) was added, and the solution was stirred at room temperature 1 h. The solution was partitioned between aqueous sodium bicarbonate solution (3 mL) and dichloromethane (20 mL), with the organic layer separated and dried over anhydrous sodium sulfate. This oil was dissolved in dichloromethane (10 mL), cooled to 0° C. then pyridine (62 μL, 0.76 mmol, 1.2 eq.) and n-pentyl chloroformate (110 μL, 0.76 mmol, 1.2 eq.) was added, and the solution was stirred at 0° C. for 1 h. The solution was extracted with 1N HCl solution (3 mL) and saturated sodium bicarbonate solution (3 mL). The dichloromethane solution was dried over anhydrous sodium sulfate and concentrated in vacuo to yield a viscous oil. The oil was dissolved in THF (3 mL), triethylamine trihydrofluoride (0.41 mL, 2.52 mmol, 4 eq.) was added, and the solution was stirred at room temperature for 2 days. The reaction solution was concentrated in vacuo to yield a viscous oil, which was dissolved in 1:1 acetonitrile:water, filtered and purified by preparative HPLC to provide the title compound (41) as a white powder (45 mg, 17%). $^1$H NMR (CD$_3$OD, 400 MHz): 0.94 (t, 3H), 1.38 (m, 4H), 1.70 (m, 2H), 2.17 (s, 3H), 3.78 (dd, 1H), 3.94 (dd, 1H), 4.21 (m, 3H), 5.43 (m, 1H), 6.31 (t, 1H), 7.33 (d, 1H), 8.23 (d, 1H). MS (ESI) m/z 420.31 (M+H)$^+$, 418.21 (M−H)$^−$.

6.34: Example 34

β-1-(4-Acetoxymethoxycarbonylamino-2-oxo-1H-pyrimidin-1-yl)-2-deoxy-2,2-difluororibose (2)

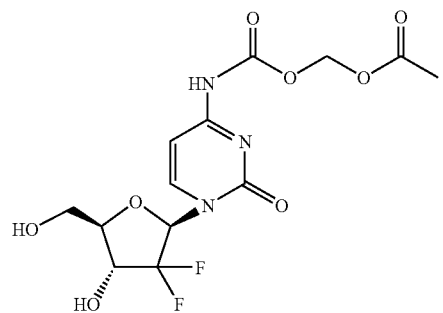

Compound (33) (491 mg, 1 mmol) was dissolved in dichloromethane (10 mL), cooled to 0° C., then pyridine (97 μL, 1.2 mmol, 1.2 eq.) and chloromethyl chloroformate (107 μL, 1.2 mmol, 1.2 eq.) were added, and the solution was stirred at 0° C. for 1 h. The solution was extracted with 1N HCl solution (3 mL) and saturated sodium bicarbonate solution (3 mL). The dichloromethane solution was dried over anhydrous sodium sulfate and concentrated in vacuo to yield a viscous oil. The oil was dissolved in dichloromethane (10 mL), and to the solution was added acetic acid (120 mg, 2 mmol, 2 eq.) and silver carbonate (275 mg, 1 mmol, 1 eq.). The mixture was stirred at room temperature for 2 h. After filtering off the solid, the organic solution was washed with 1N HCl solution (3 mL) and saturated sodium bicarbonate solution (3 mL). The organic layer was concentrated in vacuo to a viscous oil. The oil was dissolved in THF (10 mL), triethylamine trihydrofluoride (0.65 mL, 4 mmol, 4 eq.) was added, and the solution stirred at room temperature for 2 days. The reaction solution was concentrated in vacuo to yield a viscous oil, which was dissolved in 1:1 acetonitrile:water, filtered and purified by preparative HPLC. The title compound (42) was obtained as a white powder (39 mg, 10%). $^1$H NMR (CD$_3$OD, 400 MHz): 2.09 (s, 3H), 3.78 (dd, 1H), 3.96 (m, 2H), 4.29 (m, 1H), 5.80 (s, 2H), 6.23 (t, 1H), 7.27 (d, 1H), 8.34 (d, 1H). MS (ESI) m/z 380.16 (M+H)$^+$, 378.19 (M−H)$^{31}$.

6.35: Example 35

β-1-(4-(1-Isobutanoyloxyethoxy)carbonylamino-2-oxo-1H-pyrimidin-1-yl)-2-deoxy-2,2-difluororibose (43)

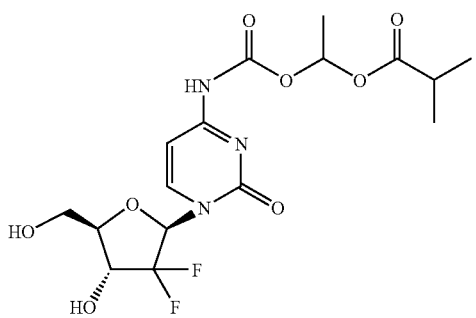

The above compound was prepared in the manner described in Example 34, substituting chloromethyl chloroformate with 1-chloroethyl chloroformate, and substituting acetic acid with isobutyric acid. The title compound (43) was obtained as a white powder (32 mg, 8%). $^1$H NMR (CD$_3$OD, 400 MHz): 1.15 (d, 6H), 1.53 (d, 3H), 2.56 (m, 1H), 3.80 (dd, 1H), 3.96 (m, 2H), 4.29 (m, 1H), 6.24 (t, 1H), 6.84 (q, 1H), 7.27 (d, 1H), 8.33 (d, 1H). MS (ESI) m/z 422.33 (M+H)$^+$, 420.31 (M−H)$^-$.

6.36: Example 36

β-1-(4-(2,6-Dimethylbenzoyl)oxymethoxycarbonylamino-2-oxo-1H-pyrimidin-1-yl)-2-deoxy-2,2-difluororibose (44)

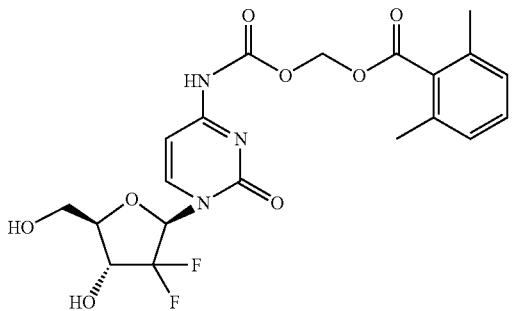

The above compound was prepared in the manner described in Example 34, substituting acetic acid with 2,6-dimethylbenzoic acid. The title compound (44) was obtained as a white powder (31 mg, 7%). $^1$H NMR (CD$_3$OD, 400 MHz): 2.29 (s, 6H), 3.79 (dd, 1H), 3.96 (m, 2H), 4.28 (m, 1H), 6.05 (s, 2H), 7.04 (m, 2H), 7.20 (t, 1H), 7.30 (d, 1H), 8.34 (d, 1H). MS (ESI) m/z 470.28 (M+H)$^+$, 468.32 (M−H)$^-$.

6.37: Example 37

β-1-(4-(2-Methylbenzoyl)oxymethoxycarbonylamino-2-oxo-1H-pyrimidin-1-yl)-2-deoxy-2,2-difluororibose (45)

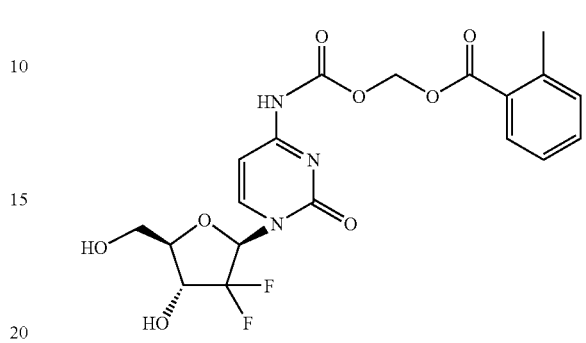

The above compound was prepared in the manner described in Example 34, substituting acetic acid with 2-methylbenzoic acid. The title compound (44) was obtained as a white powder (45 mg, 10%). $^1$H NMR (CD$_3$OD, 400 MHz): 2.58 (s, 3H), 3.79 (dd, 1H), 3.96 (m, 2H), 4.28 (m, 1H), 6.04 (s, 2H), 6.23 (t, 1H), 7.28 (m, 3H), 7.45 (t, 1H), 7.91 (d, 1H), 8.34 (d, 1H). MS (ESI) m/z 456.14 (M+H)$^+$, 454.11 (M−H)$^-$.

6.38: Example 38

β-1-(4-Acetoxymethoxycarbonylamino-2-oxo-1H-pyrimidin-1-yl)-5-O-(L-valinyl)-2-deoxy-2,2-difluororibose (46)

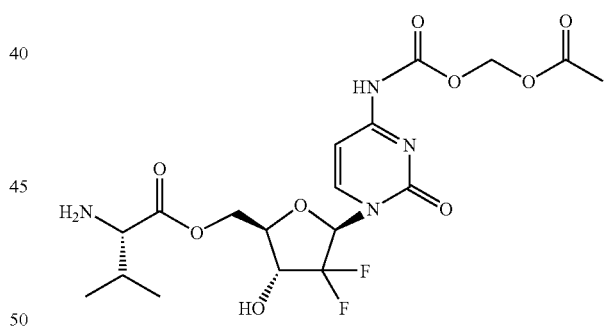

N-tert-Butyloxycarbonyl-L-valine (700 mg, 3.2 mmol, 2.4 eq.) was dissolved in dichloromethane (15 mL). To this solution was added dicyclohexylcarbodiimide (340 mg, 1.6 mmol, 1.2 eq.). Shortly after the addition of dicyclohexylcarbodiimide, a white precipitate formed, the resulting suspension was stirred at room temperature for 2 h, then filtered directly into a separate flask containing a solution of compound (23) (578 mg, 1.34 mmol, 1.0 eq.) and 4-dimethylaminopyridine (20 mg, 0.13 mmol, 0.1 eq.) in dichloromethane (10 mL). This solution was stirred overnight at room temperature, then the crude product was washed with saturated sodium bicarbonate solution (5 mL). The dichloromethane solution was dried over anhydrous sodium sulfate and concentrated in vacuo to yield 440 mg of a viscous oil. The oil was dissolved in THF (15 mL), then triphenylphosphine (42 mg, 0.16 mmol, 0.2 eq.), ethanolamine (98 μL, 1.6 mmol, 2.0 eq.), and formic acid (122 μL, 3.2 mmol, 4.0 eq.) were added, and the solution was degassed by bubbling nitrogen gas for 2 min. Tetrakis(triphenylphosphine)-palladium(0) (92 mg, 0.08 mmol, 0.1 eq.) was added, and the solution was stirred at room temperature 1 h. The solution was partitioned between aqueous sodium bicarbonate solution (3 mL) and dichloromethane (20 mL), with the organic layer separated and dried over anhydrous sodium sulfate. The reaction solution was concentrated in vacuo to yield a viscous oil, which was dissolved in dichloromethane (6 mL) and cooled to 0° C. To the solution was added pyridine (78 μL, 0.96 mmol, 1.2 eq.) and chloromethyl chloroformate (85 μL, 0.96 mmol, 1.2 eq.) and stirred at 0° C. for 1 h. The solution was extracted with 1N HCl solution (3 mL) and saturated sodium bicarbonate solution (3 mL). The dichloromethane solution was dried over anhydrous sodium sulfate and concentrated in vacuo to yield a viscous oil. The oil was dissolved in dichloromethane (5 mL), and to the solution was added acetic acid (96 mg, 1.6 mmol, 2 eq.) and silver carbonate (220 mg, 0.8 mmol, 1 eq.). The mixture was stirred at room temperature for 2 h. After filtering off the solid, the organic solution was washed with 1N HCl solution (3 mL) and saturated sodium bicarbonate solution (3 mL). The organic layer was concentrated in vacuo to a viscous oil. The oil was dissolved in dichloromethane (3 mL) and treated with trifluoroacetic acid (1 mL) at room temperature for 1 h. The reaction was concentrated in vacuo to yield a viscous oil, which was dissolved in 1:1 acetonitrile:water, filtered and purified by preparative HPLC to provide the title compound (46) as a white powder (38 mg, 6%). $^1$H NMR (CD$_3$OD, 400 MHz): 1.08 (d, 6H), 2.11 (s, 3H), 4.05 (d, 1H), 4.23 (m, 1H), 4.33 (m, 1H), 4.64 (d, 2H), 5.83 (s, 2H), 6.21 (t, 1H), 7.28 (d, 1H), 7.99 (d, 1H). MS (ESI) m/z 479.25 (M+H)$^+$, 477.21 (M−H)$^−$.

6.39: Example 39

β-1-{[4-((2S)-((2S)-Aminopropionylamino)-2-carboxy)ethoxycarbonylamino]-2-oxo-1H-pyrimidin-1-yl}-2-deoxy-2,2-difluororibose (47)

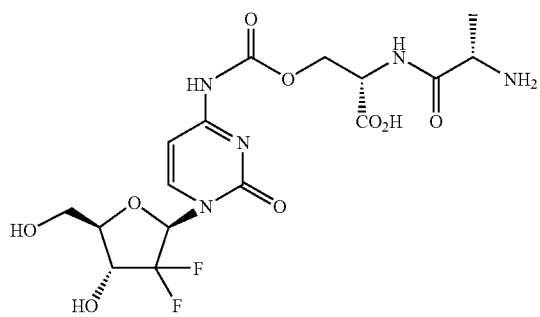

Compound (33) (491 mg, 1 mmol, 1 eq.) was dissolved in dichloromethane (5 mL), cooled to 0° C. then pyridine (324 μL, 4 mmol, 4 eq.) and a 1.93 M solution of phosgene in toluene (2.07 mL, 4 mmol, 4 eq.) were added, and the solution was stirred at 0° C. for 1 h. The solvent was removed in vacuo, leaving a viscous oil, which was dissolved in toluene (10 mL). Boc-Ala-Ser-O-t-Butyl (368 mg, 1.0 mmol, 1.0 eq.) was added and the solution was heated at 95° C. for 2 h. The solution was concentrated in vacuo to yield a viscous oil. The oil was dissolved in THF (10 mL), triethylamine trihydrofluoride (0.65 mL, 4 mmol, 4 eq.) was added, and the solution was stirred at room temperature for 2 days. The reaction solution was concentrated in vacuo to yield a viscous oil. The oil was stirred with dichloromethane (3 mL) and trifluoroacetic acid (3 mL) at room temperature for 3 h. The reaction solution was concentrated in vacuo to yield a viscous oil, which was dissolved in 1:1 acetonitrile: water, filtered and purified by preparative HPLC to provide the title compound (47) as a white powder (121 mg, 26%). $^1$H NMR (CD$_3$OD, 400 MHz): 1.39 (d, 3H), 3.78 (dd, 2H), 3.95 (m, 2H), 4.18 (m, 1H), 4.42 (m, 2H), 4.62 (t, 1H), 6.06 (t, 1H), 7.00 (d, 1H), 8.00 (d, 1H). MS (ESI) m/z 466.15 (M+H)$^+$, 464.11 (M−H)$^−$.

6.40: Example 40

β-1-{[4-((2S)-((2S)-Amino-3,3-dimethylbutyroylamino)-2-carboxy)ethoxycarbonylamino]-2-oxo-1H-pyrimidin-1-yl}-2-deoxy-2,2-difluororibose (48)

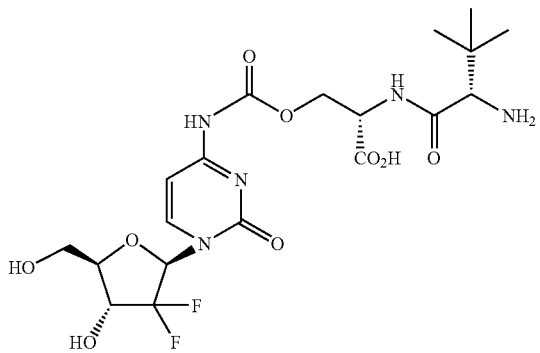

The above compound was prepared in the manner described in Example 39, substituting Boc-Ala-Ser-O-t-Butyl with Boc-2-t-Butyl-Gly-Ser-O-t-Butyl. The title compound (48) was obtained as a white powder (91 mg, 16%). $^1$H NMR (CD$_3$OD, 400 MHz): 1.11 (s, 9H), 3.72 (s, 1H), 3.81 (dd, 1H), 3.95 (m, 2H), 4.28 (m, 1H), 4.47 (m, 1H), 4.56 (m, 2H), 6.21 (t, 1H), 7.24 (d, 1H), 8.30 (d, 1H). MS (ESI) m/z 508.01 (M+H)$^+$, 506.04 (M−H)$^−$.

6.41: Example 41

β-1-{[4-((2S)-(Aminoacetylamino)-2-carboxy)ethoxycarbonylamino]-2-oxo-1H-pyrimidin-1-yl}-2-deoxy-2,2-difluororibose (49)

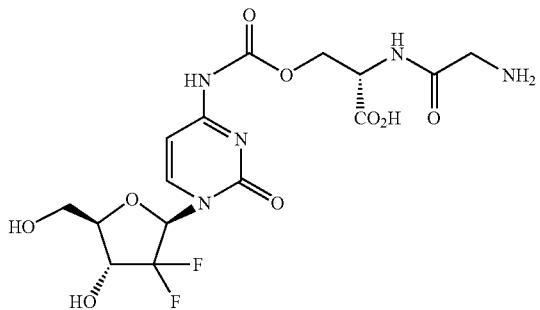

The above compound was prepared in the manner described in Example 39, substituting Boc-Ala-Ser-O-t-

Butyl with Boc-Gly-Ser-O-t-Butyl. The title compound (49) was obtained as a white powder (140 mg, 31%). $^1$H NMR (CD$_3$OD, 400 MHz): 3.79 (m, 3H), 3.95 (m, 2H), 4.28 (m, 1H), 4.55 (dd, 2H), 4.85 (t, 1H), 6.23 (t, 1H), 7.26 (d, 1H), 8.32 (d, 1H). MS (ESI) m/z 451.97 (M+H)$^+$, 450.01 (M−H)$^-$.

6.42: Example 42

β-1-{[4-((2S)-((2S)-Aminophenacetylamino)-2-carboxy)ethoxycarbonylamino]-2-oxo-1H-pyrimidin-1-yl}-2-deoxy-2,2-difluororibose (50)

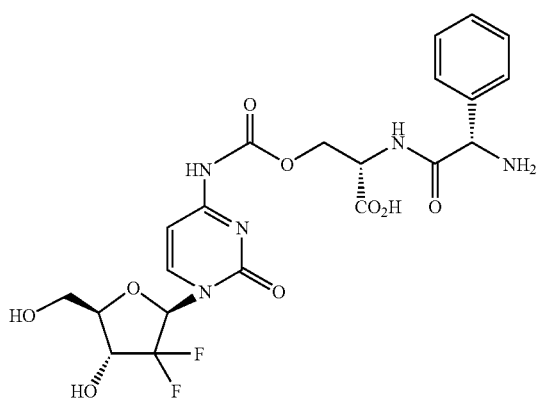

The above compound was prepared in the manner described in Example 39, substituting Boc-Ala-Ser-O-t-Butyl with Boc-Phg-Ser-O-t-Butyl. The title compound (50) was obtained as a white powder (140 mg, 31%). $^1$H NMR (CD$_3$OD, 400 MHz): 3.74 (dd, 2H), 3.91 (m, 1H), 4.15 (m, 1H), 4.29 (q, 1H), 4.49 (m, 2H), 4.97 (s, 1H), 6.05 (t, 1H), 6.76 (d, 1H), 7.19 (m, 5H), 8.04 (d, 1H). MS (ESI) m/z 528.10 (M+H)$^+$, 526.17 (M−H)$^-$.

6.43: Example 43

β-1-{[4-((2S)-(2-Amino-2-methylpropionylamino)-2-carboxy)ethoxycarbonylamino]-2-oxo-1H-pyrimidin-1-yl}-2-deoxy-2,2-difluororibose (51)

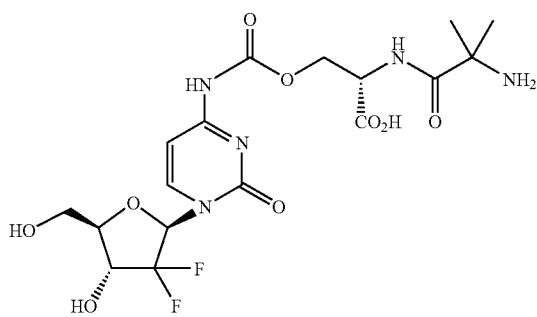

The above compound was prepared in the manner described in Example 39, substituting Boc-Ala-Ser-O-t-Butyl with Boc-Aib-Ser-O-t-Butyl. The title compound (51) was obtained as a white powder (81 mg, 17%). $^1$H NMR (CD$_3$OD, 400 MHz): 1.45 (d, 6H) 3.79 (dd, 2H), 3.95 (m, 1H), 4.20 (m, 1H), 4.324.48 (m, 3H), 6.09 (t, 1H), 7.09 (d, 1H), 8.01 (d, 1H). MS (ESI) m/z 480.10 (M+H)$^+$, 478.07 (M−H)$^-$.

6.44: Example 44

β-1-{[4-((2S)-(1-Amino-cyclohexanecarbonylamino)-2-carboxy)ethoxycarbonylamino]-2-oxo-1H-pyrimidin-1-yl}-2-deoxy-2,2-difluororibose (52)

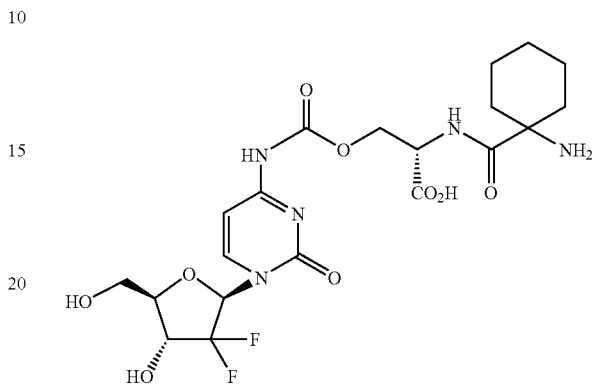

The above compound was prepared in the manner described in Example 39, substituting Boc-Ala-Ser-O-t-Butyl with Boc-1-amino cyclohexane carboxylic-Ser-O-t-Butyl. The title compound (52) was obtained as a white powder (77 mg, 15%). $^1$H NMR (CD$_3$OD, 400 MHz): 1.21-2.04 (m, 10H), 3.76 (dd, 2H), 3.95 (m, 1H), 4.20 (m, 1H), 4.35-4.50 (m, 3H), 6.09 (t, 1H), 7.06 (d, 1H), 8.02 (d, 1H). MS (ESI) m/z 520.14 (M+H)$^+$, 518.14 (M−H)$^-$.

6.45: Example 45

β-1-(4-(2-Acetoxyethoxy)carbonylamino-2-oxo-1H-pyrimidin-1-yl)-2-deoxy-2,2-difluororibose (53)

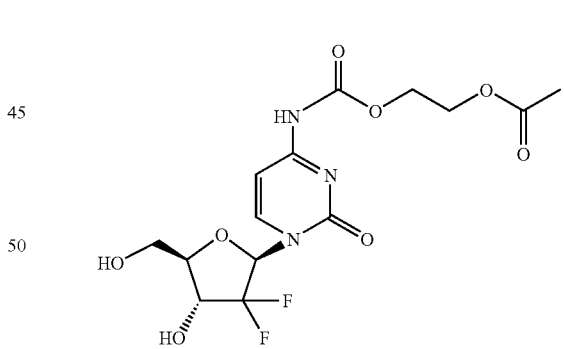

Compound (33) (491 mg, 1 mmol, 1 eq.) was dissolved in dichloromethane (5 mL), cooled to 0° C., then pyridine (324 μL, 4 mmol, 4 eq.) and a solution of 1.93 M phosgene in toluene (2.07 mL, 4 mmol, 4 eq.) were added, and the solution was stirred at 0° C. for 1 h. The reaction solvent was concentrated in vacuo to a viscous oil, which was dissolved in toluene (10 mL). To this was added 2-hydroxyethyl acetate (208 mg, 2.0 mmol, 2.0 eq.) and the solution was heated at 90° C. for 1 h. The solution was concentrated in vacuo to yield a viscous oil. The oil was dissolved in THF (10 mL), triethylamine trihydrofluoride (0.65 mL, 4 mmol,

6.46: Example 46

β-1-(4-(2-Pivaloyloxyethoxy)carbonylamino-2-oxo-1H-pyrimidin-1-yl)-2-deoxy-2,2-difluororibose (54)

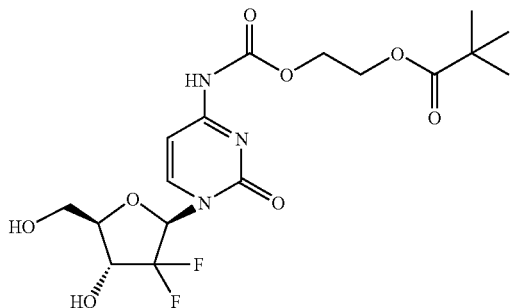

The above compound was prepared in the manner described in Example 45, substituting 2-hydroxyethyl acetate with 2-hydroxyethyl 2,2-dimethylpropanoate. The title compound (54) was obtained as a white powder (170 mg, 39%). $^1$H NMR (CD$_3$OD, 400 MHz): 1.21-1.47 (m, 5H), 1.63 (m, 1H), 1.73 (m, 2H), 1.88 (m, 1H), 2.33 (m, 1H), 3.78-3.99 (m 3H), 4.25-4.42 (m, 5H), 6.24 (t, 1H), 7.29 (d, 1H), 8.32 (d, 1H). MS (ESI) m/z 436.28 (M+H)$^+$, 434.31 (M−H)$^−$.

6.47: Example 47

β-1-(4-(2-Cyclohexanecarboxyethoxy)carbonylamino-2-oxo-1H-pyrimidin-1-yl)-2-deoxy-2,2-difluororibose (55)

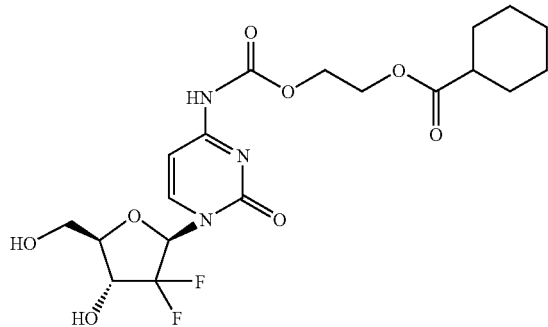

The above compound was prepared in the manner described in Example 45, substituting 2-hydroxyethyl acetate with 2-hydroxyethyl cyclohexanecarboxylate. The title compound (55) was obtained as a white powder (202 mg, 44%). $^1$H NMR (CD$_3$OD, 400 MHz): 1.19 (s, 9H), 3.73 (m, 1H), 3.81 (dd, 1H), 3.97 (m, 1H), 4,10 (m, 1H), 4.32 (m, 2H), 4.42 (m, 2H), 6.24 (t, 1H), 7.29 (d, 1H), 8.32 (d, 1H) MS (ESI) m/z 462.27 (M+H)$^+$, 460.17 (M−H)$^−$.

6.48: Example 48

β-1-{[14-(2-((2S)-Amino-3-methylbutyroylamino)-ethoxycarbonylamino]-2-oxo-1H-pyrimidin-1-yl}-2-deoxy-2,2-difluororibose (56)

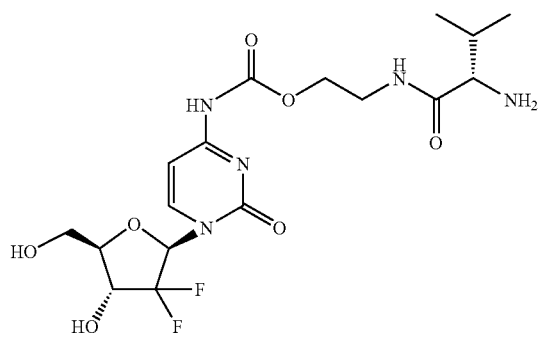

Compound (33) (491 mg, 1 mmol, 1 eq.) was dissolved in dichloromethane (5 mL), cooled to 0° C., then pyridine (324 µL, 4 mmol, 4 eq.) and a solution of 1.93 M phosgene in toluene (2.07 mL, 4 mmol, 4 eq.) were added, and the solution was stirred at 0° C. for 1 h. The reaction solvent was concentrated in vacuo to a viscous oil, which was dissolved in toluene (10 mL). To this was added (2S)-2-tert-butoxycarbonylamino-N-(2-hydroxyethyl)-3-methylbutanamide (320 mg, 2.0 mmol, 2.0 eq.) and the solution was heated at 90° C. for 1 h. The solution was concentrated in vacuo to yield a viscous oil. The oil was dissolved in THF (10 mL), triethylamine trihydrofluoride (0.65 mL, 4 mmol, 4 eq.) was added, and the solution was stirred at room temperature for 2 days. The reaction solution was concentrated in vacuo to Yield a viscous oil, which was dissolved in dichloromethane (3 mL) and trifluoroacetic acid (3 mL), and stirred at room temperature for 1 h. The solution was concentrated in vacuo to yield a viscous oil, which was dissolved in 1:1 acetonitrile:water, filtered and purified by preparative HPLC to provide the title compound (56) as a white powder (148 mg, 33%). $^1$H NMR (CD$_3$OD, 400 MHz): 1.04 (t, 6H), 2.16 (m, 1H), 3.50 (m, 1H), 3.65 (m, 2H), 3.80 (dd, 1H), 3.95 (m, 2H), 4.28 (m, 3H), 6.23 (t, 1H), 7.27 (d, 1H), 8.31 (d, 1H). MS (ESI) m/z 450.23 (M+H)$^+$, 448.21 (M−H)$^−$.

6.49: Example 49

β-{[4-(2-((2S)-Amino-3-phenylpropionylamino)-ethoxcarbonylamino]-2-oxo-1H-pyrimidin-1-yl}-2-deoxy-2,2-difluororibose (57)

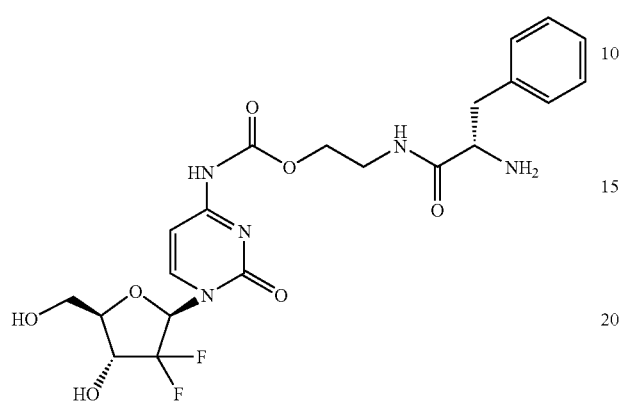

The above compound was prepared in the manner described in Example 48, substituting (2S)-2-tert-butoxycarbonylamino-N-(2-hydroxyethyl)-3-methylbutanamide with (2S)-2-tert-butoxycarbonylamino-N-(2-hydroxyethyl) phenylpropanamide. The title compound obtained (57) was obtained as a white powder (154 mg, 31%). $^1$H NMR (CD$_3$OD, 400 MHz): 3.05 (m, 1H), 3.16 (m, 1H), 3.40 (m, 1H), 3.59 (m, 1H), 3.80 (m, 1H), 3.95 (m, 2H), 4.03 (m, 1H), 4.14 (m, 2H), 4.28 (m 1H), 6.23 (t, 1H), 7.29 (m, 6H), 8.30 (d, 1H). MS (ESI) m/z 498.25 (M+H)$^+$, 496.23 (M−H)$^−$.

6.50: Example 50

β-1-{[4-(2-(Phenyloxycarbonylamino)-ethoxycarbonylamino]-2-oxo-1H-pyrimidin-1-yl}-2-deoxy-2,2-difluororibose (58)

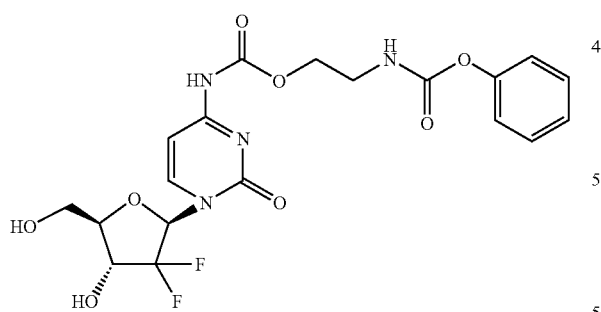

Compound (33) (491 mg, 1 mmol, 1 eq.) was dissolved in dichloromethane (5 mL), cooled to 0° C., then pyridine (324 μL, 4 mmol, 4 eq.) and a solution of 1.93 M phosgene in toluene (2.07 mL, 4 mmol, 4 eq.) were added, and the solution was stirred at 0° C. for 1 h. The reaction solvent was concentrated in vacuo to a viscous oil, which was dissolved in toluene (10 mL). To this was added N-(2-hydroxyethyl)-phenoxycarboxamide (362 mg, 2.0 mmol, 2.0 eq.) and the solution was heated at 90° C. for 1 h. The solution was concentrated in vacuo to yield a viscous oil. The oil was dissolved in THF (10 mL), triethylamine trihydrofluoride (0.65 mL, 4 mmol, 4 eq.) was added, and the solution was stirred at room temperature for 2 days. The reaction solution was concentrated in vacuo to yield a viscous oil, which was dissolved in 1:1 acetonitrile:water, filtered and purified by preparative HPLC to provide the title compound (58) as a white powder (179 mg, 38%). $^1$H NMR (CD$_3$OD, 400 MHz): 3.49 (t, 2H), 3.79 (m, 1H), 3.96 (m 2H), 4.28 (m, 3H), 6.24 (t, 1H), 7.07 (d, 2H), 7.18 (t, 1H), 7.33 (m, 3H), 8.31 (d, 1H). MS (ESI) m/z 471.02 (M+H)$^+$, 468.97 (M−H)$^−$.

6.51: Example 51

β-1-{[4-(3-(Benzyloxycarbonylamino)-propoxycarbonylamino]-2-oxo-1H-pyrimidin-1-yl}-2-deoxy-2,2-difluororibose (59)

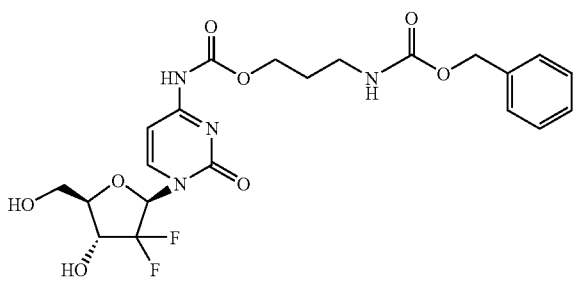

The above compound was prepared in the manner described in Example 50, substituting N-(2-hydroxyethyl)-phenoxycarboxamide with N-(3-hydroxypropyl)-benzyloxycarboxamide. The title compound obtained (59) was obtained as a white powder (159 mg, 32%). $^1$H NMR (CD$_3$OD, 400 MHz): 3.24 (t, 2H), 3.79 (m, 1H), 3.95 (m, 2H), 4.26 (m, 3H), 5.03 (s, 2H), 6.23 (t, 1H), 7.29 (m, 6H), 8.31 (d, 1H). MS (ESI) m/z 499.18 (M+H)$^+$, 496.98 (M−H)$^−$.

6.52: Example 52

β-1-[4-(2-Dimethylamino-ethoxycarbonylamino)-2-oxo-1H-pyrimidin-1-yl]-2-deoxy-2,2-difluororibose (60)

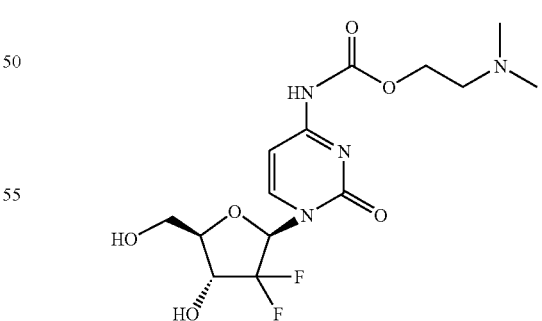

The above compound was prepared in the manner described in Example 50, substituting N-(2-hydroxyethyl)-phenoxycarboxamide with N,N-dimethylethanolamine. dimethylethanolamine. The title compound obtained (60) was obtained as a colorless oil (76 mg, 20%). $^1$H NMR (CD$_3$OD, 400 MHz): 3.00 (s, 6H), 3.55 (m, 2H), 3.80 (dd, 1H), 3.96 (m, 2H), 4.30 (m, 1H), 4.56 (dd, 2H), 6.23 (t, 1H), 7.17 (d, 1H), 8.31 (d, 1H). MS (ESI) m/z 379.32 (M+H)⁺, 377.29 (M−H)⁻.

6.53: Example 53

β-1-[4-(4-Acetoxybutyroylamino)-2-oxo-1H-pyrimidin-1-yl]-2-deoxy-2,2-difluororibose (61)

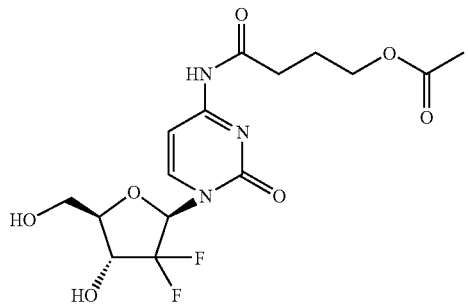

Compound (33) (491 mg, 1 mmol) was dissolved dichloromethane in (15 mL), cooled to 0° C., then pyridine (97 μL, 1.2 mmol, 1.2 eq.) and 4-acetoxybutyroyl chloride (180 mg, 1.2 mmol, 1.2 eq.) were added, and the solution was stirred at 0° C. for 1 h. The solution was extracted with 1N HCl solution (3 mL) and saturated sodium bicarbonate solution (3 mL) then dried over anhydrous sodium sulfate and concentrated in vacuo to yield a viscous oil. The oil was dissolved in THF (10 mL), triethylamine trihydrofluoride (0.65 mL, 4 mmol, 4 eq.) was added, and the solution was stirred at room temperature for 2 days. The reaction solution was concentrated in vacuo to yield a viscous oil, which was dissolved in 1:1 acetonitrile:water, filtered and purified by preparative HPLC to provide the title compound (61) as a white powder (152 mg, 39%). ¹H NMR (CD₃OD, 400 MHz): 1.99 (m, 5H), 2.55 (t, 2H), 3.79 (m, 1H), 3.95 (m, 2H), 4.11 (t, 2H), 4.28 (m, 1H), 6.24 (t, 1H), 7.44 (d, 1H), 8.33 (d, 1H). MS (ESI) m/z 392.19 (M+H)⁺, 390.17 (M−H)⁻.

6.54: Example 54

β-1-[4-(4-Pivaloyloxybutyroylamino)-2-oxo-1H-pyrimidin-1-yl]-2-deoxy-2,2-difluororibose (62)

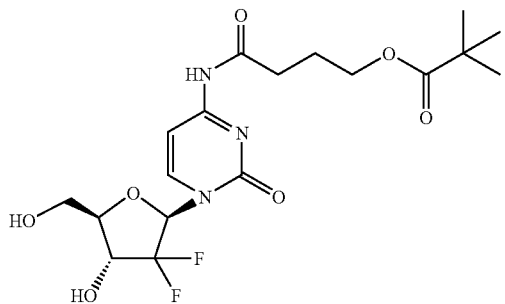

The above compound was prepared in the manner described in Example 53, substituting 4-acetoxybutyroyl chloride with 4-pivaloyloxybutyroyl chloride. The title compound obtained (62) was obtained as a white powder (165 mg, 38%). ¹H NMR (CD₃OD, 400 MHz): 1.17 (s, 9H), 2.00 (m, 2H), 2.57 (t, 2H), 3.80 (dd, 1H), 3.96 (m, 2H), 4.11 (t, 2H), 4.29 (m 1H), 6.24 (t, 1H), 7.43 (d, 1H), 8.34 (d, 1H). MS (ESI) m/z 434.31 (M+H)⁺, 432.35 (M−H)⁻.

6.55: Example 55

β-1-{[4-(2-((1-Pivaloyloxy-2,2-dimethylpropyl)oxycarbonylamino)-ethoxycarbonylamino]-2-oxo-1H-pyrimidin-1-yl}-2-deoxy-2,2-difluororibose (63)

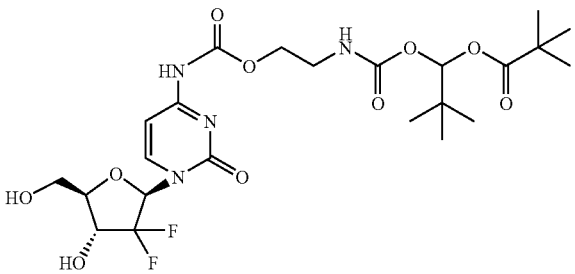

Compound (33) (491 mg, 1 mmol, 1 eq.) was dissolved in dichloromethane (5 mL), cooled to 0° C., then pyridine (324 μL, 4 mmol, 4 eq.) and a solution of 1.93 M phosgene in toluene (2.07 mL, 4 mmol, 4 eq.) were added, and the solution was stirred at 0° C. for 1 h. The reaction solvent was concentrated in vacuo to a viscous oil, which was dissolved in toluene (10 mL). To this was added 1-[N-(2-hydroxyethyl)carbamoyloxy]-2,2-dimethylpropyl 2,2-dimethylpropanoate (550 mg, 2.0 mmol, 2.0 eq.) and the solution was heated at 90° C. for 1 h. The solution was concentrated in vacuo to yield a viscous oil. The oil was dissolved in THF (10 mL), triethylamine trihydrofluoride (0.65 mL, 4 mmol, 4 eq.) was added, and the solution was stirred at room temperature for 2 days. The reaction solution was concentrated in vacuo to yield a viscous oil, which was dissolved in 1:1 acetonitrile:water, filtered and purified by preparative HPLC to provide the title compound (63) as a white powder (147 mg, 26%). ¹H NMR (CD₃OD, 400 MHz): 0.96 (s, 9H), 1.17 (s, 9H), 3.40 (t, 2H), 3.80 (m, 1H), 3.97 (m, 2H), 4.26 (m, 3H), 6.24 (t, 1H), 6.41 (s, 1H), 7.26 (d, 1H), 8.32 (d, 1H). MS (ESI) m/z 565.45 (M+H)⁺, 563.42 (M−H)⁻.

6.56: Example 56

β-1-{[4-(2-((1-Pivaloyloxy-2,2-dimethylpropyl)oxycarbonylmethylamino)-ethoxycarbonylamino]-2-oxo-1H-pyrimidin-1-yl}-2-deoxy-2,2-difluororibose (64)

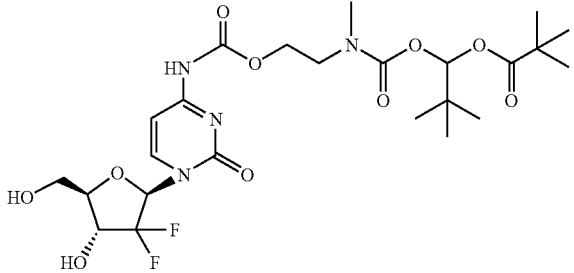

The above compound was prepared in the manner described in Example 55, substituting 1-[N-(2-hydroxyethyl)carbamoyloxy]-2,2-dimethylpropyl 2,2-dimethylpropanoate with 1-[N-(2-hydroxyethyl)-N-methylcarbamoyloxy]-2,2-dimethylpropyl 2,2-dimethylpropanoate. The title compound obtained (64) was obtained as a white powder (210 mg, 36%). $^1$H NMR (CD$_3$OD, 400 MHz): 0.97 (s, 9H), 1.17 (s, 9H), 3.00 and 2.99 (2s, 3H), 3.61 (m, 2H), 3.81 (dd, 1H), 3.98 (d, 2H), 4.34 (m, 3H), 6.25 (t, 1H), 6.40 (d, 1H), 7.27 (dd, 1H), 8.38 (dd, 1H). MS (ESI) m/z 579.48 (M+H)$^+$, 577.45 (M–H)$^-$.

6.57: Example 57

β-1-{[4-(2-((1-Acyloxyalkyl)oxycarbonylamino)-ethoxycarbonylamino]-2-oxo-1H-pyrimidin-1-yl}-2-deoxy-2,2-difluororibose (65)-(72)

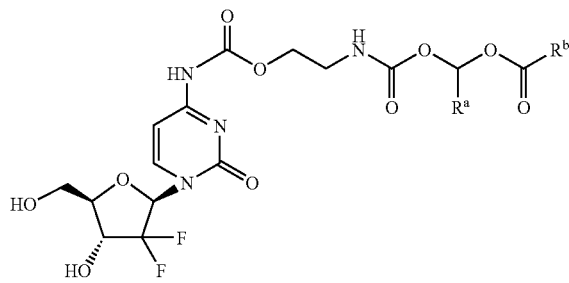

The following additional compounds were prepared following the procedure described in Example 55:

β-1-{[4-(2-((Isobutanoyloxymethyl)oxycarbonylamino)-ethoxycarbonylamino]-2-oxo-1H-pyrimidin-1-yl}-2-deoxy-2,2-difluororibose (65);

β-1-{[4-(2-((Acetoxymethyl)oxycarbonylamino)-ethoxycarbonylamino]-2-oxo-1H-pyrimidin-1-yl}-2-deoxy-2,2-difluororibose (66);

β-1-{[4-(2-((1-Isobutanoyloxyethyl)oxycarbonylamino)-ethoxycarbonylamino]-2-oxo-1H-pyrimidin-1-yl}-2-deoxy-2,2-difluororibose (67);

β-1-{[4-(2-((1-Acetoxy-2-methylpropyl)oxycarbonylamino)-ethoxycarbonylamino]-2-oxo-1H-pyrimidin-1-yl}-2-deoxy-2,2-difluororibose (68);

β-1-{[4-(2-((1-Isobutanoyloxy-2-methylpropyl)oxycarbonylamino)-ethoxycarbonylamino]-2-oxo-1H-pyrimidin-1-yl}-2-deoxy-2,2-difluororibose (69);

β-1-{[4-(2-((1-Pivaloyloxy-2-methylpropyl)oxycarbonylamino)-ethoxycarbonylamino]-2-oxo-1H-pyrimidin-1-yl}-2-deoxy-2,2-difluororibose (70);

β-1-{[4-(2-((1-Pivaloyloxyethyl)oxycarbonylamino)-ethoxycarbonylamino]-2-oxo-1H-pyrimidin-1-yl}-2-deoxy-2,2-difluororibose (71); and β-1-{[4-(2-((1-Acetoxyethyl)oxycarbonylamino)-ethoxycarbonylamino]-2-oxo-1H-pyrimidin-1-yl}-2-deoxy-2,2-difluororibose (72).

6.58: Example 58

β-1-{[4-(2-((1-Acyloxyalkyl)oxycarbonylmethylamino)-ethoxycarbonylamino]-2-oxo-1H-pyrimidin-1-yl}-2-deoxy-2,2-difluororibose (73)-(82)

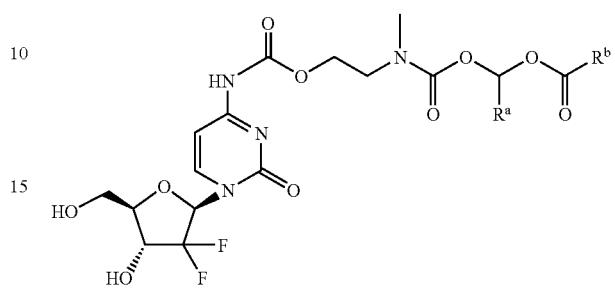

The following additional compounds were prepared following the procedure described in Example 56:

β-1-{[4-(2-((Acetoxymethyl)oxycarbonylmethylamino)-ethoxycarbonylamino]-2-oxo-1H-pyrimidin-1-yl}-2-deoxy-2,2-difluororibose (73);

β-1-{[4-(2-((1-Isobutanoyloxyethyl)oxycarbonylmethylamino)-ethoxycarbonylamino]-2-oxo-1H-pyrimidin-1-yl}-2-deoxy-2,2-difluororibose (74);

β-1-{[4-(2-((1-Acetoxy-2-methylpropyl)oxycarbonylmethylamino)-ethoxycarbonylamino]-2-oxo-1H-pyrimidin-1-yl}-2-deoxy-2,2-difluororibose (75);

β-1-{[4-(2-((1-Isobutanoyloxy-2-methylpropyl)oxycarbonylmethylamino)-ethoxycarbonylamino]-2-oxo-1H-pyrimidin-1-yl}-2-deoxy-2,2-difluororibose (76);

β-1-{[4-(2-((1-Pivaloyloxy-2-methylpropyl)oxycarbonylmethylamino)-ethoxycarbonylamino]-2-oxo-1H-pyrimidin-1-yl}-2-deoxy-2,2-difluororibose (77);

β-1-{[4-(2-((1-Pivaloyloxyethyl)oxycarbonylmethylamino)-ethoxycarbonylamino]-2-oxo-1H-pyrimidin-1-yl}-2-deoxy-2,2-difluororibose (78);

β-1-{[4-(2-((1-Acetoxyethyl)oxycarbonylmethylamino)-ethoxycarbonylamino]-2-oxo-1H-pyrimidin-1-yl}-2-deoxy-2,2-difluororibose (79);

β1-{[4-(2-((1-(2,6-Dimethylbenzoyl)oxymethyl)oxycarbonylmethylamino)-ethoxycarbonylamino]-2-oxo-1H-pyrimidin-1-yl}-2-deoxy-2,2-difluororibose (80);

β-1-{[4-(2-((1-(2,6-Dimethylbenzoyl)oxy-2-methylpropyl)oxycarbonylmethylamino)-ethoxycarbonylamino]-2-oxo-1H-pyrimidin-1-yl}-2-deoxy-2,2-difluororibose (81); and β-1-{[4-(2-((1-(2-Methylbenzoyl)oxy-2-methylpropyl)oxycarbonylmethylamino)-ethoxycarbonylamino]-2-oxo-1H-pyrimidin-1-yl}-2-deoxy-2,2-difluororibose (82)

6.59: Example 59

In Vitro Compound Transport Assays with PEPT1 and PEPT2-Expressing Cell Lines (a) Inhibition of Radiolabeled Gly-Sar Uptake Rat and human PEPT1 and PEPT2 expressing CHO cell lines were prepared as described in PCT Application WO01/20331. Amino acid ester conjugates of gemcitabine, i.e. compounds (3)-(10), (14) and (18), were evaluated for interaction with the peptide transporters using a radiolabeled substrate uptake assay in a competitive inhibition format, as described in International Publication No. WO01/20331.

Transport-induced currents were also measured in *Xenopus* oocytes transfected with rat and human PEPT1 and PEPT2.

(b) Analysis of Electrogenic Transport in *Xenopus* Oocytes
RNA Preparation:

Rat and human PEPT1 and PEPT2 transporter cDNAs were subcloned into a modified pGEM plasmid that contains 5' and 3' untranslated sequences from the *Xenopus* β-actin gene. These sequences increase RNA stability and protein expression. Plasmid cDNA was linearized and used as template for in vitro transcription (Epicentre Technologies transcription kit, 4:1 methylated:non-methylated GTP).

*Xenopus* Oocyte Isolation.

*Xenopus laevis* frogs were anesthetized by immersion in Tricaine (1.5 g/mL in deionized water) for 15 minutes. Oocytes were removed and digested in frog ringer solution (90 mM NaCl, 2 mM KCl, 1 mM $MgCl_2$, 10 mM NaHEPES, pH 7.45, no $CaCl_2$) with 1 mg/mL collagenase (Worthington Type 3) for 80-100 minutes with shaking. The oocytes were washed 6 times, and the buffer changed to frog ringer solution containing $CaCl_2$ (1.8 mM). Remaining follicle cells were removed if necessary. Cells were incubated at 16° C., and each oocyte injected with 10-20 µg RNA in 45 µL solution.

Electrophysiology Measurements.

Transport currents were measured 1-4 days after injection, using a standard two-electrode electrophysiology set-up (Geneclamp 500 amplifier, Digidata 1320/PCLAMP software and ADInstruments hardware and software were used for signal acquisition). Electrodes (2-4 mΩ)) were microfabricated using a Sutter Instrument puller and filled with 3M KCl. The bath was directly grounded (transporter currents were less than 0.3 µA). Bath flow was controlled by an automated perfusion system (ALA Scientific Instruments, solenoid valves).

For transporter pharmacology, oocytes were clamped at −60 to −90 mV, and continuous current measurements acquired using PowerLab Software and an ADInstruments digitizer. Current signals were lowpass filtered at 20 Hz and acquired at 4-8 Hz. All bath and drug-containing solutions were frog ringers solution containing $CaCl_2$. Drugs were applied for 10-30 seconds until the induced current reached a new steady-state level, followed by a control solution until baseline currents returned to levels that preceded drug application. The difference current (baseline subtracted from peak current during drug application) reflected the net movement of charge resulting from electrogenic transport and was directly proportional to transport rate. Recordings were made from a single oocyte for up to 60 minutes, enabling 30-40 separate compounds to be tested per oocyte. Compound-induced currents were saturable and gave half-maximal values at substrate concentrations comparable to radiolabel competition experiments. To compare results between oocytes expressing different levels of transport activity, a saturating concentration of glycyl-sarcosine (1 mM) was used as a common reference to normalize results from test compounds. Using this normalization procedure $I_{max}$ (i.e. maximal induced current) for different compounds tested on different oocytes could be compared.

Each of the compounds (3)-(10), (18) and (47) elicited PEPT-specific currents significantly above background (at least 1% of $I_{max}$ for Gly-Sar) when tested at 1 mM on oocytes expressing either PEPT1 or PEPT2, confirming that these compounds serve as substrates for one or both of these transporters.

6.60: Example 60

Experimental Methods for Measurement of SMVT Transport Activity

1. Transporter Cloning

The complete open reading frame of human SMVT (SLC5A6) was amplified from human cDNA prepared from intestinal mRNA. Gene-specific oligonucleotide primers were designed against Genbank sequences (NM-021095). Amplified PCR products were cloned into a modified version of the mammalian expression vector pcDNA3 (termed pMO) that was engineered to contain the 5' and 3' untranslated regions from the *Xenopus* beta-globin gene. All clones were completely sequenced and tested for function by transient transfection in HEK293 cells.

2. *Xenopus* Oocyte Expression and Electrophysiology cRNA for oocyte expression was prepared by linearization of plasmid cDNA and in vitro transcription using T7 polymerase (Epicentre Ampliscribe kit). *Xenopus* oocytes were prepared and maintained as previously described (Collins et al., *PNAS* 13:5456-5460 (1997)) and injected with 10-30 ng RNA. Transport currents were measured 2-6 days later using two-electrode voltage-clamp (Axon Instruments). All experiments were performed using a modified oocyte ringers solution (90 mM NaCl, 2 mM KCl, 1.8 mM CaCl2, 1 mM MgCl2, and 10 mM NaHEPES, pH 7.4; in $Na^+$-free solutions 90 mM choline chloride was substituted for NaCl). The membrane potential of oocytes was held at −60 mV and current traces acquired using PowerLab software (ADInstruments). Full 7-concentration dose-responses were performed for each compound. Current responses at the highest concentration were normalized to the maximal biotin elicited currents (i.e. at 1 mM). Half-maximal concentrations were calculated using non-linear regression curve fitting software (Prism) with the Hill co-efficient fixed to 1. To ensure that currents were specific for the overexpressed transporter, all compounds were tested against uninjected oocytes. Since SMVT requires $Na^+$ for transport, we confirmed transport specificity by application of the compounds in a $Na^+$-free solution.

6.61: Example 61

In Vitro Compound Transport Assays with CNT1, CNT2, CNT3, ENT1 and ENT2 Expressing Cells (a) Analysis of Electrogenic Transport in *Xenopus* Oocytes
RNA Preparation:

Human CNT1, CNT2 and CNT3 transporter cDNAs were subcloned into a modified pGEM plasmid that contains 5' and 3' untranslated sequences from the *Xenopus* β-actin gene. These sequences increase RNA stability and protein expression. Plasmid cDNA was linear zed and used as template for in vitro transcription (Epicentre Technologies transcription kit, 4:1 methylated:non-methylated GTP).

*Xenopus* Oocyte Isolation.

*Xenopus laevis* frogs were anesthetized by immersion in Tricaine (1.5 g/mL in deionized water) for 15 minutes. Oocytes were removed and digested in frog ringer solution (90 mM NaCl, 2 mM KCl, 1 mM $MgCl_2$, 10 mM NaHEPES, pH 7.45, no $CaCl_2$) with 1 mg/mL collagenase (Worthington Type 3) for 80-100 minutes with shaking. The oocytes were washed 6 times, and the buffer changed to frog ringer solution containing $CaCl_2$ (1.8 mM). Remaining follicle cells were removed if necessary. Cells were incubated at 16° C., and each oocyte injected with 10-20 µg RNA in 45 µL solution.

Electrophysiology Measurements.

Transport currents were measured 14 days after injection, using a standard two-electrode electrophysiology set-up (Geneclamp 500 amplifier, Digidata 1320/PCLAMP software and ADInstruments hardware and software were used for signal acquisition). Electrodes (2-4 mΩ) were microfabricated using a Sutter Instrument puller and filled with 3M KCl. The bath was directly grounded (transporter currents were less than 0.3 µA). Bath flow was controlled by an automated perfusion system (ALA Scientific Instruments, solenoid valves).

For transporter pharmacology, oocytes were clamped at 60 to −90 mV, and continuous current measurements acquired using PowerLab Software and an ADInstruments digitizer. Current signals were lowpass filtered at 20 Hz and acquired at 4-8 Hz. All bath and drug-containing solutions were frog ringers solution containing $CaCl_2$. Drugs were applied for 10-30 seconds until the induced current reached a new steady-state level, followed by a control solution until baseline currents returned to levels that preceded drug application. The difference current (baseline subtracted from peak current during drug application) reflected the net movement of charge resulting from electrogenic transport and was directly proportional to transport rate. Recordings were made from a single oocyte for up to 60 minutes, enabling 30-40 separate compounds to be tested per oocyte. Compound-induced currents were saturable and gave half-maximal values at substrate concentrations comparable to radiolabel competition experiments. To compare results between oocytes expressing different levels of transport activity, a saturating concentration of uridine or guanosine (1 mM) was used as a common reference to normalize results from test compounds. Using this normalization procedure $I_{max}$ (i.e. maximal induced current) for different compounds tested on different oocytes could be compared. Compound induced currents were determined to be specific by comparing responses to those observed in the absence of $Na^+$ (required for CNT transport) or in control oocytes not expressing a CNT transporter. Representative compounds (11), (26), (34), (36), (38), (50), (52), (60), (63) and (82) each elicited CNT1 and/or CNT3-specific currents significantly above background (at least 5% of $I_{max}$ for uridine) when tested at 1 mM on oocytes expressing either CNT1 or CNT3, confirming that these compounds serve as substrates for one or both of these transporters.

(b) Mass Spectroscopy Analysis of Active Transport of Compounds into Oocytes Expressing CNT1, CNT2, CNT3, ENT1 or ENT2

Transporters were expressed in oocytes as described above (a). Experiments were performed 3-5 days following injection. Oocytes were incubated with 0.1-3 mM of compounds for 10-30 minutes in frog ringers solution (90 mM NaCl, 2 mM KCl, 1 mM $MgCl_2$, 2 mM $CaCl_2$, 10 mM NaHEPES, pH 7.45, and 1% BSA). Experiments were performed at room temperature. For each compound, 4-7 oocytes were incubated for each transporter or non-expressing control. Following incubation, oocytes were rapidly washed 4 times in frog ringers solution, and placed one oocyte per well in a 96 well plate. Oocytes were homogenized in 0.15 mL solution containing 50% ethanol:water or 50% methanol:water. Precipitated protein or cellular matter was pelleted by spinning plates at 3000 RPM for 5 minutes. The solvent layer containing the extracted compounds was removed from wells.

The concentration of each compound in the oocyte extract was determined by analytical LC/MS/MS. Briefly, concentrations of test compound were determined using an API 2000 LC/MS/MS instrument equipped with an Agilent 1100 binary pump and a CTC HTS-PAL autosampler. The column was a Phenomenex hydro-RP 4.6×50 mm column. The mobile phase was water with 0.1% formic acid, 0.005% heptafluorobutyric acid (A) and acetonitrile with 0.1% formic acid, 0.005% heptafluorobutyric acid (B). The gradient condition was: 5% B for 0.5 min, then to 95% B in 2.5 min, then maintained at 95% B for 1 min. The mobile phase was returned to 5% B for 2 min. A TurboIonSpray source was used on the API 2000. The analysis was done in positive ion mode and an MRM transition of each analyte was first optimized using the standard solution. 10 µL of the samples were injected onto LC/MS/MS system for analysis. The peaks were integrated using Analyst 1.2 quantitation software. Specific uptake was determined by comparison of average uptake in oocytes expressing transporters with uptake in non-expressing oocytes. Significant uptake over background into cells expressing either ENT1, ENT2, CNT1 and CNT3 was observed for each of compounds (11), (38) and (62), while for compounds (26) and (36) specific uptake was observed into cells expressing either ENT1, ENT2 and CNT3.

6.62: Example 62

Standard Methods for Determination of Enzymatic Cleavage of Prodrugs in Vitro

The stability of gemcitabine prodrugs were evaluated in one or more in vitro systems using a variety of tissue preparations following methods known in the art. Tissues were obtained from commercial sources (e.g., Pel-Freez Biologicals, Rogers, AR, or GenTest Corporation, Woburn, Mass.). Experimental conditions used for the in vitro studies are described in Table 1 below. Each preparation was incubated with test compound at 37° C. for one hour. Aliquots (50 µL) were removed at 0, 30, and 60 min and quenched with 0.1% trifluoroacetic acid in acetonitrile. Samples were then centrifuged and analyzed by LC/MS/MS. Stability of prodrugs towards specific enzymes (e.g., peptidases, etc.) were also assessed in vitro by incubation with the purified enzyme:

Pancreatin Stability: Stability studies were conducted by incubating prodrug (5 µM) with 1% (w/v) pancreatin (Sigma, P-1625, from porcine pancreas) in 0.025 M Tris buffer containing 0.5 M NaCl (pH 7.5) at 37° C. for 60 min. The reaction was stopped by addition of 2 volumes of methanol. After centrifugation at 14,000 rpm for 10 min, the supernatant was removed and analyzed by LC/MS/MS.

Caco-2 Homogenate S9 Stability: Caco-2 cells were grown for 21 days prior to harvesting. Culture medium was removed and cell monolayers were rinsed and scraped off into ice-cold 10 mM sodium phosphate/0.15 M potassium chloride, pH 7.4. Cells were lysed by sonication at 4° C. using a probe sonicator. Lysed cells were then transferred into 1.5 mL centrifuge vials and centrifuged at 9000 g for 20 min at 4° C. The resulting supernatant (Caco-2 cell homogenate S9 fraction) was aliquoted into 0.5 mL vials and stored at −80° C. until used.

For stability studies, prodrug (5 µM) was incubated in Caco-2 homogenate S9 fraction (0.5 mg protein per mL) for 60 min at 37° C. Concentrations of intact prodrug and released gemcitabine were determined at zero time and 60 minutes using LC/MS/MS.

Preferred prodrugs demonstrate minimal cleavage to produce free gemcitabine within a 60 minute period in Caco-2 cells (representative of human enterocytes), but efficient conversion in either plasma or liver S-9, as summarized in Table 2.

TABLE 1

Standard Conditions for Prodrug In Vitro Metabolism Studies

| Preparation | Substrate Concentration | Cofactors* |
|---|---|---|
| Mouse Plasma | 2.0 μM | None |
| Human Plasma | 2.0 μM | None |
| Mouse Liver S9 (0.5 mg/mL) | 2.0 μM | NADPH |
| Human Liver S9 (0.5 mg/mL) | 2.0 μM | NADPH |
| Caco-2 Homogenate | 5.0 μM | None |
| Pancreatin | 5.0 μM | None |

*NADPH generating system, e.g., 1.3 mM NADP+, 3.3 mM glucose-6-phosphate, 0.4 U/mL glucose-6-phosphate dehydrogenase, 3.3 mM magnesium chloride and 0.95 mg/mL potassium phosphate, pH 7.4.

TABLE 2

% of Gemcitabine Released from Representative Gemcitabine Prodrugs after 60 min. in Various Tissue Preparations

|  | (3) | (26) | (36) | (38) | (62) | (63) |
|---|---|---|---|---|---|---|
| Mouse Plasma | nd | 23 | 74 | 27 | 54 | 55 |
| Human Plasma | 66 | 1 | 3 | 0 | 4 | 2 |
| Mouse Liver S9 (0.5 mg/mL) | nd | 2 | 4 | 0 | 24 | 54 |
| Human Liver S9 (0.5 mg/mL) | 63 | 4 | 3 | 0 | 26 | 32 |
| Caco-2 S9 (0.5 mg/mL) | 77 | 1 | 1 | 0 | 12 | 9 |
| Pancreatin (10 mg/mL) | 0 | 0 | 2 | 0 | 0 | 1 |

6.63: Example 63

Evaluation of Pharmacokinetics and Intestinal Exposure to Gemcitabine After Oral Dosing of Prodrugs in Mice Compounds were each administered to groups of 44 male mice by oral gavage at a dose of 20 mg-eq. gemcitabine per kg body weight. Blood samples (0.5 mL) were obtained by cardiac puncture from 4 animals at each time point (1, 5, 10, 15, 30, 45 minutes and 1, 2, 4, 6 and 24 hr post-dosing). Samples were immediately transferred to tubes containing 10 μL of tetrahydrouridine (50 μg/mL in 50% methanol/water) to prevent further deamination and aliquots (100 μL) were quenched with a solution of 1% w/w formic acid in acetonitrile (300 μL). Quenched blood samples were stored at −80° C. until analyzed. Following collection of blood samples, the small intestine of each animal was removed, rinsed with saline, scraped to remove the mucosal layer, and the mucosal tissue was transferred to a pre-weighed vial containing 10 μL of tetrahydrouridine (50 μg/mL in 50% methanol/water). Sample vials were snap frozen in dry ice/acetone and stored at −80° C. until analyzed. Mucosal tissue samples were diluted 1:10 in water and 100 μL of the resulting sample was added to 400 μL of methanol. Concentrations of intact prodrug, gemcitabine, and deaminated gemcitabine in quenched blood samples and diluted mucosal tissues were determined using a sensitive and specific LC/MS/MS method. Data were used to calculate the ratio of the maximum concentration ($C_{max}$) of gemcitabine in intestinal tissue (μg/g) to the $C_{max}$ of gemcitabine in blood (μg/mL). For example, following oral administration of gemcitabine to mice at 20 mg-eq. gemcitabine/kg, the ratio of $C_{max}$ of gemcitabine in intestinal mucosal tissue to the $C_{max}$ in the plasma was 270. In contrast, following oral administration of and equimolar dose of compound (11) to mice, the ratio of $C_{max}$ of released gemcitabine in intestinal mucosal tissue to the $C_{max}$ in the blood was 50.

Prodrugs compounds (3), (11), (26), (36), (38), (62) and (63) showed substantial oral bioavailability as gemcitabine in mice ($F_{po}$=20% for gemcitabine itself), with compounds (38) and (62), for example, showing at least 2-fold greater systemic gemcitabine exposures than after dosing gemcitabine itself.

Finally, it should be noted that there are alternative ways of implementing the present invention. Accordingly, the present embodiments are to be considered as illustrative and not restrictive and the invention is not to be limited to the details given herein, but may be modified within the scope and equivalents of the appended claims. All publications and patents cited herein are incorporated by reference.

What is claimed is:

1. A compound of structural Formula (I):

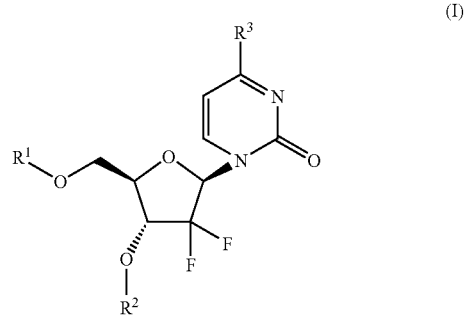

or a pharmaceutically acceptable salt, hydrate, solvate or N-oxide thereof, wherein:

$R^1$ is hydrogen, acyl, substituted acyl, acyloxyalkylcarbonyl, substituted acyloxyalkylcarbonyl, oxycarbonyl, substituted oxycarbonyl or

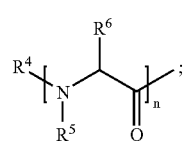

$R^2$ is hydrogen, acyl, substituted acyl, acyloxyalkylcarbonyl, substituted acyloxyalkylcarbonyl, oxycarbonyl, substituted oxycarbonyl or

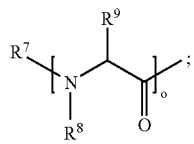

$R^3$ is —N═C($R^{10}$)($R^{11}$) or —NH$R^{12}$;

n and o are independently integers from 1 to 3;

$R^4$ and $R^7$ are independently selected from the group consisting of hydrogen, alkyl, substituted alkyl, acyl, substituted acyl, acyloxyalkylcarbonyl, substituted acyloxyalkylcarbonyl, arylalkyl, substituted arylalkyl, oxycarbonyl and substituted oxycarbonyl;

$R^5$ and $R^8$ are independently selected from the group consisting of hydrogen, alkyl, substituted alkyl, acyl, substituted acyl, acyloxyalkylcarbonyl, substituted acyloxyalkylcarbonyl, arylalkyl, substituted arylalkyl, cycloheteroalkyl, substituted cycloheteroalkyl, heteroalkyl, substituted heteroalkyl, oxycarbonyl and substituted oxycarbonyl;

$R^6$ and $R^9$ are independently selected from the group consisting of hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl;

or optionally, $R^5$ and $R^6$ together with the nitrogen atom to which they are bonded form a cycloheteroalkyl or substituted cycloheteroalkyl ring;

or optionally, $R^8$ and $R^9$ together with the nitrogen atom to which they are bonded form a cycloheteroalkyl or substituted cycloheteroalkyl ring;

$R^{10}$ and $R^{11}$ are independently selected from the group consisting of hydrogen, acyl, substituted acyl, alkyl, substituted alkyl, alkoxy, substituted alkoxy, alkylamino, substituted alkylamino, amido, substituted amido, aryl, substituted aryl, arylalkyl, substituted arylalkyl, cycloalkyl, substituted cycloalkyl, cycloheteroalkyl, substituted cycloheteroalkyl, dialkylamino, substituted dialkylamino, heteroalkyl, substituted heteroalkyl, heteroaryl, substituted heteroaryl, heteroarylalkyl and substituted heteroarylalkyl with the proviso that either $R^{10}$ or $R^{11}$ is hydrogen;

$R^{12}$ is $C_5$-$C_9$ acyl or $C_5$-$C_9$ substituted acyl;

with the provisos that:

neither $R^1$ nor $R^2$ is benzoyl, $C_{18}$-$C_{20}$ acyl, tert-butoxycarbonyl or phenylaminocarbonyl;

at least one of $R^1$ and $R^2$ is not hydrogen when $R^3$ is —N═C($R^{10}$)($R^{11}$) and $R^{10}$ and $R^{11}$ are hydrogen; and $R^3$ is not benzylcarbonylamino or phenylcarbonylamino.

2. The compound of claim 1, wherein $R^1$ is hydrogen, acyl, substituted acyl, acyloxyalkylcarbonyl, substituted acyloxyalkylcarbonyl, oxycarbonyl or substituted oxycarbonyl.

3. The compound of claim 1, wherein $R^1$ is hydrogen, acyl or substituted acyl.

4. The compound of claim 1, wherein $R^1$ is hydrogen, acyloxyalkylcarbonyl, substituted acyloxyalkylcarbonyl, oxycarbonyl or substituted oxycarbonyl.

5. The compound of claim 1, wherein $R^2$ is hydrogen, acyl, substituted acyl, acyloxyalkylcarbonyl, substituted acyloxyalkylcarbonyl, oxycarbonyl or substituted oxycarbonyl.

6. The compound of claim 1, wherein $R^2$ is hydrogen, acyl or substituted acyl.

7. The compound of claim 1, wherein $R^2$ is hydrogen, acyloxyalkylcarbonyl, substituted acyloxyalkylcarbonyl, oxycarbonyl or substituted oxycarbonyl.

8. The compound of claim 1, wherein $R^{10}$ and $R^{11}$ are independently selected from the group consisting of hydrogen, alkoxy, substituted alkoxy, alkylamino, substituted alkylamino, amido, substituted amido, arylalkyl, substituted arylalkyl, dialkylamino, substituted dialkylamino, heteroalkyl, substituted heteroalkyl, heteroaryl, substituted heteroaryl, heteroarylalkyl and substituted heteroarylalkyl.

9. The compound of claim 1, wherein $R^{10}$ and $R^{11}$ are independently selected from the group consisting of hydrogen, alkoxy, substituted alkoxy, alkylamino, substituted alkylamino, amido, substituted amido, dialkylamino and substituted dialkylamino.

10. The compound of claim 1, wherein $R^1$ and $R^2$ are independently hydrogen, acyl, substituted acyl, acyloxyalkylcarbonyl, substituted acyloxyalkylcarbonyl, oxycarbonyl or substituted oxycarbonyl.

11. The compound of claim 1, wherein $R^1$ and $R^2$ are independently hydrogen, acyl or substituted acyl.

12. The compound of claim 1, wherein $R^1$ and $R^2$ are independently hydrogen, acyloxyalkylcarbonyl, substituted acyloxyalkylcarbonyl, oxycarbonyl or substituted oxycarbonyl.

13. The compound of claim 1, wherein $R^1$ and $R^2$ are independently hydrogen, acyl, substituted acyl, acyloxyalkylcarbonyl, substituted acyloxyalkylcarbonyl, oxycarbonyl or substituted oxycarbonyl and $R^{10}$ and $R^{11}$ are independently selected from the group consisting of hydrogen, alkoxy, substituted alkoxy, alkylamino, substituted alkylamino, amido, substituted amido, arylalkyl, substituted arylalkyl, dialkylamino, substituted dialkylamino, heteroalkyl, substituted heteroalkyl, heteroaryl, substituted heteroaryl, heteroarylalkyl and substituted heteroarylalkyl.

14. The compound of claim 1, wherein $R^1$ and $R^2$ are independently hydrogen, acyl or substituted acyl and-$R^{10}$ and $R^{11}$ are independently selected from the group consisting of hydrogen, alkoxy, substituted alkoxy, alkylamino, substituted alkylamino, amido, substituted amido, dialkylamino and substituted dialkylamino.

15. The compound of claim 1, wherein $R^1$ and $R^2$ are independently hydrogen, acyloxyalkylcarbonyl, substituted acyloxyalkylcarbonyl, oxycarbonyl or substituted oxycarbonyl and $R^{10}$ and $R^{11}$ are independently selected from the group consisting of hydrogen, alkoxy, substituted alkoxy, alkylamino, substituted alkylamino, amido, substituted amido, dialkylamino and substituted dialkylamino.

16. The compound of claim 1, wherein n and o are 1.

17. The compound of claim 1, wherein $R^4$ and $R^7$ are independently selected from the group consisting of hydrogen, acyl, substituted acyl, acyloxyalkylcarbonyl, substituted acyloxyalkylcarbonyl, oxycarbonyl and substituted oxycarbonyl.

18. The compound of claim 1, wherein $R^4$ and $R^7$ are independently selected from the group consisting of hydrogen, acyl and substituted acyl.

19. The compound of claim 1, wherein $R^4$ is selected from the group consisting of hydrogen, acyl, substituted acyl, acyloxyalkylcarbonyl, substituted acyloxyalkylcarbonyl, oxycarbonyl and substituted oxycarbonyl.

20. The compound of claim 1, wherein $R^4$ is selected from the group consisting of hydrogen, acyl and substituted acyl.

21. The compound of claim 1, wherein $R^7$ is selected from the group consisting of hydrogen, acyl, substituted acyl, acyloxyalkylcarbonyl, substituted acyloxyalkylcarbonyl, oxycarbonyl and substituted oxycarbonyl.

22. The compound of claim 1, wherein $R^7$ is selected from the group consisting of hydrogen, acyl and substituted acyl.

23. The compound of claim 1, wherein $R^4$ and $R^7$ are independently selected from the group consisting of hydrogen, acyl, substituted acyl, acyloxyalkylcarbonyl, substituted acyloxyalkylcarbonyl, oxycarbonyl and substituted oxycarbonyl.

24. The compound of claim 1, wherein $R^4$ and $R^7$ are independently selected from the group consisting of hydrogen, acyl and substituted acyl.

25. The compound of claim 1, wherein $R^6$ and $R^9$ are independently selected from the group consisting of hydrogen, alkanyl, substituted alkanyl, aryl, substituted aryl, arylalkanyl, substituted arylalkanyl, cycloalkanyl, heteroarylalkyl and substituted heteroarylalkanyl.

26. The compound of claim 1, wherein $R^6$ and $R^9$ are independently selected from the group consisting of hydrogen, alkanyl and cycloalkanyl.

27. The compound of claim 26, wherein $R^6$ and $R^9$ are independently selected from the group consisting of hydrogen, methyl, isopropyl, isobutyl, sec-butyl, tert-butyl, cyclopentyl and cyclohexyl.

28. The compound of claim 1, wherein $R^6$ and $R^9$ are independently substituted alkanyl.

29. The compound of claim 28, wherein $R^6$ and $R^9$ are independently selected from the group consisting of —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ and —CH$_2$CH$_2$CH$_2$NHC(NH)NH$_2$.

30. The compound of claim 1, wherein $R^6$ and $R^9$ are independently selected from the group consisting of aryl, arylalkanyl, substituted arylalkanyl and heteroarylalkanyl.

31. The compound of claim 30, wherein $R^6$ and $R^9$ are independently selected from the group consisting of phenyl, benzyl, 4-hydroxybenzyl, 4-imidazolylmethyl and 3-indolylmethyl.

32. The compound of claim 1, wherein $R^5$ and $R^6$ or $R^8$ and $R^9$ together with the nitrogen atom to which they are bonded form a cycloheteroalkyl or substituted cycloheteroalkyl ring.

33. The compound of claim 32, wherein $R^5$ and $R^6$ or $R^8$ and $R^9$ together with the nitrogen atom to which they are bonded form an azetidine, pyrrolidine or piperidine ring.

34. The compound of claim 1, wherein $R^1$ is hydrogen or

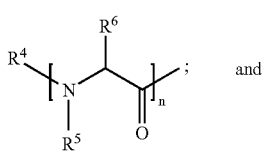

$R^2$ is independently hydrogen, acyl, substituted acyl, acyloxycarbonyl, substituted acyloxycarbonyl, oxycarbonyl or substituted oxycarbonyl.

35. The compound of claim 1, wherein $R^1$ is hydrogen or

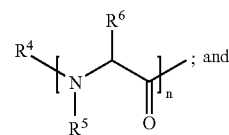

$R^2$ is hydrogen or

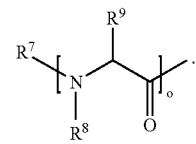

36. The compound of claim 1, wherein $R^1$ is hydrogen or

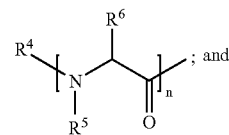

$R^2$ is hydrogen, acyl, substituted acyl, acyloxycarbonyl, substituted acyloxycarbonyl, oxycarbonyl or substituted oxycarbonyl.

37. The compound of claim 1, wherein $R^1$ is hydrogen or

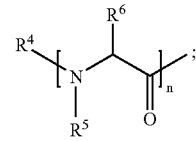

$R^2$ is hydrogen, acyl, substituted acyl, acyloxycarbonyl, substituted acyloxycarbonyl, oxycarbonyl or substituted oxycarbonyl; and
$R^{10}$ and $R^{11}$ are independently selected from the group consisting of hydrogen, alkoxy, substituted alkoxy, alkylamino, substituted alkylamino, amido, substituted amido, dialkylamino and substituted dialkylamino.

38. The compound of claim 1, wherein $R^1$ is hydrogen or

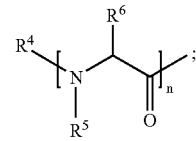

$R^2$ is hydrogen or

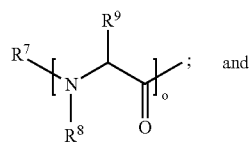

$R^{10}$ and $R^{11}$ are independently selected from the group consisting of hydrogen, alkoxy, substituted alkoxy, alkylamino, substituted alkylamino, amido, substituted amido, dialkylamino and substituted dialkylamino.

39. The compound of claim 1, wherein $R^1$ is

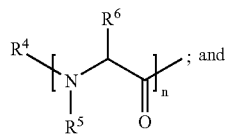; and $R^2$ is hydrogen.

40. The compound of claim 39, wherein n is 1;
$R^4$ and $R^5$ are hydrogen;
$R^6$ is hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)3NH$_2$, —CH$_2$CH$_2$CH$_2$NHC(NH)NH$_2$, phenyl, benzyl, 4-hydroxybenzyl, 4-imidazolylmethyl or 3-indolylmethyl;

or optionally, $R^5$ and $R^6$ together with the nitrogen atom to which they are bonded form an azetidine, pyrrolidine or piperidine ring.

41. The compound of claim 40, wherein $R^6$ is methyl, isopropyl, isobutyl, sec-butyl, tert-butyl or benzyl.

42. The compound of claim 39, wherein n is 1;
$R^4$ is oxycarbonyl or substituted oxycarbonyl;
$R^5$ is hydrogen; and
$R^6$ substituted alkyl.

43. The compound of claim 42, wherein $R^4$ is tert-butoxycarbonyl or benzyloxycarbonyl; and
$R^6$ is —CH$_2$CO$_2$H or —CH$_2$CH$_2$CO$_2$H.

44. The compound of claim 1, wherein $R^1$ is acyl, substituted acyl, oxycarbonyl or substituted oxycarbonyl; and
$R^2$ is hydrogen.

45. The compound of claim 44, wherein $R^1$ is substituted acyl or substituted oxycarbonyl.

46. The compound of claim 45, wherein $R^1$ is —C(O)(CH$_2$)$_r$CO$_2$H or —C(O)O(CH$_2$)$_r$CO$_2$H; and
r is an integer from 1 to 4.

47. The compound of claim 1, wherein $R^1$ is hydrogen or

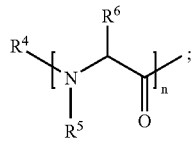;

$R^2$ is hydrogen; and
$R^3$ is —N═C($R^{10}$)($R^{11}$) and $R^{10}$ and $R^{11}$ are independently selected from the group consisting of hydrogen, alkoxy, substituted alkoxy, alkylamino, substituted alkylamino, amido, substituted amido, arylalkyl, substituted arylalkyl, dialkylamino, substituted dialkylamino, heteroalkyl, substituted heteroalkyl, heteroaryl, substituted heteroaryl, heteroarylalkyl and substituted heteroarylalkyl.

48. The compound of claim 47, wherein n is 1;
$R^4$ and $R^5$ are hydrogen;
$R^6$ is hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)3NH$_2$, —CH$_2$CH$_2$CH$_2$NHC(NH)NH$_2$, phenyl, benyl, 4-hydroxybenzyl, 4-imidazolylmethyl or 3-indolylmethyl;

or optionally, $R^5$ and $R^6$ together with the nitrogen atom to which they are bonded form an azetidine, pyrrolidine or piperidine ring; and $R^{10}$ and $R^{11}$ are independently selected from the group consisting of hydrogen, alkoxy, substituted alkoxy, alkylamino, substituted alkylamino, dialkylamino and substituted dialkylamino.

49. The compound of claim 48, wherein $R^6$ is methyl, isopropyl, isobutyl, sec-butyl, tert-butyl or benzyl; and
$R^{10}$ and $R^{11}$ are independently selected from the group consisting of hydrogen, methoxy and dimethylamino.

50. The compound of claim 47, wherein n is 1;
$R^4$ is oxycarbonyl or substituted oxycarbonyl;
$R^5$ is hydrogen;
$R^6$ is substituted alkyl;
and $R^{10}$ and $R^1$ are independently selected from the group consisting of hydrogen, alkoxy, substituted alkoxy, alkylamino, substituted alkylamino, dialkylamino and substituted dialkylamino.

51. The compound of claim 50, wherein $R^4$ is tert-butoxycarbonyl or benzyloxycarbonyl;
$R^6$ is —CH$_2$CO$_2$H or —CH$_2$CH$_2$CO$_2$H; and
$R^{10}$ and $R^{11}$ are independently selected from the group consisting of hydrogen, methoxy and dimethylamino.

52. The compound of claim 1, wherein $R^1$ is acyl, substituted acyl, oxycarbonyl or substituted oxycarbonyl;
$R^2$ is hydrogen; and
$R^3$ is —N═C($R^{10}$)($R^{11}$) and $R^{10}$ and $R^{11}$ are independently selected from the group consisting of hydrogen, alkoxy, substituted alkoxy, alkylamino, substituted alkylamino, amido, substituted amido, arylalkyl, substituted arylalkyl, dialkylamino, substituted dialkylamino, heteroalkyl, substituted heteroalkyl, heteroaryl, substituted heteroaryl, heteroarylatkyl and substituted heteroarylalkyl.

53. The compound of claim 52, wherein $R^1$ is substituted acyl or substituted oxycarbonyl; and
$R^{10}$ and $R^{11}$ are independently selected from the group consisting of hydrogen, alkoxy, substituted alkoxy, alkylamino, substituted alkylamino, dialkylamino and substituted dialkylamino.

54. The compound of claim 53, wherein $R^1$ is —C(O)(CH$_2$)$_r$CO$_2$H or —C(O)O(CH$_2$)$_r$CO$_2$H;
r is an integer from 1 to 4; and
$R^{10}$ and $R^{11}$ are independently selected from the group consisting of hydrogen, methoxy and dimethylamino.

55. The compound of claim 1, wherein $R^1$ is hydrogen; and
$R^2$ is

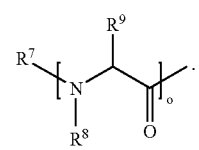

56. The compound of claim 55, wherein o is 1;
$R^7$ and $R^8$ are hydrogen;
$R^9$ is hydrogen, methyl, isopropyl, isobutyl, sec-butyl, tert-butyl, cyclopentyl, cyclohexyl, —CH$_2$OH, —CH (OH)CH₃, —CH₂CO₂H, —CH₂CH₂CO₂H, —CH₂CONH₂, —CH₂CH₂CONH₂, —CH₂CH₂SCH₃, —CH₂SH, —CH₂(CH₂)₃NH₂, —CH₂CH₂CH₂NHC(NH)NH₂, phenyl, benzyl, 4-hydroxybenzyl, 4-imidazolylmethyl or 3-indolylmethyl; and or optionally, R⁸ and R⁹ together with the nitrogen atom to which they are bonded form an azetidine, pyrrolidine or piperidine ring.

57. The compound of claim 56, wherein R⁹ is methyl, isopropyl, isobutyl, sec-butyl, tert-butyl or benzyl.

58. The compound of claim 55, wherein o is 1;
R⁷ is oxycarbonyl or substituted oxycarbonyl;
R⁸ is hydrogen; and
R⁹ is substituted alkyl.

59. The compound of claim 58, wherein R⁷ is tert-butoxycarbonyl or benzyloxycarbonyl; and
R⁹ is —CH₂CO₂H or —CH₂CH₂CO₂H.

60. The compound of claim 1, wherein R¹ is hydrogen; and
R² is acyl, substituted acyl, oxycarbonyl or substituted oxycarbonyl.

61. The compound of claim 60, wherein R² is substituted acyl or substituted oxycarbonyl.

62. The compound of claim 61, wherein R² is —C(O)(CH₂)ₛCO₂H or —C(O)O(CH₂)ₛCO₂H; and
s is an integer from 1 to 4.

63. The compound of claim 1, wherein R¹ is hydrogen; R² is

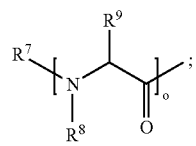

and R³ is —N═C(R¹⁰)(R¹¹) and R¹⁰ and R¹¹ are independently selected from the group consisting of hydrogen, alkoxy, substituted alkoxy, alkylamino, substituted alkylamino, amido, substituted amido, arylalkyl, substituted arylalkyl, dialkylamino, substituted dialkylamino, heteroalkyl, substituted heteroalkyl, heteroaryl, substituted heteroaryl, heteroarylalkyl and substituted heteroarylalkyl.

64. The compound of claim 63, wherein o is 1;
R⁷ and R⁸ are hydrogen;
R⁹ is hydrogen, methyl, isopropyl, isobutyl, sec-butyl, tert-butyl, cyclopentyl, cyclohexyl, —CH₂OH, —CH(OH)CH₃, —CH₂CO₂H, —CH₂CH₂CO₂H, —CH₂CONH₂, —CH₂CH₂CONH₂, —CH₂CH₂SCH₃, —CH₂SH, —CH₂(CH₂)₃NH₂, —CH₂CH₂CH₂NHC(NH)NH₂, phenyl, benzyl, 4-hydroxybenzyl, 4-imidazolylmethyl or 3-indolylmethyl;

or optionally, R⁸ and R⁹ together with the nitrogen atom to which they are bonded form an azetidine, pyrrolidine or piperidine ring; and R¹⁰ and R¹¹ are independently selected from the group consisting of hydrogen, alkoxy, substituted alkoxy, alkylamino, substituted alkylamino, dialkylamino and substituted dialkylamino.

65. The compound of claim 64, wherein R⁹ is methyl, isopropyl, isobutyl, sec-butyl, tert-butyl or benzyl; and
R¹⁰ and R¹¹ are independently selected from the group consisting of hydrogen, methoxy and dimethylamino.

66. The compound of claim 63, wherein o is 1;
R⁷ is oxycarbonyl or substituted oxycarbonyl;
R⁸ is hydrogen;
R⁹ is substituted alkyl; and
R¹⁰ and R¹¹ are independently selected from the group consisting of hydrogen, alkoxy, substituted alkoxy, alkylamino, substituted alkylamino, dialkylamino and substituted dialkylamino.

67. The compound of claim 66, wherein R⁷ is tert-butoxycarbonyl or benzyloxycarbonyl;
R⁹ is —CH₂CO₂H or —CH₂CH₂CO₂H; and
R¹⁰ and R¹¹ are independently selected from the group consisting of hydrogen, methoxy and dimethylamino.

68. The compound of claim 1, wherein R¹ is hydrogen;
R² is acyl, substituted acyl, oxycarbonyl or substituted oxycarbonyl; and
R³ is —N═C(R¹⁰)(R¹¹) and R¹⁰ and R¹¹ are independently selected from the group consisting of hydrogen, alkoxy, substituted alkoxy, alkylamino, substituted alkylamino, amido, substituted amido, arylalkyl, substituted arylalkyl, dialkylamino, substituted dialkylamino, heteroalkyl, substituted heteroalkyl, heteroaryl, substituted heteroaryl, heteroarylalkyl and substituted heteroarylalkyl.

69. The compound of claim 68, wherein R² is substituted acyl or substituted oxycarbonyl; and
R¹⁰ and R¹¹ are independently selected from the group consisting of hydrogen, alkoxy, substituted alkoxy, alkylamino, substituted alkylamino, dialkylamino and substituted dialkylamino.

70. The compound of claim 69, wherein R² is —C(O)(CH₂)ₛCO₂H or —C(O)O(CH₂)ₛCO₂H;
s is an integer from 1 to 4; and
R¹⁰ and R¹¹ are independently selected from the group consisting of hydrogen, methoxy and dimethylamino.

71. The compound of claim 1, wherein R¹ and R² are independently selected from the group consisting of hydrogen, acyl, substituted acyl, oxycarbonyl or substituted oxycarbonyl; and
R³ is

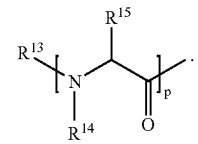

72. The compound of claim 71, wherein R¹ and R² are independently selected from the group consisting of hydrogen, acyl and oxycarbonyl.

73. The compound of claim 72, wherein R¹ is hydrogen, —C(O)OR¹⁹, or —C(O)OR¹⁹, where R¹⁹ is $C_{1-6}$ alkyl; and
R² is hydrogen, —C(O)R²⁰, or —C(O)OR²⁰, where R²⁰ is $C_{1-6}$ alkyl.

74. The compound of claim 1, wherein R¹ and R² are independently selected from the group consisting of hydrogen, acyl, substituted acyl, oxycarbonyl or substituted oxycarbonyl.

75. The compound of claim 74, wherein R¹ and R² are hydrogen, acyl or oxycarbonyl.

76. The compound of claim 1, wherein $R^1$ and $R^2$ are independently selected from the group consisting of hydrogen, —C(O)$R^{19}$ or —C(O)O$R^{19}$; and $R^{19}$ is $C_{1-6}$ alkyl.

77. The compound of claim 76, wherein $R^1$ and $R^2$ are each hydrogen.

78. The compound of claim 1, wherein $R^1$ and $R^2$ are independently selected from the group consisting of hydrogen, —C(O)$R^{19}$ or —C(O)O$R^{19}$; and $R^{19}$ is $C_{1-6}$ alkyl.

79. The compound of claim 1, wherein $R^1$ and $R^2$ are independently hydrogen, acyl, substituted acyl, oxycarbonyl or substituted oxycarbonyl; and $R^3$ is —N═C($R^{10}$)($R^{11}$) and $R^{10}$ and $R^{11}$ are independently selected from the group consisting of hydrogen, alkoxy, substituted alkoxy, alkylamino, substituted alkylamino, dialkylamino and substituted dialkylamino.

80. The compound of claim 79, wherein $R^1$ and $R^2$ are independently hydrogen, acyl or oxycarbonyl; and $R^{10}$ and $R^{11}$ are independently selected from the group consisting of hydrogen, alkoxy, substituted alkoxy, dialkylamino and substituted dialkylamino.

81. The compound of claim 80, wherein $R^1$ is hydrogen, —C(O)$R^{19}$, or —C(O)O$R^{19}$, where $R^{19}$ is $C_{1-6}$ alkyl;

$R^2$ is hydrogen, —C(O)$R^{20}$, or —C(O)O$R^{20}$, where $R^{20}$ is $C_{1-6}$ alkyl; and $R^{10}$ and $R^{11}$ are independently selected from the group consisting of hydrogen, ethoxy and diethylamino.

82. A compound of structural Formula (II):

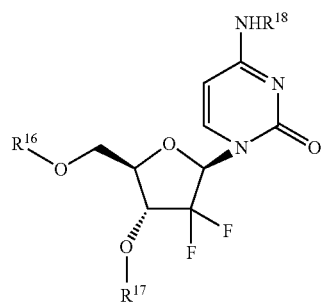

(II)

or a pharmaceutically available salt, hydrate, solvate or N-oxide thereof wherein:

$R^{16}$ $R^{17}$ and $R^{18}$ are independently hydrogen or

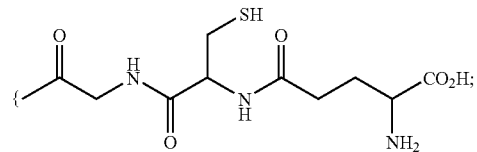

with the proviso that at least one of $R^{16}$, $R^{17}$ and $R^{18}$ is not hydrogen.

83. A pharmaceutical composition comprising the compound of claim 1 or claim 82 and a pharmaceutically acceptable vehicle.

* * * * *